US011996181B2

(12) United States Patent
Xue et al.

(10) Patent No.: US 11,996,181 B2
(45) Date of Patent: May 28, 2024

(54) AUTOMATIC DETECTION OF TOOTH TYPE AND ERUPTION STATUS

(71) Applicant: ALIGN TECHNOLOGY, INC., San Jose, CA (US)

(72) Inventors: Ya Xue, Chapel Hill, NC (US); Jeeyoung Choi, Sunnyvale, CA (US); Justin B. Moore, Raleigh, NC (US); Anton Spiridonov, Cary, NC (US)

(73) Assignee: Align Technology, Inc., San Jose, CA (US)

( * ) Notice: Subject to any disclaimer, the term of this patent is extended or adjusted under 35 U.S.C. 154(b) by 70 days.

(21) Appl. No.: 16/010,087

(22) Filed: Jun. 15, 2018

(65) Prior Publication Data

US 2018/0360567 A1 Dec. 20, 2018

Related U.S. Application Data

(60) Provisional application No. 62/521,166, filed on Jun. 16, 2017.

(51) Int. Cl.
*A61C 7/00* (2006.01)
*A61C 7/08* (2006.01)
(Continued)

(52) U.S. Cl.
CPC ............ *G16H 30/40* (2018.01); *A61C 7/002* (2013.01); *A61C 7/08* (2013.01); *A61C 9/0053* (2013.01);
(Continued)

(58) Field of Classification Search
CPC ..... A61C 7/08; A61C 7/002; A61C 2007/004; A61C 9/0053; G06T 2207/20084; G16H 30/40
See application file for complete search history.

(56) References Cited

U.S. PATENT DOCUMENTS 2,171,695 A 9/1939 Harper
2,467,432 A 4/1949 Kesling
(Continued)

FOREIGN PATENT DOCUMENTS

AU 517102 B 11/1977
AU 3031677 A 11/1977
(Continued)

OTHER PUBLICATIONS

US 8,553,966 B1, 10/2013, Alpern et al. (withdrawn)
(Continued)

*Primary Examiner* — Jacqueline T Johanas
*Assistant Examiner* — Shannel Nicole Belk
(74) *Attorney, Agent, or Firm* — Shay Glenn LLP

(57) ABSTRACT

Provided herein are systems and methods for detecting the eruption state (e.g., tooth type and/or eruption status) of a target tooth. A patient's dentition may be scanned and/or segmented. A target tooth may be identified. Dental features, principal component analysis (PCA) features, and/or other features may be extracted and compared to those of other teeth, such as those obtained through automated machine learning systems. A detector can identify and/or output the eruption state of the target tooth, such as whether the target tooth is a fully erupted primary tooth, a permanent partially erupted/un-erupted tooth, or a fully erupted permanent tooth.

23 Claims, 17 Drawing Sheets

(51) Int. Cl.
*A61C 9/00* (2006.01)
*G06F 18/21* (2023.01)
*G06F 18/2413* (2023.01)
*G06F 18/243* (2023.01)
*G06T 7/10* (2017.01)
*G06T 7/66* (2017.01)
*G16H 30/40* (2018.01)
*G06N 3/08* (2023.01)
*G16H 50/20* (2018.01)
*G16H 50/50* (2018.01)

(52) U.S. Cl.
CPC ........ *G06F 18/21* (2023.01); *G06F 18/24147* (2023.01); *G06F 18/24323* (2023.01); *G06T 7/10* (2017.01); *G06T 7/66* (2017.01); *G06N 3/08* (2013.01); *G06T 2207/20081* (2013.01); *G06T 2207/20084* (2013.01); *G06T 2207/20164* (2013.01); *G06T 2207/30036* (2013.01); *G16H 50/20* (2018.01); *G16H 50/50* (2018.01)

(56) References Cited

U.S. PATENT DOCUMENTS

| | | | |
|---|---|---|---|
| 2,531,222 | A | 11/1950 | Kesling |
| 3,379,193 | A | 4/1968 | Monsghan |
| 3,385,291 | A | 5/1968 | Martin |
| 3,407,500 | A | 10/1968 | Kesling |
| 3,478,742 | A | 11/1969 | Bohlmann |
| 3,496,936 | A | 2/1970 | Gores |
| 3,533,163 | A | 10/1970 | Kirschenbaum |
| 3,556,093 | A | 1/1971 | Quick |
| 3,600,808 | A | 8/1971 | Reeve |
| 3,660,900 | A | 5/1972 | Andrews |
| 3,683,502 | A | 8/1972 | Wallshein |
| 3,738,005 | A | 6/1973 | Cohen et al. |
| 3,860,803 | A | 1/1975 | Levine |
| 3,885,310 | A | 5/1975 | Northcutt |
| 3,916,526 | A | 11/1975 | Schudy |
| 3,922,786 | A | 12/1975 | Lavin |
| 3,949,477 | A | 4/1976 | Cohen et al. |
| 3,950,851 | A | 4/1976 | Bergersen |
| 3,983,628 | A | 10/1976 | Acevedo |
| 4,014,096 | A | 3/1977 | Dellinger |
| 4,117,596 | A | 10/1978 | Wallshein |
| 4,183,141 | A | 1/1980 | Dellinger |
| 4,195,046 | A | 3/1980 | Kesling |
| 4,253,828 | A | 3/1981 | Coles et al. |
| 4,255,138 | A | 3/1981 | Frohn |
| 4,299,568 | A | 11/1981 | Crowley |
| 4,324,546 | A | 4/1982 | Heitlinger et al. |
| 4,324,547 | A | 4/1982 | Arcan et al. |
| 4,348,178 | A | 9/1982 | Kurz |
| 4,419,992 | A | 12/1983 | Chorbajian |
| 4,433,956 | A | 2/1984 | Witzig |
| 4,439,154 | A | 3/1984 | Mayclin |
| 4,449,928 | A | 5/1984 | von Weissenfluh |
| 4,478,580 | A | 10/1984 | Barrut |
| 4,500,294 | A | 2/1985 | Lewis |
| 4,505,673 | A | 3/1985 | Yoshii |
| 4,519,386 | A | 5/1985 | Sullivan |
| 4,526,540 | A | 7/1985 | Dellinger |
| 4,553,936 | A | 11/1985 | Wang |
| 4,575,330 | A | 3/1986 | Hull |
| 4,575,805 | A | 3/1986 | Moermann et al. |
| 4,591,341 | A | 5/1986 | Andrews |
| 4,608,021 | A | 8/1986 | Barrett |
| 4,609,349 | A | 9/1986 | Cain |
| 4,611,288 | A | 9/1986 | Duret et al. |
| 4,629,424 | A | 12/1986 | Lauks et al. |
| 4,638,145 | A | 1/1987 | Sakuma et al. |
| 4,656,860 | A | 4/1987 | Orthuber et al. |
| 4,663,720 | A | 5/1987 | Duret et al. |
| 4,664,626 | A | 5/1987 | Kesling |
| 4,665,621 | A | 5/1987 | Ackerman et al. |
| 4,676,747 | A | 6/1987 | Kesling |
| 4,755,139 | A | 7/1988 | Abbatte et al. |
| 4,757,824 | A | 7/1988 | Chaumet |
| 4,763,791 | A | 8/1988 | Halverson et al. |
| 4,764,111 | A | 8/1988 | Knierim |
| 4,790,752 | A | 12/1988 | Cheslak |
| 4,793,803 | A | 12/1988 | Martz |
| 4,798,534 | A | 1/1989 | Breads |
| 4,836,778 | A | 6/1989 | Baumrind et al. |
| 4,837,732 | A | 6/1989 | Brandestini et al. |
| 4,850,864 | A | 7/1989 | Diamond |
| 4,850,865 | A | 7/1989 | Napolitano |
| 4,856,991 | A | 8/1989 | Breads et al. |
| 4,877,398 | A | 10/1989 | Kesling |
| 4,880,380 | A | 11/1989 | Martz |
| 4,886,451 | A | 12/1989 | Cetlin |
| 4,889,238 | A | 12/1989 | Batchelor |
| 4,890,608 | A | 1/1990 | Steer |
| 4,935,635 | A | 6/1990 | O'Harra |
| 4,936,862 | A | 6/1990 | Walker et al. |
| 4,937,928 | A | 7/1990 | van der Zel |
| 4,941,826 | A | 7/1990 | Loran et al. |
| 4,952,928 | A | 8/1990 | Carroll et al. |
| 4,964,770 | A | 10/1990 | Steinbichler et al. |
| 4,975,052 | A | 12/1990 | Spencer et al. |
| 4,983,334 | A | 1/1991 | Adell |
| 4,997,369 | A | 3/1991 | Shafir |
| 5,002,485 | A | 3/1991 | Aagesen |
| 5,011,405 | A | 4/1991 | Lemchen |
| 5,017,133 | A | 5/1991 | Miura |
| 5,027,281 | A | 6/1991 | Rekow et al. |
| 5,035,613 | A | 7/1991 | Breads et al. |
| 5,037,295 | A | 8/1991 | Bergersen |
| 5,055,039 | A | 10/1991 | Abbatte et al. |
| 5,061,839 | A | 10/1991 | Matsuno et al. |
| 5,083,919 | A | 1/1992 | Quach |
| 5,100,316 | A | 3/1992 | Wildman |
| 5,103,838 | A | 4/1992 | Yousif |
| 5,121,333 | A | 6/1992 | Riley et al. |
| 5,123,425 | A | 6/1992 | Shannon et al. |
| 5,128,870 | A | 7/1992 | Erdman et al. |
| 5,130,064 | A | 7/1992 | Smalley et al. |
| 5,131,843 | A | 7/1992 | Hilgers et al. |
| 5,131,844 | A | 7/1992 | Marinaccio et al. |
| 5,139,419 | A | 8/1992 | Andreiko et al. |
| 5,145,364 | A | 9/1992 | Martz et al. |
| 5,176,517 | A | 1/1993 | Truax |
| 5,194,003 | A | 3/1993 | Garay et al. |
| 5,204,670 | A | 4/1993 | Stinton |
| 5,222,499 | A | 6/1993 | Allen et al. |
| 5,224,049 | A | 6/1993 | Mushabac |
| 5,242,304 | A | 9/1993 | Truax et al. |
| 5,245,592 | A | 9/1993 | Kuemmel et al. |
| 5,257,203 | A * | 10/1993 | Riley ................ A61C 13/0004 700/163 |
| 5,273,429 | A | 12/1993 | Rekow et al. |
| 5,278,756 | A | 1/1994 | Lemchen et al. |
| 5,306,144 | A | 4/1994 | Hibst et al. |
| 5,328,362 | A | 7/1994 | Watson et al. |
| 5,335,657 | A | 8/1994 | Terry et al. |
| 5,338,198 | A | 8/1994 | Wu et al. |
| 5,340,309 | A | 8/1994 | Robertson |
| 5,342,202 | A | 8/1994 | Deshayes |
| 5,368,478 | A | 11/1994 | Andreiko et al. |
| 5,372,502 | A | 12/1994 | Massen et al. |
| D354,355 | S | 1/1995 | Hilgers |
| 5,382,164 | A | 1/1995 | Stern |
| 5,395,238 | A | 3/1995 | Andreiko et al. |
| 5,431,562 | A * | 7/1995 | Andreiko ................ A61C 7/00 433/24 |
| 5,440,326 | A | 8/1995 | Quinn |
| 5,440,496 | A | 8/1995 | Andersson et al. |
| 5,447,432 | A | 9/1995 | Andreiko et al. |
| 5,452,219 | A | 9/1995 | Dehoff et al. |
| 5,454,717 | A | 10/1995 | Andreiko et al. |
| 5,456,600 | A | 10/1995 | Andreiko et al. |
| 5,474,448 | A | 12/1995 | Andreiko et al. |

(56) References Cited

U.S. PATENT DOCUMENTS

| | | |
|---|---|---|
| 5,487,662 A | 1/1996 | Kipke et al. |
| RE35,169 E | 3/1996 | Lemchen et al. |
| 5,499,633 A | 3/1996 | Fenton |
| 5,522,725 A | 6/1996 | Jordan et al. |
| 5,528,735 A | 6/1996 | Strasnick et al. |
| 5,533,895 A | 7/1996 | Andreiko et al. |
| 5,540,732 A | 7/1996 | Testerman |
| 5,542,842 A | 8/1996 | Andreiko et al. |
| 5,543,780 A | 8/1996 | McAuley et al. |
| 5,549,476 A | 8/1996 | Stern |
| 5,562,448 A | 10/1996 | Mushabac |
| 5,570,182 A | 10/1996 | Nathel et al. |
| 5,583,977 A | 12/1996 | Seidl |
| 5,587,912 A | 12/1996 | Andersson et al. |
| 5,588,098 A | 12/1996 | Chen et al. |
| 5,605,459 A | 2/1997 | Kuroda et al. |
| 5,607,305 A | 3/1997 | Andersson et al. |
| 5,614,075 A | 3/1997 | Andre |
| 5,621,648 A | 4/1997 | Crump |
| 5,626,537 A | 5/1997 | Danyo et al. |
| 5,645,420 A | 7/1997 | Bergersen |
| 5,645,421 A | 7/1997 | Slootsky |
| 5,651,671 A | 7/1997 | Seay et al. |
| 5,655,653 A | 8/1997 | Chester |
| 5,659,420 A | 8/1997 | Wakai et al. |
| 5,683,243 A | 11/1997 | Andreiko et al. |
| 5,683,244 A | 11/1997 | Truax |
| 5,691,539 A | 11/1997 | Pfeiffer |
| 5,692,894 A | 12/1997 | Schwartz et al. |
| 5,711,665 A | 1/1998 | Adam et al. |
| 5,725,376 A | 3/1998 | Poirier |
| 5,725,378 A | 3/1998 | Wang |
| 5,730,151 A | 3/1998 | Summer et al. |
| 5,737,084 A | 4/1998 | Ishihara |
| 5,740,267 A | 4/1998 | Echerer et al. |
| 5,742,700 A * | 4/1998 | Yoon .................. G06T 7/12 382/190 |
| 5,769,631 A | 6/1998 | Williams |
| 5,774,425 A | 6/1998 | Ivanov et al. |
| 5,790,242 A | 8/1998 | Stern et al. |
| 5,799,100 A | 8/1998 | Clarke et al. |
| 5,800,174 A | 9/1998 | Andersson |
| 5,813,854 A | 9/1998 | Nikodem |
| 5,816,800 A | 10/1998 | Brehm et al. |
| 5,818,587 A | 10/1998 | Devaraj et al. |
| 5,823,778 A | 10/1998 | Schmitt et al. |
| 5,848,115 A | 12/1998 | Little et al. |
| 5,857,853 A | 1/1999 | van Nifterick et al. |
| 5,866,058 A | 2/1999 | Batchelder et al. |
| 5,879,158 A | 3/1999 | Doyle et al. |
| 5,880,961 A | 3/1999 | Crump |
| 5,880,962 A | 3/1999 | Andersson et al. |
| 5,882,192 A * | 3/1999 | Bergersen .............. A61C 7/00 433/2 |
| 5,886,702 A | 3/1999 | Migdal et al. |
| 5,890,896 A | 4/1999 | Padial |
| 5,904,479 A | 5/1999 | Staples |
| 5,934,288 A | 8/1999 | Avila et al. |
| 5,957,686 A | 9/1999 | Anthony |
| 5,964,587 A | 10/1999 | Sato |
| 5,971,754 A | 10/1999 | Sondhi et al. |
| 5,975,893 A | 11/1999 | Chishti et al. |
| 5,975,906 A | 11/1999 | Knutson |
| 5,980,246 A | 11/1999 | Ramsay et al. |
| 5,989,023 A | 11/1999 | Summer et al. |
| 6,002,706 A | 12/1999 | Staver et al. |
| 6,015,289 A * | 1/2000 | Andreiko ............... A61C 7/00 433/3 |
| 6,044,309 A | 3/2000 | Honda |
| 6,049,743 A | 4/2000 | Baba |
| 6,053,731 A | 4/2000 | Heckenberger |
| 6,068,482 A | 5/2000 | Snow |
| 6,070,140 A | 5/2000 | Tran |
| 6,099,303 A | 8/2000 | Gibbs et al. |
| 6,099,314 A | 8/2000 | Kopelman et al. |
| 6,123,544 A | 9/2000 | Cleary |
| 6,152,731 A | 11/2000 | Jordan et al. |
| 6,154,676 A | 11/2000 | Levine |
| 6,183,248 B1 | 2/2001 | Chishti et al. |
| 6,183,249 B1 | 2/2001 | Brennan et al. |
| 6,186,780 B1 | 2/2001 | Hibst et al. |
| 6,190,165 B1 | 2/2001 | Andreiko et al. |
| 6,200,133 B1 | 3/2001 | Kittelsen |
| 6,201,880 B1 | 3/2001 | Elbaum et al. |
| 6,212,435 B1 | 4/2001 | Lattner et al. |
| 6,217,334 B1 | 4/2001 | Hultgren |
| 6,227,850 B1 | 5/2001 | Chishti et al. |
| 6,231,338 B1 | 5/2001 | de Josselin de Jong et al. |
| 6,239,705 B1 | 5/2001 | Glen |
| 6,243,601 B1 | 6/2001 | Wist |
| 6,263,234 B1 | 7/2001 | Engelhardt et al. |
| 6,283,761 B1 | 9/2001 | Joao |
| 6,299,438 B1 | 10/2001 | Sahagian et al. |
| 6,309,215 B1 | 10/2001 | Phan et al. |
| 6,313,432 B1 | 11/2001 | Nagata et al. |
| 6,315,553 B1 | 11/2001 | Sachdeva et al. |
| 6,328,745 B1 | 12/2001 | Ascherman |
| 6,334,073 B1 | 12/2001 | Levine |
| 6,350,120 B1 | 2/2002 | Sachdeva et al. |
| 6,364,660 B1 | 4/2002 | Durbin et al. |
| 6,382,975 B1 | 5/2002 | Poirier |
| 6,386,878 B1 | 5/2002 | Pavlovskaia et al. |
| 6,402,510 B1 | 6/2002 | Williams |
| 6,402,707 B1 | 6/2002 | Ernst |
| 6,405,729 B1 | 6/2002 | Thornton |
| 6,406,292 B1 | 6/2002 | Chishti et al. |
| 6,409,504 B1 | 6/2002 | Jones et al. |
| 6,413,086 B1 | 7/2002 | Womack |
| 6,414,264 B1 | 7/2002 | von Falkenhausen |
| 6,414,708 B1 | 7/2002 | Carmeli et al. |
| 6,436,058 B1 | 8/2002 | Krahner et al. |
| 6,450,167 B1 | 9/2002 | David et al. |
| 6,450,807 B1 | 9/2002 | Chishti et al. |
| 6,462,301 B1 | 10/2002 | Scott et al. |
| 6,471,511 B1 | 10/2002 | Chishti et al. |
| 6,471,512 B1 | 10/2002 | Sachdeva et al. |
| 6,471,970 B1 | 10/2002 | Fanara et al. |
| 6,482,002 B2 | 11/2002 | Jordan et al. |
| 6,482,298 B1 | 11/2002 | Bhatnagar |
| 6,496,814 B1 | 12/2002 | Busche |
| 6,496,816 B1 | 12/2002 | Thiesson et al. |
| 6,499,026 B1 | 12/2002 | Rivette et al. |
| 6,499,995 B1 | 12/2002 | Schwartz |
| 6,507,832 B1 | 1/2003 | Evans et al. |
| 6,514,074 B1 | 2/2003 | Chishti et al. |
| 6,515,593 B1 | 2/2003 | Stark et al. |
| 6,516,288 B2 | 2/2003 | Bagne |
| 6,516,805 B1 | 2/2003 | Thornton |
| 6,520,772 B2 | 2/2003 | Williams |
| 6,523,019 B1 | 2/2003 | Borthwick |
| 6,524,101 B1 | 2/2003 | Phan et al. |
| 6,526,168 B1 | 2/2003 | Ornes et al. |
| 6,529,891 B1 | 3/2003 | Heckerman |
| 6,529,902 B1 | 3/2003 | Kanevsky et al. |
| 6,532,455 B1 | 3/2003 | Martin et al. |
| 6,535,865 B1 | 3/2003 | Skaaning et al. |
| 6,540,512 B1 | 4/2003 | Sachdeva et al. |
| 6,540,707 B1 | 4/2003 | Stark et al. |
| 6,542,593 B1 | 4/2003 | Bowman Amuah |
| 6,542,881 B1 | 4/2003 | Meidan et al. |
| 6,542,894 B1 | 4/2003 | Lee et al. |
| 6,542,903 B2 | 4/2003 | Hull et al. |
| 6,551,243 B2 | 4/2003 | Bocionek et al. |
| 6,556,659 B1 | 4/2003 | Bowman Amuah |
| 6,556,977 B1 | 4/2003 | Lapointe et al. |
| 6,560,592 B1 | 5/2003 | Reid et al. |
| 6,564,209 B1 | 5/2003 | Dempski et al. |
| 6,567,814 B1 | 5/2003 | Bankier et al. |
| 6,571,227 B1 | 5/2003 | Agrafiotis et al. |
| 6,572,372 B1 | 6/2003 | Phan et al. |
| 6,573,998 B2 | 6/2003 | Cohen Sabban |
| 6,574,561 B2 | 6/2003 | Alexander et al. |
| 6,578,003 B1 | 6/2003 | Camarda et al. |
| 6,580,948 B2 | 6/2003 | Haupert et al. |

(56) References Cited

U.S. PATENT DOCUMENTS

| | | |
|---|---|---|
| 6,582,225 B1 * | 6/2003 | Bergersen ............... A61C 7/00 433/2 |
| 6,587,529 B1 | 7/2003 | Staszewski et al. |
| 6,587,828 B1 | 7/2003 | Sachdeva |
| 6,594,539 B1 | 7/2003 | Geng |
| 6,595,342 B1 | 7/2003 | Maritzen et al. |
| 6,597,934 B1 | 7/2003 | de Jong et al. |
| 6,598,043 B1 | 7/2003 | Baclawski |
| 6,599,250 B2 | 7/2003 | Webb et al. |
| 6,602,070 B2 | 8/2003 | Miller et al. |
| 6,604,527 B1 | 8/2003 | Palmisano |
| 6,606,744 B1 | 8/2003 | Mikurak |
| 6,607,382 B1 | 8/2003 | Kuo et al. |
| 6,611,783 B2 | 8/2003 | Kelly et al. |
| 6,611,867 B1 | 8/2003 | Bowman Amuah |
| 6,613,001 B1 | 9/2003 | Dworkin |
| 6,615,158 B2 | 9/2003 | Wenzel et al. |
| 6,616,447 B1 | 9/2003 | Rizoiu et al. |
| 6,616,579 B1 | 9/2003 | Reinbold et al. |
| 6,621,491 B1 | 9/2003 | Baumrind et al. |
| 6,623,698 B2 | 9/2003 | Kuo |
| 6,624,752 B2 | 9/2003 | Klitsgaard et al. |
| 6,626,180 B1 | 9/2003 | Kittelsen et al. |
| 6,626,569 B2 | 9/2003 | Reinstein et al. |
| 6,626,669 B2 | 9/2003 | Zegarelli |
| 6,633,772 B2 | 10/2003 | Ford et al. |
| 6,640,128 B2 | 10/2003 | Vilsmeier et al. |
| 6,643,646 B2 | 11/2003 | Su et al. |
| 6,647,383 B1 | 11/2003 | August et al. |
| 6,650,944 B2 | 11/2003 | Goedeke et al. |
| 6,671,818 B1 | 12/2003 | Mikurak |
| 6,675,104 B2 | 1/2004 | Paulse et al. |
| 6,678,669 B2 | 1/2004 | Lapointe et al. |
| 6,685,469 B2 | 2/2004 | Chishti et al. |
| 6,689,055 B1 | 2/2004 | Mullen et al. |
| 6,690,761 B2 | 2/2004 | Lang et al. |
| 6,691,110 B2 | 2/2004 | Wang et al. |
| 6,694,234 B2 | 2/2004 | Lockwood et al. |
| 6,697,164 B1 | 2/2004 | Babayoff et al. |
| 6,697,793 B2 | 2/2004 | McGreevy |
| 6,702,765 B2 | 3/2004 | Robbins et al. |
| 6,702,804 B1 | 3/2004 | Ritter et al. |
| 6,705,863 B2 | 3/2004 | Phan et al. |
| 6,729,876 B2 | 5/2004 | Chishti et al. |
| 6,733,289 B2 | 5/2004 | Manemann et al. |
| 6,739,869 B1 | 5/2004 | Taub et al. |
| 6,744,932 B1 | 6/2004 | Rubbert et al. |
| 6,749,414 B1 | 6/2004 | Hanson et al. |
| 6,790,036 B2 | 9/2004 | Graham |
| 6,830,450 B2 | 12/2004 | Knopp et al. |
| 6,832,912 B2 | 12/2004 | Mao |
| 6,845,175 B2 | 1/2005 | Kopelman et al. |
| 6,885,464 B1 | 4/2005 | Pfeiffer et al. |
| 6,890,285 B2 | 5/2005 | Rahman et al. |
| 6,951,254 B2 | 10/2005 | Morrison |
| 6,984,128 B2 | 1/2006 | Breining et al. |
| 7,036,514 B2 | 5/2006 | Heck |
| 7,040,896 B2 | 5/2006 | Pavlovskaia et al. |
| 7,106,233 B2 | 9/2006 | Schroeder et al. |
| 7,112,065 B2 | 9/2006 | Kopelman et al. |
| 7,121,825 B2 | 10/2006 | Chishti et al. |
| 7,134,874 B2 | 11/2006 | Chishti et al. |
| 7,137,812 B2 | 11/2006 | Cleary et al. |
| 7,138,640 B1 | 11/2006 | Delgado et al. |
| 7,140,877 B2 | 11/2006 | Kaza |
| 7,142,312 B2 | 11/2006 | Quadling et al. |
| 7,155,373 B2 | 12/2006 | Jordan et al. |
| 7,156,655 B2 | 1/2007 | Sachdeva et al. |
| 7,156,661 B2 | 1/2007 | Choi et al. |
| 7,166,063 B2 | 1/2007 | Rahman et al. |
| 7,184,150 B2 | 2/2007 | Quadling et al. |
| 7,192,273 B2 | 3/2007 | McSurdy |
| 7,220,122 B2 | 5/2007 | Chishti |
| 7,220,124 B2 | 5/2007 | Taub et al. |
| 7,234,937 B2 | 6/2007 | Sachdeva et al. |
| 7,241,142 B2 | 7/2007 | Abolfathi et al. |
| 7,244,230 B2 | 7/2007 | Duggirala et al. |
| 7,257,136 B2 | 8/2007 | Mori et al. |
| 7,286,954 B2 | 10/2007 | Kopelman et al. |
| 7,292,759 B2 | 11/2007 | Boutoussov et al. |
| 7,302,842 B2 | 12/2007 | Biester et al. |
| 7,328,706 B2 | 2/2008 | Barach et al. |
| 7,329,122 B1 | 2/2008 | Scott |
| 7,338,327 B2 | 3/2008 | Sticker et al. |
| D565,509 S | 4/2008 | Fechner et al. |
| 7,351,116 B2 | 4/2008 | Dold |
| 7,357,637 B2 | 4/2008 | Liechtung |
| 7,435,083 B2 | 10/2008 | Chishti et al. |
| 7,450,231 B2 | 11/2008 | Johs et al. |
| 7,458,810 B2 | 12/2008 | Bergersen |
| 7,460,230 B2 | 12/2008 | Johs et al. |
| 7,462,076 B2 | 12/2008 | Walter et al. |
| 7,463,929 B2 | 12/2008 | Simmons |
| 7,476,100 B2 | 1/2009 | Kuo |
| 7,500,851 B2 | 3/2009 | Williams |
| D594,413 S | 6/2009 | Palka et al. |
| 7,544,103 B2 | 6/2009 | Walter et al. |
| 7,553,157 B2 | 6/2009 | Abolfathi et al. |
| 7,561,273 B2 | 7/2009 | Stautmeister et al. |
| 7,577,284 B2 | 8/2009 | Wong et al. |
| 7,596,253 B2 | 9/2009 | Wong et al. |
| 7,597,594 B2 | 10/2009 | Stadler et al. |
| 7,609,875 B2 | 10/2009 | Liu et al. |
| D603,796 S | 11/2009 | Sticker et al. |
| 7,616,319 B1 | 11/2009 | Woollam et al. |
| 7,626,705 B2 | 12/2009 | Altendorf |
| 7,632,216 B2 | 12/2009 | Rahman et al. |
| 7,633,625 B1 | 12/2009 | Woollam et al. |
| 7,637,262 B2 | 12/2009 | Bailey |
| 7,668,355 B2 | 2/2010 | Wong et al. |
| 7,670,179 B2 | 3/2010 | Müller |
| 7,695,327 B2 | 4/2010 | Bäuerle et al. |
| 7,698,068 B2 | 4/2010 | Babayoff |
| 7,711,447 B2 | 5/2010 | Lu et al. |
| 7,724,378 B2 | 5/2010 | Babayoff |
| D618,619 S | 6/2010 | Walter |
| 7,728,848 B2 | 6/2010 | Petrov et al. |
| 7,731,508 B2 | 6/2010 | Borst |
| 7,735,217 B2 | 6/2010 | Borst |
| 7,746,339 B2 | 6/2010 | Matov et al. |
| 7,780,460 B2 | 8/2010 | Walter |
| 7,787,132 B2 | 8/2010 | Körner et al. |
| 7,791,810 B2 | 9/2010 | Powell |
| 7,796,243 B2 | 9/2010 | Choo-Smith et al. |
| 7,806,687 B2 | 10/2010 | Minagi et al. |
| 7,806,727 B2 | 10/2010 | Dold et al. |
| 7,813,787 B2 | 10/2010 | de Josselin de Jong et al. |
| 7,824,180 B2 | 11/2010 | Abolfathi et al. |
| 7,828,601 B2 | 11/2010 | Pyczak |
| 7,845,969 B2 | 12/2010 | Stadler et al. |
| 7,854,609 B2 | 12/2010 | Chen et al. |
| 7,862,336 B2 | 1/2011 | Kopelman et al. |
| 7,872,760 B2 | 1/2011 | Ertl |
| 7,874,836 B2 | 1/2011 | McSurdy |
| 7,874,849 B2 | 1/2011 | Sticker et al. |
| 7,878,801 B2 | 2/2011 | Abolfathi et al. |
| 7,880,751 B2 | 2/2011 | Kuo et al. |
| 7,892,474 B2 | 2/2011 | Shkolnik et al. |
| 7,904,308 B2 | 3/2011 | Arnone et al. |
| 7,907,280 B2 | 3/2011 | Johs et al. |
| 7,929,151 B2 | 4/2011 | Liang et al. |
| 7,930,189 B2 | 4/2011 | Kuo |
| 7,947,508 B2 | 5/2011 | Tricca et al. |
| 7,959,308 B2 | 6/2011 | Freeman et al. |
| 7,963,766 B2 | 6/2011 | Cronauer |
| 7,986,415 B2 | 7/2011 | Thiel et al. |
| 7,987,099 B2 | 7/2011 | Kuo et al. |
| 7,991,485 B2 | 8/2011 | Zakim |
| 8,017,891 B2 | 9/2011 | Nevin |
| 8,026,916 B2 | 9/2011 | Wen |
| 8,027,709 B2 | 9/2011 | Arnone et al. |
| 8,038,444 B2 | 10/2011 | Kitching et al. |
| 8,045,772 B2 | 10/2011 | Kosuge et al. |
| 8,054,556 B2 | 11/2011 | Chen et al. |

(56) References Cited

U.S. PATENT DOCUMENTS

| | | |
|---|---|---|
| 8,070,490 B1 | 12/2011 | Roetzer et al. |
| 8,077,949 B2 | 12/2011 | Liang et al. |
| 8,083,556 B2 | 12/2011 | Stadler et al. |
| D652,799 S | 1/2012 | Mueller |
| 8,099,305 B2 | 1/2012 | Kuo et al. |
| 8,118,592 B2 | 2/2012 | Tortorici |
| 8,126,025 B2 | 2/2012 | Takeda |
| 8,144,954 B2 | 3/2012 | Quadling et al. |
| 8,160,334 B2 | 4/2012 | Thiel et al. |
| 8,172,569 B2 | 5/2012 | Matty et al. |
| 8,201,560 B2 | 6/2012 | Dembro |
| 8,215,312 B2 | 7/2012 | Garabadian et al. |
| 8,240,018 B2 | 8/2012 | Walter et al. |
| 8,279,450 B2 | 10/2012 | Oota et al. |
| 8,292,617 B2 | 10/2012 | Brandt et al. |
| 8,294,657 B2 | 10/2012 | Kim et al. |
| 8,296,952 B2 | 10/2012 | Greenberg |
| 8,297,286 B2 | 10/2012 | Smernoff |
| 8,306,608 B2 | 11/2012 | Mandelis et al. |
| 8,314,764 B2 | 11/2012 | Kim et al. |
| 8,332,015 B2 | 12/2012 | Ertl |
| 8,354,588 B2 | 1/2013 | Sticker et al. |
| 8,366,479 B2 | 2/2013 | Borst et al. |
| 8,433,083 B2 | 4/2013 | Abolfathi et al. |
| 8,465,280 B2 | 6/2013 | Sachdeva et al. |
| 8,477,320 B2 | 7/2013 | Stock et al. |
| 8,488,113 B2 | 7/2013 | Thiel et al. |
| 8,520,922 B2 | 8/2013 | Wang et al. |
| 8,520,925 B2 | 8/2013 | Duret et al. |
| 8,523,565 B2 | 9/2013 | Matty et al. |
| 8,556,625 B2 | 10/2013 | Lovely |
| 8,570,530 B2 | 10/2013 | Liang |
| 8,573,224 B2 | 11/2013 | Thornton |
| 8,577,212 B2 | 11/2013 | Thiel |
| 8,601,925 B1 | 12/2013 | Coto |
| 8,639,477 B2 | 1/2014 | Chelnokov et al. |
| 8,650,586 B2 | 2/2014 | Lee et al. |
| 8,675,706 B2 | 3/2014 | Seurin et al. |
| 8,723,029 B2 | 5/2014 | Pyczak et al. |
| 8,743,923 B2 | 6/2014 | Geske et al. |
| 8,767,270 B2 | 7/2014 | Curry et al. |
| 8,768,016 B2 | 7/2014 | Pan et al. |
| 8,771,149 B2 | 7/2014 | Rahman et al. |
| 8,839,476 B2 | 9/2014 | Adachi |
| 8,843,381 B2 | 9/2014 | Kuo et al. |
| 8,856,053 B2 | 10/2014 | Mah |
| 8,870,566 B2 | 10/2014 | Bergersen |
| 8,874,452 B2 | 10/2014 | Kuo |
| 8,878,905 B2 | 11/2014 | Fisker et al. |
| 8,899,976 B2 | 12/2014 | Chen et al. |
| 8,936,463 B2 | 1/2015 | Mason et al. |
| 8,948,482 B2 | 2/2015 | Levin |
| 8,956,058 B2 | 2/2015 | Rösch |
| 8,992,216 B2 | 3/2015 | Karazivan |
| 9,022,792 B2 | 5/2015 | Sticker et al. |
| 9,039,418 B1 | 5/2015 | Rubbert |
| 9,084,535 B2 | 7/2015 | Girkin et al. |
| 9,084,657 B2 | 7/2015 | Matty et al. |
| 9,108,338 B2 | 8/2015 | Sirovskiy et al. |
| 9,144,512 B2 | 9/2015 | Wagner |
| 9,192,305 B2 | 11/2015 | Levin |
| 9,204,952 B2 | 12/2015 | Lampalzer |
| 9,214,014 B2 | 12/2015 | Levin |
| 9,241,774 B2 | 1/2016 | Li et al. |
| 9,242,118 B2 | 1/2016 | Brawn |
| 9,261,358 B2 | 2/2016 | Atiya et al. |
| 9,336,336 B2 | 5/2016 | Deichmann et al. |
| 9,351,810 B2 | 5/2016 | Moon |
| 9,375,300 B2 | 6/2016 | Matov et al. |
| 9,403,238 B2 | 8/2016 | Culp |
| 9,408,743 B1 | 8/2016 | Wagner |
| 9,414,897 B2 | 8/2016 | Wu et al. |
| 9,433,476 B2 | 9/2016 | Khardekar et al. |
| 9,439,568 B2 | 9/2016 | Atiya et al. |
| 9,444,981 B2 | 9/2016 | Bellis et al. |
| 9,463,287 B1 | 10/2016 | Lorberbaum et al. |
| 9,500,635 B2 | 11/2016 | Islam |
| 9,506,808 B2 | 11/2016 | Jeon et al. |
| 9,510,918 B2 | 12/2016 | Sanchez |
| 9,545,331 B2 | 1/2017 | Ingemarsson-Matzen |
| 9,584,771 B2 | 2/2017 | Mandelis et al. |
| 9,589,329 B2 | 3/2017 | Levin |
| 9,675,430 B2 | 6/2017 | Verker et al. |
| 9,693,839 B2 | 7/2017 | Atiya et al. |
| 9,744,006 B2 | 8/2017 | Ross |
| 9,830,688 B2 | 11/2017 | Levin |
| 9,861,451 B1 | 1/2018 | Davis |
| 9,936,186 B2 | 4/2018 | Jesenko et al. |
| 10,159,541 B2 | 12/2018 | Bindayel |
| 10,195,690 B2 | 2/2019 | Culp |
| 10,231,801 B2 | 3/2019 | Korytov et al. |
| 10,238,472 B2 | 3/2019 | Levin |
| 10,258,432 B2 | 4/2019 | Webber |
| 10,390,913 B2 | 8/2019 | Sabina et al. |
| 10,421,152 B2 | 9/2019 | Culp |
| 10,517,482 B2 * | 12/2019 | Sato .................. A61B 5/4848 |
| 2001/0002310 A1 | 5/2001 | Chishti et al. |
| 2001/0038705 A1 | 11/2001 | Rubbert et al. |
| 2001/0041320 A1 | 11/2001 | Phan et al. |
| 2002/0010568 A1 | 1/2002 | Rubbert et al. |
| 2002/0015934 A1 | 2/2002 | Rubbert et al. |
| 2002/0025503 A1 | 2/2002 | Chapoulaud et al. |
| 2002/0026105 A1 | 2/2002 | Drazen |
| 2002/0028417 A1 | 3/2002 | Chapoulaud et al. |
| 2002/0064752 A1 | 5/2002 | Durbin et al. |
| 2002/0064759 A1 | 5/2002 | Durbin et al. |
| 2002/0107853 A1 | 8/2002 | Hofmann et al. |
| 2002/0180760 A1 * | 12/2002 | Rubbert .................. G16H 50/50 |
| | | 345/630 |
| 2002/0188478 A1 | 12/2002 | Breeland et al. |
| 2003/0000927 A1 | 1/2003 | Kanaya et al. |
| 2003/0009252 A1 | 1/2003 | Pavlovskaia et al. |
| 2003/0019848 A1 | 1/2003 | Nicholas et al. |
| 2003/0021453 A1 | 1/2003 | Weise et al. |
| 2003/0035061 A1 | 2/2003 | Iwaki et al. |
| 2003/0049581 A1 | 3/2003 | Deluke |
| 2003/0057192 A1 | 3/2003 | Patel |
| 2003/0068598 A1 | 4/2003 | Vallittu et al. |
| 2003/0095697 A1 | 5/2003 | Wood et al. |
| 2003/0138752 A1 * | 7/2003 | Bergersen .................. A61C 7/00 |
| | | 433/71 |
| 2003/0139834 A1 | 7/2003 | Nikolskiy et al. |
| 2003/0172043 A1 | 9/2003 | Guyon et al. |
| 2003/0190575 A1 | 10/2003 | Hilliard |
| 2003/0192867 A1 | 10/2003 | Yamazaki et al. |
| 2003/0207224 A1 | 11/2003 | Lotte |
| 2003/0215764 A1 | 11/2003 | Kopelman et al. |
| 2003/0224311 A1 | 12/2003 | Cronauer |
| 2003/0224314 A1 * | 12/2003 | Bergersen .................. A61C 7/08 |
| | | 433/6 |
| 2004/0009449 A1 | 1/2004 | Mah et al. |
| 2004/0019262 A1 | 1/2004 | Perelgut |
| 2004/0029068 A1 * | 2/2004 | Sachdeva .................. G16H 50/50 |
| | | 433/24 |
| 2004/0038168 A1 | 2/2004 | Choi et al. |
| 2004/0054304 A1 | 3/2004 | Raby |
| 2004/0054358 A1 | 3/2004 | Cox et al. |
| 2004/0058295 A1 | 3/2004 | Bergersen |
| 2004/0068199 A1 | 4/2004 | Echauz et al. |
| 2004/0078222 A1 | 4/2004 | Khan et al. |
| 2004/0094165 A1 | 5/2004 | Cook |
| 2004/0133083 A1 | 7/2004 | Comaniciu et al. |
| 2004/0158194 A1 | 8/2004 | Wolff et al. |
| 2004/0167646 A1 | 8/2004 | Jelonek et al. |
| 2004/0193036 A1 | 9/2004 | Zhou et al. |
| 2004/0197728 A1 | 10/2004 | Abolfathi et al. |
| 2004/0214128 A1 | 10/2004 | Sachdeva et al. |
| 2004/0220691 A1 | 11/2004 | Hofmeister et al. |
| 2004/0259049 A1 | 12/2004 | Kopelman et al. |
| 2005/0003318 A1 | 1/2005 | Choi et al. |
| 2005/0023356 A1 | 2/2005 | Wiklof et al. |
| 2005/0031196 A1 | 2/2005 | Moghaddam et al. |
| 2005/0037312 A1 | 2/2005 | Uchida |
| 2005/0038669 A1 | 2/2005 | Sachdeva et al. |

(56) References Cited

U.S. PATENT DOCUMENTS

| | | |
|---|---|---|
| 2005/0048433 A1 | 3/2005 | Hilliard |
| 2005/0074717 A1 | 4/2005 | Cleary et al. |
| 2005/0100333 A1 | 5/2005 | Kerschbaumer et al. |
| 2005/0108052 A1 | 5/2005 | Omaboe |
| 2005/0171594 A1 | 8/2005 | Machan et al. |
| 2005/0171630 A1 | 8/2005 | Dinauer et al. |
| 2005/0181333 A1 | 8/2005 | Karazivan et al. |
| 2005/0186524 A1 | 8/2005 | Abolfathi et al. |
| 2005/0186526 A1 | 8/2005 | Stewart et al. |
| 2005/0233276 A1 | 10/2005 | Kopelman et al. |
| 2005/0239013 A1 | 10/2005 | Sachdeva |
| 2005/0244781 A1 | 11/2005 | Abels et al. |
| 2005/0271996 A1 | 12/2005 | Sporbert et al. |
| 2006/0056670 A1 | 3/2006 | Hamadeh |
| 2006/0057533 A1 | 3/2006 | McGann |
| 2006/0063135 A1 | 3/2006 | Mehl |
| 2006/0078842 A1 | 4/2006 | Sachdeva et al. |
| 2006/0084024 A1 | 4/2006 | Farrell |
| 2006/0098007 A1 | 5/2006 | Rouet et al. |
| 2006/0099546 A1 | 5/2006 | Bergersen |
| 2006/0111631 A1 | 5/2006 | Kelliher et al. |
| 2006/0115785 A1 | 6/2006 | Li et al. |
| 2006/0137813 A1 | 6/2006 | Robrecht et al. |
| 2006/0147872 A1 | 7/2006 | Andreiko |
| 2006/0154198 A1 | 7/2006 | Durbin et al. |
| 2006/0179020 A1 | 8/2006 | Bradski |
| 2006/0188834 A1 | 8/2006 | Hilliard |
| 2006/0199153 A1 | 9/2006 | Liu et al. |
| 2006/0223022 A1 | 10/2006 | Solomon |
| 2006/0223032 A1 | 10/2006 | Fried et al. |
| 2006/0223342 A1 | 10/2006 | Borst et al. |
| 2006/0234179 A1 | 10/2006 | Wen et al. |
| 2006/0257815 A1 | 11/2006 | De Dominicis |
| 2006/0275729 A1 | 12/2006 | Fornoff |
| 2006/0275736 A1 | 12/2006 | Wen et al. |
| 2006/0290693 A1 | 12/2006 | Zhou et al. |
| 2007/0031775 A1 | 2/2007 | Andreiko |
| 2007/0036441 A1 | 2/2007 | Handley et al. |
| 2007/0046865 A1 | 3/2007 | Umeda et al. |
| 2007/0053048 A1 | 3/2007 | Kumar et al. |
| 2007/0087300 A1 | 4/2007 | Willison et al. |
| 2007/0106138 A1 | 5/2007 | Beiski et al. |
| 2007/0141526 A1 | 6/2007 | Eisenberg et al. |
| 2007/0168152 A1 | 7/2007 | Matov et al. |
| 2007/0172112 A1 | 7/2007 | Paley et al. |
| 2007/0184402 A1 | 8/2007 | Boutoussov et al. |
| 2007/0199929 A1 | 8/2007 | Rippl et al. |
| 2007/0215582 A1 | 9/2007 | Roeper et al. |
| 2007/0231765 A1 | 10/2007 | Phan et al. |
| 2007/0238065 A1 | 10/2007 | Sherwood et al. |
| 2007/0239488 A1 | 10/2007 | DeRosso |
| 2008/0020350 A1 | 1/2008 | Matov et al. |
| 2008/0045053 A1 | 2/2008 | Stadler et al. |
| 2008/0057461 A1 | 3/2008 | Cheng et al. |
| 2008/0057479 A1 | 3/2008 | Grenness |
| 2008/0090208 A1 | 4/2008 | Rubbert |
| 2008/0094389 A1 | 4/2008 | Rouet et al. |
| 2008/0115791 A1 | 5/2008 | Heine |
| 2008/0171934 A1 | 7/2008 | Greenan et al. |
| 2008/0176448 A1 | 7/2008 | Muller et al. |
| 2008/0233530 A1 | 9/2008 | Cinader |
| 2008/0242144 A1 | 10/2008 | Dietz |
| 2008/0268400 A1 | 10/2008 | Moss et al. |
| 2009/0030290 A1 | 1/2009 | Kozuch et al. |
| 2009/0030347 A1 | 1/2009 | Cao |
| 2009/0040740 A1 | 2/2009 | Muller et al. |
| 2009/0061379 A1 | 3/2009 | Yamamoto et al. |
| 2009/0061381 A1 | 3/2009 | Durbin et al. |
| 2009/0075228 A1 | 3/2009 | Kumada et al. |
| 2009/0087050 A1 | 4/2009 | Gandyra |
| 2009/0098502 A1 | 4/2009 | Andreiko |
| 2009/0103579 A1 | 4/2009 | Ushimaru et al. |
| 2009/0105523 A1 | 4/2009 | Kassayan et al. |
| 2009/0130620 A1 | 5/2009 | Yazdi et al. |
| 2009/0136890 A1 | 5/2009 | Kang et al. |
| 2009/0136893 A1 | 5/2009 | Zegarelli |
| 2009/0148809 A1 | 6/2009 | Kuo et al. |
| 2009/0181346 A1 | 7/2009 | Orth |
| 2009/0210032 A1 | 8/2009 | Beiski et al. |
| 2009/0218514 A1 | 9/2009 | Klunder et al. |
| 2009/0246726 A1* | 10/2009 | Chelnokov ............ A61C 7/002 433/24 |
| 2009/0281433 A1 | 11/2009 | Saadat et al. |
| 2009/0286195 A1 | 11/2009 | Sears et al. |
| 2009/0298017 A1 | 12/2009 | Boerjes et al. |
| 2009/0305540 A1 | 12/2009 | Stadler et al. |
| 2009/0317757 A1 | 12/2009 | Lemchen |
| 2010/0019170 A1 | 1/2010 | Hart et al. |
| 2010/0045902 A1 | 2/2010 | Ikeda et al. |
| 2010/0068676 A1 | 3/2010 | Mason et al. |
| 2010/0086890 A1 | 4/2010 | Kuo |
| 2010/0142789 A1 | 6/2010 | Chang et al. |
| 2010/0145664 A1 | 6/2010 | Hultgren et al. |
| 2010/0145898 A1 | 6/2010 | Malfliet et al. |
| 2010/0152599 A1 | 6/2010 | DuHamel et al. |
| 2010/0165275 A1 | 7/2010 | Tsukamoto et al. |
| 2010/0167225 A1 | 7/2010 | Kuo |
| 2010/0193482 A1 | 8/2010 | Ow et al. |
| 2010/0216085 A1 | 8/2010 | Kopelman |
| 2010/0231577 A1 | 9/2010 | Kim et al. |
| 2010/0268363 A1 | 10/2010 | Karim et al. |
| 2010/0268515 A1 | 10/2010 | Vogt et al. |
| 2010/0280798 A1 | 11/2010 | Pattijn |
| 2010/0281370 A1 | 11/2010 | Rohaly et al. |
| 2010/0303316 A1 | 12/2010 | Bullis et al. |
| 2010/0312484 A1 | 12/2010 | DuHamel et al. |
| 2010/0327461 A1 | 12/2010 | Co et al. |
| 2011/0007920 A1 | 1/2011 | Abolfathi et al. |
| 2011/0012901 A1 | 1/2011 | Kaplanyan |
| 2011/0040706 A1 | 2/2011 | Sen et al. |
| 2011/0045428 A1 | 2/2011 | Boltunov et al. |
| 2011/0056350 A1 | 3/2011 | Gale et al. |
| 2011/0081625 A1 | 4/2011 | Fuh |
| 2011/0091832 A1 | 4/2011 | Kim et al. |
| 2011/0102549 A1 | 5/2011 | Takahashi |
| 2011/0102566 A1 | 5/2011 | Zakian et al. |
| 2011/0104630 A1 | 5/2011 | Matov et al. |
| 2011/0136072 A1 | 6/2011 | Li et al. |
| 2011/0143300 A1 | 6/2011 | Villaalba |
| 2011/0143673 A1 | 6/2011 | Landesman et al. |
| 2011/0159452 A1 | 6/2011 | Huang |
| 2011/0164810 A1 | 7/2011 | Zang et al. |
| 2011/0220623 A1 | 9/2011 | Beutler |
| 2011/0235045 A1 | 9/2011 | Koerner et al. |
| 2011/0269092 A1 | 11/2011 | Kuo et al. |
| 2011/0316994 A1 | 12/2011 | Lemchen |
| 2012/0029883 A1 | 2/2012 | Heinz et al. |
| 2012/0040311 A1 | 2/2012 | Nilsson |
| 2012/0081786 A1 | 4/2012 | Mizuyama et al. |
| 2012/0086681 A1 | 4/2012 | Kim et al. |
| 2012/0115107 A1 | 5/2012 | Adams |
| 2012/0129117 A1 | 5/2012 | McCance |
| 2012/0147912 A1 | 6/2012 | Moench et al. |
| 2012/0172678 A1 | 7/2012 | Logan et al. |
| 2012/0281293 A1 | 11/2012 | Gronenborn et al. |
| 2012/0295216 A1 | 11/2012 | Dykes et al. |
| 2012/0322025 A1 | 12/2012 | Ozawa et al. |
| 2013/0029284 A1 | 1/2013 | Teasdale |
| 2013/0081272 A1 | 4/2013 | Johnson et al. |
| 2013/0089828 A1 | 4/2013 | Borovinskih et al. |
| 2013/0095446 A1 | 4/2013 | Andreiko et al. |
| 2013/0103176 A1 | 4/2013 | Kopelman et al. |
| 2013/0110469 A1 | 5/2013 | Kopelman |
| 2013/0163627 A1 | 6/2013 | Seurin et al. |
| 2013/0201488 A1 | 8/2013 | Ishihara |
| 2013/0209952 A1 | 8/2013 | Kuo et al. |
| 2013/0235165 A1 | 9/2013 | Gharib et al. |
| 2013/0252195 A1 | 9/2013 | Popat |
| 2013/0266326 A1 | 10/2013 | Joseph et al. |
| 2013/0278396 A1 | 10/2013 | Kimmel |
| 2013/0280671 A1 | 10/2013 | Brawn et al. |
| 2013/0286174 A1 | 10/2013 | Urakabe |
| 2013/0293824 A1 | 11/2013 | Yoneyama et al. |
| 2013/0323664 A1 | 12/2013 | Parker |

(56) References Cited

U.S. PATENT DOCUMENTS

| | | |
|---|---|---|
| 2013/0323671 A1 | 12/2013 | Dillon et al. |
| 2013/0323674 A1 | 12/2013 | Hakomori et al. |
| 2013/0337412 A1 | 12/2013 | Kwon |
| 2014/0037180 A1* | 2/2014 | Wang .................. A61B 6/5217 382/132 |
| 2014/0061974 A1 | 3/2014 | Tyler |
| 2014/0081091 A1 | 3/2014 | Abolfathi et al. |
| 2014/0093160 A1 | 4/2014 | Porikli et al. |
| 2014/0106289 A1 | 4/2014 | Kozlowski |
| 2014/0122027 A1 | 5/2014 | Andreiko et al. |
| 2014/0142902 A1 | 5/2014 | Chelnokov et al. |
| 2014/0265034 A1 | 9/2014 | Dudley |
| 2014/0272774 A1 | 9/2014 | Dillon et al. |
| 2014/0294273 A1 | 10/2014 | Jaisson |
| 2014/0313299 A1 | 10/2014 | Gebhardt et al. |
| 2014/0329194 A1 | 11/2014 | Sachdeva et al. |
| 2014/0350354 A1 | 11/2014 | Stenzler et al. |
| 2014/0363778 A1 | 12/2014 | Parker |
| 2015/0002649 A1 | 1/2015 | Nowak et al. |
| 2015/0021210 A1 | 1/2015 | Kesling |
| 2015/0079531 A1 | 3/2015 | Heine |
| 2015/0094564 A1 | 4/2015 | Tashman et al. |
| 2015/0097315 A1 | 4/2015 | DeSimone et al. |
| 2015/0097316 A1 | 4/2015 | DeSimone et al. |
| 2015/0102532 A1 | 4/2015 | DeSimone et al. |
| 2015/0132708 A1 | 5/2015 | Kuo |
| 2015/0140502 A1 | 5/2015 | Brawn et al. |
| 2015/0150501 A1 | 6/2015 | George et al. |
| 2015/0164335 A1 | 6/2015 | Van Der Poel et al. |
| 2015/0173856 A1 | 6/2015 | Lowe et al. |
| 2015/0216626 A1 | 8/2015 | Ranjbar |
| 2015/0230885 A1 | 8/2015 | Wucher |
| 2015/0238280 A1 | 8/2015 | Wu et al. |
| 2015/0238283 A1 | 8/2015 | Tanugula et al. |
| 2015/0306486 A1 | 10/2015 | Logan et al. |
| 2015/0320320 A1 | 11/2015 | Kopelman et al. |
| 2015/0320532 A1 | 11/2015 | Matty et al. |
| 2015/0325044 A1 | 11/2015 | Lebovitz |
| 2015/0338209 A1 | 11/2015 | Knüttel |
| 2015/0342545 A1 | 12/2015 | Bergersen |
| 2015/0374469 A1 | 12/2015 | Konno et al. |
| 2016/0000332 A1 | 1/2016 | Atiya et al. |
| 2016/0003610 A1 | 1/2016 | Lampert et al. |
| 2016/0042509 A1 | 2/2016 | Andreiko et al. |
| 2016/0051345 A1 | 2/2016 | Levin |
| 2016/0064898 A1 | 3/2016 | Atiya et al. |
| 2016/0067013 A1 | 3/2016 | Morton et al. |
| 2016/0081768 A1 | 3/2016 | Kopelman et al. |
| 2016/0081769 A1 | 3/2016 | Kimura et al. |
| 2016/0095668 A1 | 4/2016 | Kuo et al. |
| 2016/0120621 A1 | 5/2016 | Li et al. |
| 2016/0135924 A1* | 5/2016 | Choi .................. A61C 7/08 433/2 |
| 2016/0135925 A1 | 5/2016 | Mason et al. |
| 2016/0163115 A1 | 6/2016 | Furst |
| 2016/0217708 A1 | 7/2016 | Levin et al. |
| 2016/0225151 A1 | 8/2016 | Cocco et al. |
| 2016/0228213 A1 | 8/2016 | Tod et al. |
| 2016/0242871 A1 | 8/2016 | Morton et al. |
| 2016/0246936 A1 | 8/2016 | Kahn |
| 2016/0287358 A1 | 10/2016 | Nowak et al. |
| 2016/0296303 A1 | 10/2016 | Parker |
| 2016/0328843 A1 | 11/2016 | Graham et al. |
| 2016/0338799 A1 | 11/2016 | Wu et al. |
| 2016/0346063 A1 | 12/2016 | Schulhof et al. |
| 2017/0007365 A1 | 1/2017 | Kopelman et al. |
| 2017/0007366 A1 | 1/2017 | Kopelman et al. |
| 2017/0007367 A1 | 1/2017 | Li et al. |
| 2017/0007368 A1 | 1/2017 | Boronkay |
| 2017/0020633 A1 | 1/2017 | Stone-Collonge et al. |
| 2017/0049311 A1 | 2/2017 | Borovinskih et al. |
| 2017/0049326 A1 | 2/2017 | Alfano et al. |
| 2017/0056131 A1 | 3/2017 | Alauddin et al. |
| 2017/0071705 A1 | 3/2017 | Kuo |
| 2017/0100209 A1 | 4/2017 | Wen |
| 2017/0100212 A1 | 4/2017 | Sherwood et al. |
| 2017/0100213 A1 | 4/2017 | Kuo |
| 2017/0100214 A1 | 4/2017 | Wen |
| 2017/0105815 A1 | 4/2017 | Matov et al. |
| 2017/0135792 A1 | 5/2017 | Webber |
| 2017/0135793 A1 | 5/2017 | Webber et al. |
| 2017/0156821 A1 | 6/2017 | Kopelman et al. |
| 2017/0165032 A1 | 6/2017 | Webber et al. |
| 2017/0169562 A1* | 6/2017 | Somasundaram ... G06V 20/653 |
| 2017/0215739 A1 | 8/2017 | Miyasato |
| 2017/0251954 A1 | 9/2017 | Lotan et al. |
| 2017/0265970 A1 | 9/2017 | Verker |
| 2017/0319054 A1 | 11/2017 | Miller et al. |
| 2017/0319296 A1 | 11/2017 | Webber et al. |
| 2017/0325689 A1* | 11/2017 | Salah .................. A61B 5/4547 |
| 2017/0325690 A1 | 11/2017 | Salah et al. |
| 2017/0340411 A1 | 11/2017 | Akselrod |
| 2018/0000563 A1 | 1/2018 | Shanjani et al. |
| 2018/0000565 A1 | 1/2018 | Shanjani et al. |
| 2018/0028063 A1 | 2/2018 | Elbaz et al. |
| 2018/0028064 A1 | 2/2018 | Elbaz et al. |
| 2018/0028065 A1 | 2/2018 | Elbaz et al. |
| 2018/0055602 A1 | 3/2018 | Kopelman et al. |
| 2018/0071054 A1 | 3/2018 | Ha |
| 2018/0085059 A1 | 3/2018 | Lee |
| 2018/0096465 A1 | 4/2018 | Levin |
| 2018/0125610 A1 | 5/2018 | Carrier et al. |
| 2018/0153648 A1 | 6/2018 | Shanjani et al. |
| 2018/0153649 A1 | 6/2018 | Wu et al. |
| 2018/0153733 A1 | 6/2018 | Kuo |
| 2018/0168788 A1 | 6/2018 | Fernie |
| 2018/0192877 A1 | 7/2018 | Atiya et al. |
| 2019/0026599 A1* | 1/2019 | Salah .................. G06T 7/11 |
| 2019/0046297 A1 | 2/2019 | Kopelman et al. |
| 2019/0076216 A1 | 3/2019 | Moss et al. |
| 2019/0090983 A1 | 3/2019 | Webber et al. |
| 2019/0125494 A1 | 5/2019 | Li et al. |
| 2019/0152152 A1 | 5/2019 | O'Leary et al. |
| 2019/0192259 A1 | 6/2019 | Kopelman et al. |
| 2019/0231477 A1 | 8/2019 | Shanjani et al. |
| 2019/0231491 A1 | 8/2019 | Sabina et al. |
| 2019/0231492 A1 | 8/2019 | Sabina et al. |
| 2019/0240771 A1 | 8/2019 | Culp |
| 2019/0269482 A1 | 9/2019 | Shanjani et al. |
| 2020/0085548 A1* | 3/2020 | Reynard .................. A61B 6/032 |

FOREIGN PATENT DOCUMENTS

| | | |
|---|---|---|
| AU | 5598894 A | 6/1994 |
| CA | 1121955 A1 | 4/1982 |
| CN | 102017658 A | 4/2011 |
| CN | 105496575 A | 4/2016 |
| CN | 105997274 A | 10/2016 |
| DE | 2749802 A1 | 5/1978 |
| DE | 4207169 A1 | 9/1993 |
| DE | 69327661 T2 | 7/2000 |
| DE | 102005043627 A1 | 3/2007 |
| DE | 202010017014 U1 | 3/2011 |
| DE | 102011051443 A1 | 1/2013 |
| DE | 102014225457 A1 | 6/2016 |
| EP | 0428152 A1 | 5/1991 |
| EP | 490848 A2 | 6/1992 |
| EP | 541500 A1 | 5/1993 |
| EP | 714632 B1 | 5/1997 |
| EP | 774933 B1 | 12/2000 |
| EP | 731673 B1 | 5/2001 |
| EP | 1941843 A2 | 7/2008 |
| EP | 2437027 A2 | 4/2012 |
| EP | 2447754 A1 | 5/2012 |
| EP | 1989764 B1 | 7/2012 |
| EP | 2332221 B1 | 11/2012 |
| EP | 2596553 B1 | 12/2013 |
| EP | 2612300 B1 | 2/2015 |
| EP | 2848229 A1 | 3/2015 |
| ES | 463897 A1 | 1/1980 |
| ES | 2455066 A1 | 4/2014 |
| FR | 2369828 A1 | 6/1978 |
| FR | 2867377 A1 | 9/2005 |
| FR | 2930334 A1 | 10/2009 |

(56) References Cited

FOREIGN PATENT DOCUMENTS

| | | | |
|---|---|---|---|
| GB | 1550777 A | 8/1979 | |
| JP | 53-058191 A | 5/1978 | |
| JP | 4028359 A | 1/1992 | |
| JP | 08-508174 A | 9/1996 | |
| JP | 09-19443 A | 1/1997 | |
| JP | 2000339468 A | 9/2004 | |
| JP | 2006043121 A | 2/2006 | |
| JP | 2007260158 A | 10/2007 | |
| JP | 2008067732 A | 3/2008 | |
| JP | 2008523370 A | 7/2008 | |
| JP | 04184427 B1 | 11/2008 | |
| JP | 2009000412 A | 1/2009 | |
| JP | 2009018173 A | 1/2009 | |
| JP | 2009059123 A | 3/2009 | |
| JP | 2009078133 A | 4/2009 | |
| JP | 2009101386 A | 5/2009 | |
| JP | 2009205330 A | 9/2009 | |
| JP | 2010017726 A | 1/2010 | |
| JP | 2011087733 A | 5/2011 | |
| JP | 2012045143 A | 3/2012 | |
| JP | 2013007645 A | 1/2013 | |
| JP | 2013192865 A | 9/2013 | |
| JP | 201735173 A | 2/2017 | |
| JP | 2017035173 A | 2/2017 | |
| KR | 10-20020062793 A | 7/2002 | |
| KR | 10-20090065778 A | 6/2009 | |
| KR | 20130006030 A | 1/2013 | |
| KR | 10-1266966 B1 | 5/2013 | |
| KR | 10-2016-041632 A | 4/2016 | |
| KR | 10-2016-0071127 A | 6/2016 | |
| KR | 10-1675089 B1 | 11/2016 | |
| WO | WO91/004713 A1 | 4/1991 | |
| WO | WO94/010935 A1 | 5/1994 | |
| WO | WO98/032394 A1 | 7/1998 | |
| WO | WO98/044865 A1 | 10/1998 | |
| WO | WO02/017776 A2 | 3/2002 | |
| WO | WO02/062252 A1 | 8/2002 | |
| WO | WO02/095475 A1 | 11/2002 | |
| WO | WO03/003932 A2 | 1/2003 | |
| WO | WO2006/096558 A2 | 9/2006 | |
| WO | WO2006/100700 A1 | 9/2006 | |
| WO | WO2006/133548 A1 | 12/2006 | |
| WO | WO2007/071341 A1 | 6/2007 | |
| WO | WO2008/115654 A1 | 9/2008 | |
| WO | WO2009/016645 A2 | 2/2009 | |
| WO | WO2009/085752 A2 | 7/2009 | |
| WO | WO2009/089129 A1 | 7/2009 | |
| WO | WO2009/146788 A1 | 12/2009 | |
| WO | WO2009/146789 A1 | 12/2009 | |
| WO | WO2010/123892 A2 | 10/2010 | |
| WO | WO2012/007003 A1 | 1/2012 | |
| WO | WO2012/064684 A2 | 5/2012 | |
| WO | WO2012/074304 A2 | 6/2012 | |
| WO | WO2012/083968 A1 | 6/2012 | |
| WO | WO2012/140021 A2 | 10/2012 | |
| WO | WO2013/058879 A2 | 4/2013 | |
| WO | WO2014/068107 A1 | 5/2014 | |
| WO | WO2014/091865 A1 | 6/2014 | |
| WO | WO2015/015289 A2 | 2/2015 | |
| WO | WO2015/063032 A1 | 5/2015 | |
| WO | WO2015/112638 A1 | 7/2015 | |
| WO | WO2015/176004 A1 | 11/2015 | |
| WO | WO2016/004415 A1 | 1/2016 | |
| WO | WO2016/042393 A1 | 3/2016 | |
| WO | WO2016/061279 A1 | 4/2016 | |
| WO | WO2016/084066 A1 | 6/2016 | |
| WO | WO2016/099471 A1 | 6/2016 | |
| WO | WO2016/113745 A1 | 7/2016 | |
| WO | WO2016/116874 A1 | 7/2016 | |
| WO | WO2017/006176 A1 | 1/2017 | |
| WO | WO2017/182654 A1 | 10/2017 | |
| WO | WO-2017220619 A1 * | 12/2017 | ............. A61B 34/10 |
| WO | WO2018/057547 A1 | 3/2018 | |
| WO | WO2018/085718 A2 | 5/2018 | |
| WO | WO2018/232113 A1 | 12/2018 | |
| WO | WO2019/018784 A1 | 1/2019 | |

OTHER PUBLICATIONS

Farooq et al.; Relationship between tooth dimensions and malocclusion; JPMA: The Journal of the Pakistan Medical Association; 64(6); pp. 670-674; Jun. 2014.

Newcombe; DTAM: Dense tracking and mapping in real-time; 8 pages; retrieved from the internet (http://www.doc.ic.ac.uk/?ajd/Publications/newcombe_etal_iccv2011.pdf; on Dec. 2011.

ormco.com; Increasing clinical performance with 3D interactive treatment planning and patient-specific appliances; 8 pages; retrieved from the internet (http://www.konsident.com/wp-content/files_mf/1295385693http_ormco.com_index_cmsfilesystemaction_fileOrmcoPDF_whitepapers.pdf) on Feb. 27, 2019.

Arakawa et al; Mouthguard biosensor with telemetry system for monitoring of saliva glucose: A novel cavitas sensor; Biosensors and Bioelectronics; 84; pp. 106-111; Oct. 2016.

Sirona Dental Systems GmbH, CEREC 3D, Manuel utilisateur, Version 2.0X (in French); 114 pages; (English translation of table of contents included); (year of pub. sufficiently earlier than effective US filing date and any foreign priority date); 2003.

AADR. American Association for Dental Research; Summary of Activities; Los Angeles, CA; p. 195; Mar. 20-23,(year of pub. sufficiently earlier than effective US filing date and any foreign priority date) 1980.

Alcaniz et aL; An Advanced System for the Simulation and Planning of Orthodontic Treatments; Karl Heinz Hohne and Ron Kikinis (eds.); Visualization in Biomedical Computing, 4th Intl. Conf, VBC '96, Hamburg, Germany; Springer-Verlag; pp. 511-520; Sep. 22-25, 1996.

Alexander et al.; The DigiGraph Work Station Part 2 Clinical Management; J. Clin. Orthod.; pp. 402-407; (Author Manuscript); Jul. 1990.

Align Technology; Align technology announces new teen solution with introduction of invisalign teen with mandibular advancement; 2 pages; retrieved from the internet (http://investor.aligntech.com/static-files/eb4fa6bb-3e62-404f-b74d-32059366a01b); Mar. 6, 2017.

Allesee Orthodontic Appliance: Important Tip About Wearing the Red White & Blue Active Clear Retainer System; Allesee Orthodontic Appliances—Pro Lab; 1 page; (year of pub. sufficiently earlier than effective US filing date and any foreign priority date); 1998.

Allesee Orthodontic Appliances: DuraClearTM; Product information; 1 page; (year of pub. sufficiently earlier than effective US filing date and any foreign priority date) 1997.

Allesee Orthodontic Appliances; The Choice Is Clear: Red, White & Blue . . . The Simple, Affordable, No-Braces Treatment; ( product information for doctors); retrieved from the internet (http://ormco.com/aoa/appliancesservices/RWB/doctorhtml); 5 pages on May 19, 2003.

Allesee Orthodontic Appliances; The Choice Is Clear: Red, White & Blue . . . The Simple, Affordable, No-Braces Treatment; (product information), 6 pages; (year of pub. sufficiently earlier than effective US filing date and any foreign priority date) 2003.

Allesee Orthodontic Appliances; The Choice is Clear: Red, White & Blue . . . The Simple, Affordable, No-Braces Treatment;(Patient Information); retrieved from the internet (http://ormco.com/aoa/appliancesservices/RWB/patients.html); 2 pages on May 19, 2003.

Allesee Orthodontic Appliances; The Red, White & Blue Way to Improve Your Smile; (information for patients), 2 pages; (year of pub. sufficiently earlier than effective US filing date and any foreign priority date) 1992.

Allesee Orthodontic Appliances; You may be a candidate for this invisible no-braces treatment; product information for patients; 2 pages; (year of pub. sufficiently earlier than effective US filing date and any foreign priority date) 2002.

Altschuler et al.; Analysis of 3-D Data for Comparative 3-D Serial Growth Pattern Studies of Oral-Facial Structures; AADR Abstracts, Program and Abstracts of Papers, 57th General Session, IADR

(56) References Cited

OTHER PUBLICATIONS

Annual Session, Mar. 29, 1979-Apr. 1, 1979, New Orleans Marriot; Journal of Dental Research; vol. 58, Special Issue A, p. 221; Jan. 1979.
Altschuler et al.; Laser Electro-Optic System for Rapid Three-Dimensional (3D) Topographic Mapping of Surfaces; Optical Engineering; 20(6); pp. 953-961; Dec. 1981.
Altschuler et al.; Measuring Surfaces Space-Coded by a Laser-Projected Dot Matrix; SPIE Imaging q Applications for Automated Industrial Inspection and Assembly; vol. 182; pp. 187-191; Oct. 10, 1979.
Altschuler; 3D Mapping of Maxillo-Facial Prosthesis; AADR Abstract #607; 2 pages total, (year of pub. sufficiently earlier than effective US filing date and any foreign priority date) 1980.
Alves et al.; New trends in food allergens detection: toward biosensing strategies; Critical Reviews in Food Science and Nutrition; 56(14); pp. 2304-2319; doi: 10.1080/10408398.2013.831026; Oct. 2016.
Andersson et al.; Clinical Results with Titanium Crowns Fabricated with Machine Duplication and Spark Erosion; Acta Odontologica Scandinavica; 47(5); pp. 279-286; Oct. 1989.
Andrews, The Six Keys to Optimal Occlusion Straight Wire, Chapter 3, L.A. Wells; pp. 13-24; (year of pub. sufficiently earlier than effective US filing date and any foreign priority date) 1989.
Barone et al.; Creation of 3D multi-body orthodontic models by using independent imaging sensors; Sensors; 13(2); pp. 2033-2050; Feb. 5, 2013.
Bartels et al.; An Introduction to Splines for Use in Computer Graphics and Geometric Modeling; Morgan Kaufmann Publishers; pp. 422-425 Jan. 1, 1987.
Baumrind et al, "Mapping the Skull in 3-D," reprinted from J. Calif. Dent. Assoc, 48(2), 11 pages; (year of pub. sufficiently earlier than effective US filing date and any foreign priority date) Fall Issue 1972.
Baumrind et al.; A Stereophotogrammetric System for the Detection of Prosthesis Loosening in Total Hip Arthroplasty; NATO Symposium on Applications of Human Biostereometrics; SPIE; vol. 166; pp. 112-123; Jul. 9-13, 1978.
Baumrind; A System for Cranio facial Mapping Through the Integration of Data from Stereo X-Ray Films and Stereo Photographs; an invited paper submitted to the 1975 American Society of Photogram Symposium on Close-Range Photogram Systems; University of Illinois; pp. 142-166; Aug. 26-30, 1975.
Baumrind; Integrated Three-Dimensional Craniofacial Mapping: Background, Principles, and Perspectives; Seminars in Orthodontics; 7(4); pp. 223-232; Dec. 2001.
Begole et al.; A Computer System for the Analysis of Dental Casts; The Angle Orthodontist; 51(3); pp. 252-258; Jul. 1981.
Bernard et al; Computerized Diagnosis in Orthodontics for Epidemiological Studies: A ProgressReport; (Abstract Only), J. Dental Res. Special Issue, vol. 67, p. 169, paper presented at International Association for Dental Research 66th General Session, Montreal Canada; Mar. 9-13, 1988.
Bhatia et al.; A Computer-Aided Design for Orthognathic Surgery; British Journal of Oral and Maxillofacial Surgery; 22(4); pp. 237-253; Aug. 1, 1984.
Biggerstaff et al.; Computerized Analysis of Occlusion in the Postcanine Dentition; American Journal of Orthodontics; 61(3); pp. 245-254; Mar. 1972.
Biggerstaff; Computerized Diagnostic Setups and Simulations; Angle Orthodontist; 40(I); pp. 28-36; Jan. 1970.
Biostar Operation & Training Manual. Great Lakes Orthodontics, Ltd. 199 Fire Tower Drive, Tonawanda, New York. 14150-5890, 20 pages; (year of pub. sufficiently earlier than effective US filing date and any foreign priority date) 1990.
Blu et al.; Linear interpolation revitalized; IEEE Transactions on Image Processing; 13(5); pp. 710-719; May 2004.
Bourke, Coordinate System Transformation; 1 page; retrived from the internet (http://astronomy.swin.edu.au/ pbourke/prolection/coords) on Nov. 5, 2004; Jun. 1996.
Boyd et al.; Three Dimensional Diagnosis and Orthodontic Treatment of Complex Malocclusions With the Invisalipn Appliance; Seminars in Orthodontics; 7(4); pp. 274-293; Dec. 2001.
Brandestini et al.; Computer Machined Ceramic Inlays: In Vitro Marginal Adaptation; J. Dent. Res. Special Issue; (Abstract 305); vol. 64; p. 208; (year of pub. sufficiently earlier than effective US filing date and any foreign priority date) 1985.
Brook et al.; An Image Analysis System for the Determination of Tooth Dimensions from Study Casts: Comparison with Manual Measurements of Mesio-distal Diameter; Journal of Dental Research; 65(3); pp. 428-431; Mar. 1986.
Burstone et al.; Precision Adjustment of the Transpalatal Lingual Arch: Computer Arch Form Predetermination; American Journal of Orthodontics; 79(2);pp. 115-133; Feb. 1981.
Burstone; Dr. Charles J. Burstone on the Uses of the Computer in Orthodontic Practice (Part 1); Journal of Clinical Orthodontics; 13(7); pp. 442-453; (interview); Jul. 1979.
Burstone; Dr. Charles J. Burstone on the Uses of the Computer in Orthodontic Practice (Part 2); journal of Clinical Orthodontics; 13(8); pp. 539-551 (interview); Aug. 1979.
Cardinal Industrial Finishes; Powder Coatings; 6 pages; retrieved from the internet (http://www.cardinalpaint.com) on Aug. 25, 2000.
Carnaghan, An Alternative to Holograms for the Portrayal of Human Teeth; 4th Int'l. Conf. on Holographic Systems, Components and Applications; pp. 228-231; Sep. 15, 1993.
Chaconas et al,; The DigiGraph Work Station, Part 1, Basic Concepts; Journal of Clinical Orthodontics; 24(6); pp. 360-367; (Author Manuscript); Jun. 1990.
Chafetz et al.; Subsidence of the Femoral Prosthesis, A Stereophotogrammetric Evaluation; Clinical Orthopaedics and Related Research; No. 201; pp. 60-67; Dec. 1985.
Chiappone; Constructing the Gnathologic Setup and Positioner; Journal of Clinical Orthodontics; 14(2); pp. 121-133; Feb. 1980.
Chishti et al.; U.S. Appl. No. 60/050,342 entitled "Procedure for moving teeth using a seires of retainers," filed Jun. 20, 1997.
CSI Computerized Scanning and Imaging Facility; What is a maximum/minimum intensity projection (MIP/MinIP); 1 page; retrived from the internet (http://csi.whoi.edu/content/what-maximumminimum-intensity-projection-mipminip); Jan. 4, 2010.
Cottingham; Gnathologic Clear Plastic Positioner; American Journal of Orthodontics; 55(1); pp. 23-31; Jan. 1969.
Crawford; CAD/CAM in the Dental Office: Does It Work?; Canadian Dental Journal; 57(2); pp. 121-123 Feb. 1991.
Crawford; Computers in Dentistry: Part 1: CAD/CAM: The Computer Moves Chairside, Part 2: F. Duret A Man With a Vision, Part 3: The Computer Gives New Vision—Literally, Part 4: Bytes 'N Bites The Computer Moves From the Front Desk to the Operatory; Canadian Dental Journal; 54(9); pp. 661-666 Sep. 1988.
Crooks; CAD/CAM Comes to USC; USC Dentistry; pp. 14-17; (year of pub. sufficiently earlier than effective US filing date and any foreign priority date) Spring 1990.
Cureton; Correcting Malaligned Mandibular Incisors with Removable Retainers; Journal of Clinical Orthodontics; 30(7); pp. 390-395; Jul. 1996.
Curry et al.; Integrated Three-Dimensional Craniofacial Mapping at the Craniofacial Research InstrumentationLaboratory/University of the Pacific; Seminars in Orthodontics; 7(4); pp. 258-265; Dec. 2001.
Cutting et al.; Three-Dimensional Computer-Assisted Design of Craniofacial Surgical Procedures: Optimization and Interaction with Cephalometric and CT-Based Models; Plastic and Reconstructive Surgery; 77(6); pp. 877-885; Jun. 1986.
DCS Dental AG; The CAD/CAM 'DCS Titan System' for Production of Crowns/Bridges; DSC Production; pp. 1-7; Jan. 1992.
Defranco et al.; Three-Dimensional Large Displacement Analysis of Orthodontic Appliances; Journal of Biomechanics; 9(12); pp. 793-801; Jan. 1976.
Dental Institute University of Zurich Switzerland; Program for International Symposium on Computer Restorations: State of the Art of the CEREC—Method; 2 pages; May 1991.
Dentrac Corporation; Dentrac document; pp. 4-13; (year of pub. sufficiently earlier than effective US filing date and any foreign priority date) 1992.

(56) References Cited

OTHER PUBLICATIONS

Dent-X; Dentsim . . . Dent-x's virtual reality 3-D training simulator . . . A revolution in dental education; 6 pages; retrieved from the internet (http://www.dent-x.com/DentSim.htm); on Sep. 24, 1998.

Di Muzio et al.; Minimum intensity projection (MinIP); 6 pages; retrieved from the internet (https://radiopaedia.org/articles/minimum-intensity-projection-minip) on Sep. 6, 2018.

Doruk et al.; The role of the headgear timer in extraoral cooperation; European Journal of Orthodontics; 26; pp. 289-291; Jun. 1, 2004.

Doyle; Digital Dentistry; Computer Graphics World; pp. 50-52 and p. 54; Oct. 2000.

Dummer et al.; Computed Radiography Imaging Based on High-Density 670 nm VCSEL Arrays; International Society for Optics and Photonics; vol. 7557; p. 75570H; 7 pages; (Author Manuscript); Feb. 24, 2010.

Duret et al.; CAD/CAM Imaging in Dentistry; Current Opinion in Dentistry; 1(2); pp. 150-154; Apr. 1991.

Duret et al; CAD-CAM in Dentistry; Journal of the American Dental Association; 117(6); pp. 715-720; Nov. 1988.

Duret; The Dental CAD/CAM, General Description of the Project; Hennson International Product Brochure, 18 pages; Jan. 1986.

Duret; Vers Une Prosthese Informatisee; Tonus; 75(15); pp. 55-57; (English translation attached); 23 pages; Nov. 15, 1985.

Economides; The Microcomputer in the Orthodontic Office; Journal of Clinical Orthodontics; 13(11); pp. 767-772; Nov. 1979.

Ellias et al.; Proteomic analysis of saliva identifies potential biomarkers for orthodontic tooth movement; The Scientific World Journal; vol. 2012; Article ID 647240; dio:10.1100/2012/647240; 7 pages; (year of pub. sufficiently earlier than effective US filing date and any foreign priority date) 2012.

Elsasser; Some Observations on the History and Uses of the Kesling Positioner; American Journal of Orthodontics; 36(5); pp. 368-374; May 1, 1950.

English translation of Japanese Laid-Open Publication No. 63-11148 to inventor T. Ozukuri (Laid-Open on Jan. 18, 1998) pp. 1-7.

Faber et al.; Computerized Interactive Orthodontic Treatment Planning; American Journal of Orthodontics; 73(1); pp. 36-46; Jan. 1978.

Felton et al.; A Computerized Analysis of the Shape and Stability of Mandibular Arch Form; American Journal of Orthodontics and Dentofacial Orthopedics; 92(6); pp. 478-483; Dec. 1987.

Florez-Moreno; Time-related changes in salivary levels of the osteotropic factors sRANKL and OPG through orthodontic tooth movement; American Journal of Orthodontics and Dentofacial Orthopedics; 143(1); pp. 92-100; Jan. 2013.

Friede et al.; Accuracy of Cephalometric Prediction in Orthognathic Surgery; Journal of Oral and Maxillofacial Surgery; 45(9); pp. 754-760; Sep. 1987.

Friedrich et al; Measuring system for in vivo recording of force systems in orthodontic treatment—concept and analysis of accuracy; J. Biomech.; 32(1); pp. 81-85; (Abstract Only) Jan. 1999.

Futterling et al.; Automated Finite Element Modeling of a Human Mandible with Dental Implants; JS WSCG '98—Conference Program; 8 pages; retrieved from the Internet (https://dspace5.zcu.cz/bitstream/11025/15851/1/Strasser_98.pdf); on Aug. 21, 2018.

Gao et al.; 3-D element Generation for Multi-Connected Complex Dental and Mandibular Structure; IEEE Proceedings International Workshop in Medical Imaging and Augmented Reality; pp. 267-271; Jun. 12, 2001.

Gim-Alldent Deutschland, "Das DUX System: Die Technik," 3 pages; (English Translation Included); (year of pub. sufficiently earlier than effective US filing date and any foreign priority date); 2002.

Gottleib et al.; JCO Interviews Dr. James A. McNamura, Jr., on the Frankel Appliance: Part 2: Clinical 1-1 Management; Journal of Clinical Orthodontics; 16(6); pp. 390-407; retrieved from the internet (http://www.jco-online.com/archive/print_article.asp?Year=1982&Month=06&ArticleNum+); 21 pages; Jun. 1982.

Grayson; New Methods for Three Dimensional Analysis of Craniofacial Deformity, Symposium: Computerized Facial Imaging in Oral and Maxillofacial Surgery; American Association of Oral and Maxillofacial Surgeons; 48(8) suppl 1; pp. 5-6; Sep. 13, 1990.

Grest, Daniel; Marker-Free Human Motion Capture in Dynamic Cluttered Environments from a Single View-Point, PhD Thesis; 171 pages; Dec. 2007.

Guess et al.; Computer Treatment Estimates in Orthodontics and Orthognathic Surgery; Journal of Clinical Orthodontics; 23(4); pp. 262-268; 11 pages; (Author Manuscript); Apr. 1989.

Heaven et al.; Computer-Based Image Analysis of Artificial Root Surface Caries; Abstracts of Papers #2094; Journal of Dental Research; 70:528; (Abstract Only); Apr. 17-21, 1991.

Highbeam Research; Simulating stress put on jaw. (ANSYS Inc.'s finite element analysis software); 2 pages; retrieved from the Internet (http://static.highbeam.eom/t/toolingampproduction/november011996/simulatingstressputonfa . . . ); on Nov. 5, 2004.

Hikage; Integrated Orthodontic Management System for Virtual Three-Dimensional Computer Graphic Simulation and Optical Video Image Database for Diagnosis and Treatment Planning; Journal of Japan KA Orthodontic Society; 46(2); pp. 248-269; 56 pages; (English Translation Included); Feb. 1987.

Hoffmann et al.; Role of Cephalometry for Planning of Jaw Orthopedics and Jaw Surgery Procedures; Informatbnen, pp. 375-396; (English Abstract Included); Mar. 1991.

Hojjatie et al.; Three-Dimensional Finite Element Analysis of Glass-Ceramic Dental Crowns; Journal of Biomechanics; 23(11); pp. 1157-1166; Jan. 1990.

Huckins; CAD-CAM Generated Mandibular Model Prototype from MRI Data; AAOMS, p. 96; (Abstract Only); (year of pub. sufficiently earlier than effective US filing date and any foreign priority date) 1999.

Invisalign; You were made to move. There's never been a better time to straighten your teeth with the most advanced clear aligner in the world; Product webpage; 2 pages; retrieved from the internet (www.invisalign.com/) on Dec. 28, 2017.

JCO Interviews; Craig Andreiko , DDS, MS on the Elan and Orthos Systems; Interview by Dr. Larry W. White; Journal of Clinical Orthodontics; 28(8); pp. 459-468; 14 pages; (Author Manuscript); Aug. 1994.

JCO Interviews; Dr. Homer W. Phillips on Computers in Orthodontic Practice, Part 2; Journal of Clinical Orthodontics; 17(12); pp. 819-831; 19 pages; (Author Manuscript); Dec. 1983.

Jerrold; The Problem, Electronic Data Transmission and the Law; American Journal of Orthodontics and Dentofacial Orthopedics; 113(4); pp. 478-479; 5 pages; (Author Manuscript); Apr. 1998.

Jones et al.; An Assessment of the Fit of a Parabolic Curve to Pre- and Post-Treatment Dental Arches; British Journal of Orthodontics; 16(2); pp. 85-93; May 1989.

Kamada et.al.; Case Reports on Tooth Positioners Using LTV Vinyl Silicone Rubber; J. Nihon University School of Dentistry; 26(1); pp. 11-29; (year of pub. sufficiently earlier than effective US filing date and any foreign priority date) 1984.

Kamada et.al.; Construction of Tooth Positioners with LTV Vinyl Silicone Rubber and Some Case KJ Reports; J. Nihon University School of Dentistry; 24(1); pp. 1-27; (year of pub. sufficiently earlier than effective US filing date and any foreign priority date) 1982.

Kanazawa et al.; Three-Dimensional Measurements of the Occlusal Surfaces of Upper Molars in a Dutch Population; Journal of Dental Research; 63(11); pp. 1298-1301; Nov. 1984.

Kesling et al.; The Philosophy of the Tooth Positioning Appliance; American Journal of Orthodontics and Oral surgery; 31(6); pp. 297-304; Jun. 1945.

Kesling; Coordinating the Predetermined Pattern and Tooth Positioner with Conventional Treatment; American Journal of Orthodontics and Oral Surgery; 32(5); pp. 285-293; May 1946.

Kleeman et al.; The Speed Positioner; J. Clin. Orthod .; 30(12); pp. 673-680; Dec. 1996.

Kochanek; Interpolating Splines with Local Tension, Continuity and Bias Control; Computer Graphics; 18(3); pp. 33-41; Jan. 1, 1984.

(56) References Cited

OTHER PUBLICATIONS

Kumar et al.; Rapid maxillary expansion: A unique treatment modality in dentistry; J. Clin. Diagn. Res.; 5(4); pp. 906-911; Aug. 2011.

Kunii et al.; Articulation Simulation for an Intelligent Dental Care System; Displays; 15(3); pp. 181-188; Jul. 1994.

Kuroda et al.; Three-Dimensional Dental Cast Analyzing System Using Laser Scanning; American Journal of Orthodontics and Dentofacial Orthopedics; 110(4); pp. 365-369; Oct. 1996.

Laurendeau et al.; A Computer-Vision Technique for the Acquisition and Processing of 3-D Profiles of 7 Dental Imprints: An Application in Orthodontics; IEEE Transactions on Medical Imaging; 10(3); pp. 453-461; Sep. 1991.

Leinfelder et al.; A New Method for Generating Ceramic Restorations: a CAD-CAM System; Journal of the American Dental Association; 118(6); pp. 703-707; Jun. 1989.

Manetti et al.; Computer-Aided Cefalometry and New Mechanics in Orthodontics; Fortschr Kieferorthop; 44; pp. 370-376; 8 pages; (English Article Summary Included); (year of pub. sufficiently earlier than effective US filing date and any foreign priority date) 1983.

Mccann; Inside the ADA; J. Amer. Dent. Assoc, 118:286-294; Mar. 1989.

Mcnamara et al.; Invisible Retainers; J. Clin Orthod.; pp. 570-578; 11 pages; (Author Manuscript); Aug. 1985.

Mcnamara et al.; Orthodontic and Orthopedic Treatment in the Mixed Dentition; Needham Press; pp. 347-353; Jan. 1993.

Moermann et al, Computer Machined Adhesive Porcelain Inlays: Margin Adaptation after Fatigue Stress; IADR Abstract 339; J. Dent. Res.; 66(a):763; (Abstract Only); (year of pub. sufficiently earlier than effective US filing date and any foreign priority date) 1987.

Moles; Correcting Mild Malalignments—As Easy as One, Two, Three; AOA/Pro Corner; 11(2); 2 pages; (year of pub. sufficiently earlier than effective US filing date and any foreign priority date) 2002.

Mormann et al.; Marginale Adaptation von adhasuven Porzellaninlays in vitro; Separatdruck aus:Schweiz. Mschr. Zahnmed.; 95; pp. 1118-1129; 8 pages; (Machine Translated English Abstract); (year of pub. sufficiently earlier than effective US filing date and any foreign priority date); 1985.

Nahoum; The Vacuum Formed Dental Contour Appliance; N. Y. State Dent. J.; 30(9); pp. 385-390; Nov. 1964.

Nash; CEREC CAD/CAM Inlays: Aesthetics and Durability in a Single Appointment; Dentistry Today; 9(8); pp. 20, 22-23 and 54; Oct. 1990.

Nedelcu et al.; "Scanning Accuracy and Precision in 4 Intraoral Scanners: An In Vitro Comparison Based on 3-Dimensional Analysis"; J. Prosthet. Dent.; 112(6); pp. 1461-1471; Dec. 2014.

Nishiyama et al.; A New Construction of Tooth Repositioner by LTV Vinyl Silicone Rubber; The Journal of Nihon University School of Dentistry; 19(2); pp. 93-102 (year of pub. sufficiently earlier than effective US filing date and any foreign priority date) 1977.

Ogawa et al.; Mapping, profiling and clustering of pressure pain threshold (PPT) in edentulous oral muscosa; Journal of Dentistry; 32(3); pp. 219-228; Mar. 2004.

Ogimoto et al.; Pressure-pain threshold determination in the oral mucosa; Journal of Oral Rehabilitation; 29(7); pp. 620-626; Jul. 2002.

Paul et al.; Digital Documentation of Individual Human Jaw and Tooth Forms for Applications in Orthodontics; Oral Surgery and Forensic Medicine Proc. of the 24th Annual Conf. of the IEEE Industrial Electronics Society (IECON '98); vol. 4; pp. 2415-2418; Sep. 4, 1998.

Pinkham; Foolish Concept Propels Technology; Dentist, 3 pages , Jan./Feb. 1989.

Pinkham; Inventor's CAD/CAM May Transform Dentistry; Dentist; pp. 1 and 35, Sep. 1990.

Ponitz; Invisible retainers; Am. J. Orthod.; 59(3); pp. 266-272; Mar. 1971.

Procera Research Projects; Procera Research Projects 1993 Abstract Collection; 23 pages; (year of pub. sufficiently earlier than effective US filing date and any foreign priority date) 1993.

Proffit et al.; The first stage of comprehensive treatment alignment and leveling; Contemporary Orthodontics, 3rd Ed.; Chapter 16; Mosby Inc.; pp. 534-537; (year of pub. sufficiently earlier than effective US filing date and any foreign priority date) 2000.

Proffit et al.; The first stage of comprehensive treatment: alignment and leveling; Contemporary Orthodontics; (Second Ed.); Chapter 15, MosbyYear Book; St. Louis, Missouri; pp. 470-533 Oct. 1993.

Raintree Essix & ARS Materials, Inc., Raintree Essix, Technical Magazine Table of contents and Essix Appliances, 7 pages; retrieved from the internet (http://www.essix.com/magazine/defaulthtml) on Aug. 13, 1997.

Redmond et al.; Clinical Implications of Digital Orthodontics; American Journal of Orthodontics and Dentofacial Orthopedics; 117(2); pp. 240-242; Feb. 2000.

Rekow et al.; CAD/CAM for Dental Restorations—Some of the Curious Challenges; IEEE Transactions on Biomedical Engineering; 38(4); pp. 314-318; Apr. 1991.

Rekow et al.; Comparison of Three Data Acquisition Techniques for 3-D Tooth Surface Mapping; Annual International Conference of the IEEE Engineering in Medicine and Biology Society; 13(1); pp. 344-345 (year of pub. sufficiently earlier than effective US filing date and any foreign priority date) 1991.

Rekow; A Review of the Developments in Dental CAD/CAM Systems; Current Opinion in Dentistry; 2; pp. 25-33; Jun. 1992.

Rekow; CAD/CAM in Dentistry: A Historical Perspective and View of the Future; Journal Canadian Dental Association; 58(4); pp. 283, 287-288; Apr. 1992.

Rekow; Computer-Aided Design and Manufacturing in Dentistry: A Review of the State of the Art; Journal of Prosthetic Dentistry; 58(4); pp. 512-516; Dec. 1987.

Rekow; Dental CAD-CAM Systems: What is the State of the Art?; The Journal of the American Dental Association; 122(12); pp. 43-48; Dec. 1991.

Rekow; Feasibility of an Automated System for Production of Dental Restorations, Ph.D. Thesis; Univ. of Minnesota, 250 pages, Nov. 1988.

Richmond et al.; The Development of the PAR Index (Peer Assessment Rating): Reliability and Validity.; The European Journal of Orthodontics; 14(2); pp. 125-139; Apr. 1992.

Richmond et al.; The Development of a 3D Cast Analysis System; British Journal of Orthodontics; 13(1); pp. 53-54; Jan. 1986.

Richmond; Recording The Dental Cast in Three Dimensions; American Journal of Orthodontics and Dentofacial Orthopedics; 92(3); pp. 199-206; Sep. 1987.

Rudge; Dental Arch Analysis: Arch Form, A Review of the Literature; The European Journal of Orthodontics; 3(4); pp. 279-284; Jan. 1981.

Sahm et al.; "Micro-Electronic Monitoring of Functional Appliance Wear"; Eur J Orthod.; 12(3); pp. 297-301; Aug. 1990.

Sahm; Presentation of a wear timer for the clarification of scientific questions in orthodontic orthopedics; Fortschritte der Kieferorthopadie; 51 (4); pp. 243-247; (Translation Included) Jul. 1990.

Sakuda et al.; Integrated Information-Processing System In Clinical Orthodontics: An Approach with Use of a Computer Network System; American Journal of Orthodontics and Dentofacial Orthopedics; 101(3); pp. 210-220; 20 pages; (Author Manuscript) Mar. 1992.

Schafer et al.; "Quantifying patient adherence during active orthodontic treatment with removable appliances using microelectronic wear-time documentation"; Eur J Orthod.; 37(1)pp. 1-8; doi:10.1093/ejo/cju012; Jul. 3, 2014.

Schellhas et al.; Three-Dimensional Computed Tomography in Maxillofacial Surgical Planning; Archives of Otolaryngology—Head and Neck Surgery; 114(4); pp. 438-442; Apr. 1988.

Schroeder et al; Eds. The Visual Toolkit, Prentice Hall PTR, New Jersey; Chapters 6, 8 & 9, (pp. 153-210,309-354, and 355-428; (year of pub. sufficiently earlier than effective US filing date and any foreign priority date) 1998.

Shilliday; Minimizing finishing problems with the mini-positioner; American Journal of Orthodontics; 59(6); pp. 596-599; Jun. 1971.

(56) References Cited

OTHER PUBLICATIONS

Shimada et al.; Application of optical coherence tomography (OCT) for diagnosis of caries, cracks, and defects of restorations; Current Oral Health Reports; 2(2); pp. 73-80; Jun. 2015.
Siemens; CEREC—Computer-Reconstruction, High Tech in der Zahnmedizin; 15 pagesl; (Includes Machine Translation); (year of pub. sufficiently earlier than effective US filing date and any foreign priority date); 2004.
Sinclair; The Readers' Corner; Journal of Clinical Orthodontics; 26(6); pp. 369-372; 5 pages; retrived from the internet (http://www.jco-online.com/archive/print_article.asp?Year=1992&Month=06&ArticleNum=); Jun. 1992.
Stoll et al.; Computer-aided Technologies in Dentistry; Dtsch Zahna'rztl Z 45, pp. 314-322; (English Abstract Included); (year of pub. sufficiently earlier than effective US filing date and any foreign priority date) 1990.
Sturman; Interactive Keyframe Animation of 3-D Articulated Models; Proceedings Graphics Interface '84; vol. 86; pp. 35-40; May-Jun. 1984.
The American Heritage, Stedman's Medical Dictionary; Gingiva; 3 pages; retrieved from the interent (http://reference.com/search/search?q=gingiva) on Nov. 5, 2004.
The Dental Company Sirona: Cerc omnicam and cerec bluecam brochure: The first choice in every case; 8 pages; (year of pub. sufficiently earlier than effective US filing date and any foreign priority date) 2014.
Thera Mon; "Microsensor"; 2 pages; retrieved from the internet (www.english.thera-mon.com/the-product/transponder/index.html); on Sep. 19, 2016.
Thorlabs; Pellin broca prisms; 1 page; retrieved from the internet (www.thorlabs.com); Nov. 30, 2012.
Tiziani et al.; Confocal principle for macro and microscopic surface and defect analysis; Optical Engineering; 39(1); pp. 32-39; Jan. 1, 2000.
Truax; Truax Clasp-Less(TM) Appliance System; The Functional Orthodontist; 9(5); pp. 22-24, 26-28; Sep.-Oct. 1992.
Tru-Tatn Orthodontic & Dental Supplies, Product Brochure, Rochester, Minnesota 55902, 16 pages; (year of pub. sufficiently earlier than effective US filing date and any foreign priority date) 1996.
U.S. Department of Commerce, National Technical Information Service, Holodontography: An Introduction to Dental Laser Holography; School of Aerospace Medicine Brooks AFB Tex; Mar. 1973, 40 pages; Mar. 1973.
U.S. Department of Commerce, National Technical Information Service; Automated Crown Replication Using Solid Photography SM; Solid Photography Inc., Melville NY,; 20 pages; Oct. 1977.
Vadapalli; Minimum intensity projection (MinIP) is a data visualization; 7 pages; retrieved from the internet (https://prezi.com/tdmttnmv2knw/minimum-intensity-projection-minip-is-a-data-visualization/) on Sep. 6, 2018.
Van Der Linden et al.; Three-Dimensional Analysis of Dental Casts by Means of the Optocom; Journal of Dental Research; 51(4); p. 1100; Jul.-Aug. 1972.
Van Der Linden; A New Method to Determine Tooth Positions and Dental Arch Dimensions; Journal of Dental Research; 51(4); p. 1104; Jul.-Aug. 1972.
Van Der Zel; Ceramic-Fused-to-Metal Restorations with a New CAD/CAM System; Quintessence International; 24(A); pp. 769-778; (year of pub. sufficiently earlier than effective US filing date and any foreign priority date); 1993.
Van Hilsen et al.; Comparing potential early caries assessment methods for teledentistry; BMC Oral Health; 13(16); doi: 10.1186/1472-6831-13-16; 9 pages; Mar. 2013.
Varady et al.; Reverse Engineering of Geometric Models An Introduction; Computer-Aided Design; 29(4); pp. 255-268; 20 pages; (Author Manuscript); Apr. 1997.
Verstreken et al.; An Image-Guided Planning System for Endosseous Oral Implants; IEEE Transactions on Medical Imaging; 17(5); pp. 842-852; Oct. 1998.
Warunek et al.; Physical and Mechanical Properties of Elastomers in Orthodonic Positioners; American Journal of Orthodontics and Dentofacial Orthopedics; 95(5); pp. 388-400; 21 pages; (Author Manuscript); May 1989.
Warunek et.al.; Clinical Use of Silicone Elastomer Applicances; JCO; 23(10); pp. 694-700; Oct. 1989.
Watson et al.; Pressures recorded at te denture base-mucosal surface interface in complete denture wearers; Journal of Oral Rehabilitation 14(6); pp. 575-589; Nov. 1987.
Wells; Application of the Positioner Appliance in Orthodontic Treatment; American Journal of Orthodontics; 58(4); pp. 351-366; Oct. 1970.
Wikipedia; Palatal expansion; 3 pages; retrieved from the internet (https://en.wikipedia.org/wiki/Palatal_expansion) on Mar. 5, 2018.
Williams; Dentistry and CAD/CAM: Another French Revolution; J. Dent. Practice Admin.; 4(1); pp. 2-5 Jan./Mar. 1987.
Williams; The Switzerland and Minnesota Developments in CAD/CAM; Journal of Dental Practice Administration; 4(2); pp. 50-55; Apr./Jun. 1987.
Wireless Sensor Networks Magazine; Embedded Teeth for Oral Activity Recognition; 2 pages; retrieved on Sep. 19, 2016 from the internet (www.wsnmagazine.com/embedded-teeth/); Jul. 29, 2013.
Wishan; New Advances in Personal Computer Applications for Cephalometric Analysis, Growth Prediction, Surgical Treatment Planning and Imaging Processing; Symposium: Computerized Facial Imaging in Oral and Maxilofacial Surgery; p. 5; Presented on Sep. 13, 1990.
Witt et al.; The wear-timing measuring device in orthodontics-cui bono? Reflections on the state-of-the-art in wear-timing measurement and compliance research in orthodontics; Fortschr Kieferorthop.; 52(3); pp. 117-125; (Translation Included) Jun. 1991.
Wolf; Three-dimensional structure determination of semi-transparent objects from holographic data; Optics Communications; 1(4); pp. 153-156; Sep. 1969.
WSCG'98—Conference Program, The Sixth International Conference in Central Europe on Computer Graphics and Visualization '98; pp. 1-7; retrieved from the Internet on Nov. 5, 2004, (http://wscg.zcu.cz/wscg98/wscg98.htm); Feb. 9-13, 1998.
Xia et al.; Three-Dimensional Virtual-Reality Surgical Planning and Soft-Tissue Prediction for Orthognathic Surgery; IEEE Transactions on Information Technology in Biomedicine; 5(2); pp. 97-107; Jun. 2001.
Yamada et al.; Simulation of fan-beam type optical computed-tomography imaging of strongly scattering and weakly absorbing media; Applied Optics; 32(25); pp. 4808-4814; Sep. 1, 1993.
Yamamoto et al.; Optical Measurement of Dental Cast Profile and Application to Analysis of Three-Dimensional Tooth Movement in Orthodontics; Front. Med. Biol. Eng., 1(2); pp. 119-130; (year of pub. sufficiently earlier than effective US filing date and any foreign priority date); 1988.
Yamamoto et al.; Three-Dimensional Measurement of Dental Cast Profiles and Its Applications to Orthodontics; Conf. Proc. IEEE Eng. Med. Biol. Soc.; 12(5); pp. 2052-2053; Nov. 1990.
Yamany et al.; A System for Human Jaw Modeling Using Intra-Oral Images; Proc. of the 20th Annual Conf. of the IEEE Engineering in Medicine and Biology Society; vol. 2; pp. 563-566; Oct. 1998.
Yoshii; Research on a New Orthodontic Appliance: The Dynamic Positioner (D.P.); 111. The General Concept of the D.P. Method and Its Therapeutic Effect, Part 1, Dental and Functional Reversed Occlusion Case Reports; Nippon Dental Review; 457; pp. 146-164; 43 pages; (Author Manuscript); Nov. 1980.
Yoshii; Research on a New Orthodontic Appliance: The Dynamic Positioner (D.P.); I. The D.P. Concept and Implementation of Transparent Silicone Resin (Orthocon); Nippon Dental Review; 452; pp. 61-74; 32 pages; (Author Manuscript); Jun. 1980.
Yoshii; Research on a New Orthodontic Appliance: The Dynamic Positioner (D.P.); II. The D.P. Manufacturing Procedure and Clinical Applications; Nippon Dental Review; 454; pp. 107-130; 48 pages; (Author Manuscript); Aug. 1980.
Yoshii; Research on a New Orthodontic Appliance: The Dynamic Positioner (D.P.); III—The General Concept of the D.P. Method and

(56) References Cited

OTHER PUBLICATIONS

Its Therapeutic Effect, Part 2. Skeletal Reversed Occlusion Case Reports; Nippon Dental Review; 458; pp. 112-129; 40 pages; (Author Manuscript); Dec. 1980.
Grove et al.; U.S. Appl. No. 15/726,243 entitled "Interproximal reduction templates," filed Oct. 5, 2017.
Cramer; U.S. Appl. No. 15/937,569 entitled "Apparatuses and methods assisting in dental therapies," filed Mar. 27, 2018.
Cramer et al.; U.S. Appl. No. 15/942,341 entitled "Orthodontic appliances including at least partially un-erupted teeth and method of forming them," filed Mar. 30, 2018.
Shanjani et al.; U.S. Appl. No. 16/019,037 entitled "Biosensor performance indicator for intraoral appliances," filed Jun. 26, 2018.
Riley et al.; U.S. Appl. No. 16/003,841 entitled Palatal expander with skeletal anchorage devices, filed Jun. 8, 2018.
Sato et al.; U.S. Appl. No. 16/041,606 entitled "Palatal contour anchorage," filed Jul. 20, 2018.
Sato et al.; U.S. Appl. No. 16/048,054 entitled "Optical coherence tomography for orthodontic aligners," filed Jul. 27, 2018.
Miller et al.; U.S. Appl. No. 16/038,088 entitled "Method and apparatuses for interactive ordering of dental aligners," filed Jul. 17, 2018.
Moalem et al.; U.S. Appl. No. 16/046,897 entitled Tooth shading, transparency and glazing, filed Jul. 26, 2018.
Nyukhtikov et al.; U.S. Appl. No. 15/998,883 entitled "Buccal corridor assessment and computation," filed Aug. 15, 2018.
Bandodkar et al.; All-printed magnetically self-healing electrochemical devices; Science Advances; 2(11); 11 pages; e1601465; Nov. 2016.
Bandodkar et al.; Self-healing inks for autonomous repair of printable electrochemical devices; Advanced Electronic Materials; 1(12); 5 pages; 1500289; Dec. 2015.
Bandodkar et al.; Wearable biofuel cells: a review; Electroanalysis; 28(6); pp. 1188-1200; Jun. 2016.
Bandodkar et al.; Wearable chemical sensors: present challenges and future prospects; Acs Sensors; 1(5); pp. 464-482; May 11, 2016.
Imani et al.; A wearable chemical-electrophysiological hybrid biosensing system for real-time health and fitness monitoring; Nature Communications; 7; 11650. doi 1038/ncomms11650; 7 pages; May 23, 2016.
Jia et al.; Epidermal biofuel cells: energy harvesting from human perspiration; Angewandle Chemie International Edition; 52(28); pp. 7233-7236; Jul. 8, 2013.
Jia et al.; Wearable textile biofuel cells for powering electronics; Journal of Materials Chemistry A; 2(43); pp. 18184-18189; Oct. 14, 2014.
Jeerapan et al.; Stretchable biofuel cells as wearable textile-based self-powered sensors; Journal of Materials Chemistry A; 4(47); pp. 18342-18353; Dec. 21, 2016.
Kim et al.; Advanced materials for printed wearable electrochemical devices: A review; Advanced Electronic Materials; 3(1); 15 pages; 1600260; Jan. 2017.
Kim et al.; Noninvasive alcohol monitoring using a wearable tatto-based iontophoretic-biosensing system; Acs Sensors; 1(8); pp. 1011-1019; Jul. 22, 2016.
Kim et al.; Non-invasive mouthguard biosensor for continuous salivary monitoring of metabolites; Analyst; 139(7); pp. 1632-1636; Apr. 7, 2014.
Kim et al.; A wearable fingernail chemical sensing platform: pH sensing at your fingertips; Talanta; 150; pp. 622-628; Apr. 2016.
Kim et al.; Wearable salivary uric acid mouthguard biosensor with integrated wireless electronics; Biosensors and Bioelectronics; 74; pp. 1061-1068; 19 pages; (Author Manuscript); Dec. 2015.
Kumar et al.; All-printed, stretchable Zn—Ag2o rechargeable battery via, hyperelastic binder for self-powering wearable electronics; Advanced Energy Materials; 7(8); 8 pages; 1602096; Apr. 2017.
Kumar et al.; Biomarkers in orthodontic tooth movement; Journal of Pharmacy Bioallied Sciences; 7(Suppl 2); pp. S325-S330; 12 pages; (Author Manuscript); Aug. 2015.
Parrilla et al.; A textile-based stretchable multi-ion potentiometric sensor; Advanced Healthcare Materials; 5(9); pp. 996-1001; May 2016.
Windmiller et al.; Wearable electrochemical sensors and biosensors: a review; Electroanalysis; 25(1); pp. 29-46; Jan. 2013.
Zhou et al.; Bio-logic analysis of injury biomarker patterns in human serum samples; Talanta; 83(3); pp. 955-959; Jan. 15, 2011.
Zhou et al.; Biofuel cells for self-powered electrochemical biosensing and logic biosensing: A review; Electroanalysis; 24(2); pp. 197-209; Feb. 2012.
Kopelman et al.; U.S. Appl. No. 16/152,281 entitled "Intraoral appliances for sampling soft-tissue," filed Oct. 4, 2018.
Morton et al.; U.S. Appl. No. 16/177,067 entitled "Dental appliance having selective occlusal loading and controlled intercuspation," filed Oct. 31, 2018.
Akopov et al.; U.S. Appl. No. 16/178,491 entitled "Automatic treatment planning," filed Nov. 1, 2018.
Elbaz et al.; U.S. Appl. No. 16/198,488 entitled "Intraoral scanner with dental diagnostics capabilities," filed Nov. 21, 2018.
Elbaz et al.; U.S. Appl. No. 16/188,262 entitled "Intraoral scanner with dental diagnostics capabilities," filed Nov. 12, 2018.
DICOM to surgical guides; (Screenshot)1 page; retrieved from the internet at YouTube (https://youtu.be/47KtOmCEFQk); Published Apr. 4, 2016.

\* cited by examiner

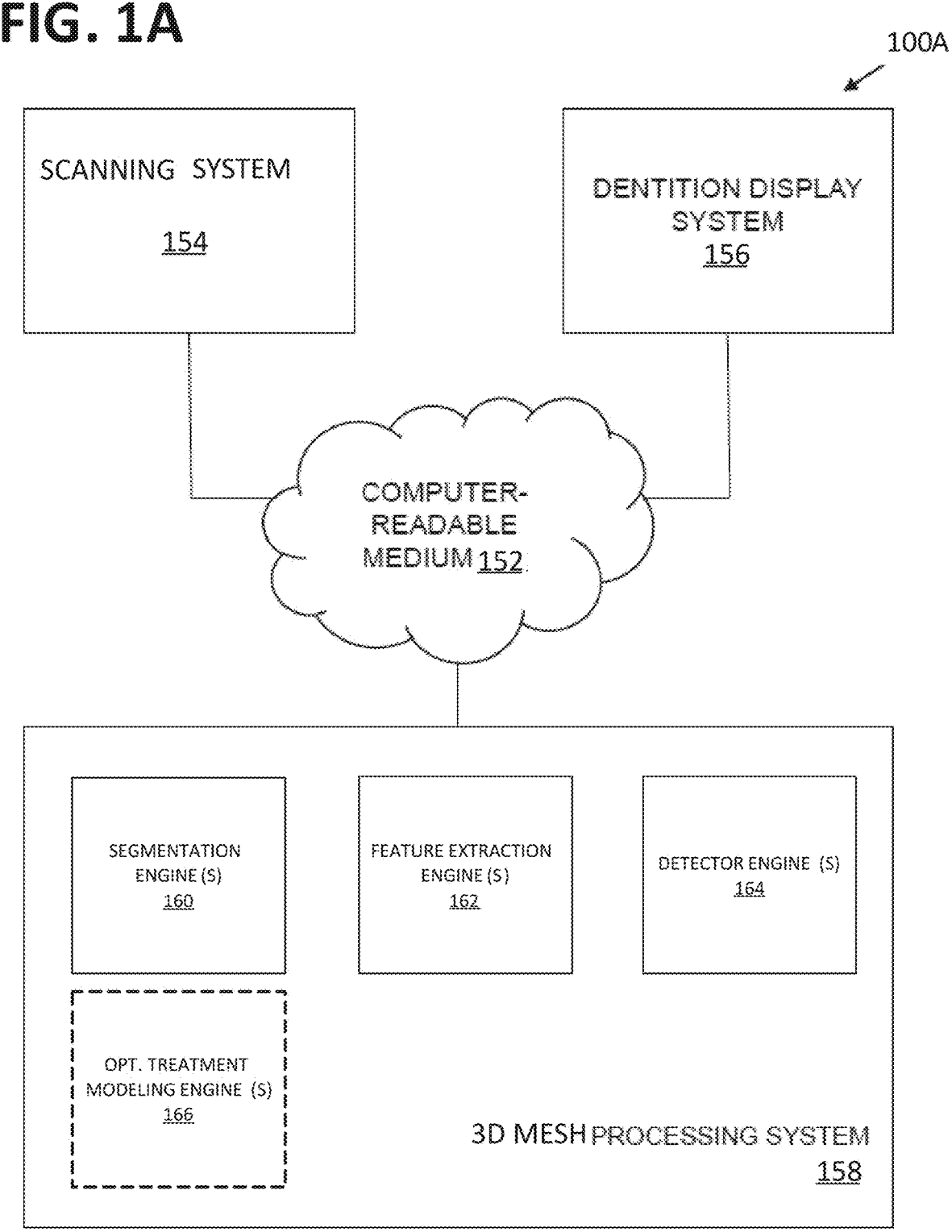

FEATURE EXTRACTION ENGINE(S)
162a

PRINCIPAL COMPONENT ANALYSIS ENGINE
172

CENTER PROJECTION ENGINE
174

TOOTH FEATURE DATASTORE
176

FIG. 1D

FEATURE EXTRACTION ENGINE(S)
162b

TOOTH COMPARISON ENGINE
178

NORMALIZATION ENGINE
180

TOOTH FEATURE DATASTORE
182

AUTOMATIC DETECTION OF TOOTH TYPE AND ERUPTION STATUS

CROSS REFERENCE TO RELATED APPLICATIONS

This patent application claims priority to U.S. Provisional Patent Application No. 62/521,166, titled "AUTOMATIC DETECTION OF TOOTH TYPE AND ERUPTION STATUS," filed on Jun. 16, 2017, which is herein incorporated by reference in its entirety.

INCORPORATION BY REFERENCE

All publications and patent applications mentioned in this specification are incorporated herein by reference in their entirety to the same extent as if each individual publication or patent application was specifically and individually indicated to be incorporated by reference.

BACKGROUND

In pediatric cases, orthodontic aligners are often used before all of the patient's permanent teeth have erupted. Detection of erupting teeth may help prevent the aligner from impinging on or contacting erupting teeth, which can stop eruption of the tooth or injure the patient.

In many existing techniques, a medical professional manually determines the eruption status and tooth type of a patient's teeth. This may require a physical inspection of the teeth or of images/scans of the teeth, and a judgment by the medical professional as to the eruption status and tooth type, adding time and expense.

SUMMARY OF THE DISCLOSURE

Implementations address the need to provide an automated tooth detection eruption detection system to automatically, effectively, and accurately predict tooth type and eruption status in dental patients, with a high degree of accuracy. The present application addresses these and other technical problems by providing technical solutions and/or automated agents that automatically detecting tooth type and eruption status in dental patients. Automatic detection of tooth state (e.g., tooth type and/or eruption status) may provide the basis for implementation of automated orthodontic treatment plans, design and/or manufacture of orthodontic aligners (including series of polymeric orthodontic aligners that provide forces to correct malocclusions in patients' teeth).

In general, example apparatuses (e.g., devices, systems, etc.) and/or methods described herein may receive a representation of a patient's teeth, and in some cases clinical information about the patient, to determine one or more tooth eruption indicators related to a patient's teeth. A "tooth eruption indicator," as used herein, may include an indicator of a tooth related to eruption. Examples of tooth eruption indicators include eruption states of a tooth. Examples of eruption states include eruption statuses (e.g., whether a tooth has fully erupted, partially erupted, or not erupted at all) and eruption permanentness statuses ((e.g., whether a tooth is a primary/baby tooth or a permanent tooth). In some implementations, the eruption status, tooth type (e.g., primary, permanent, etc.), and/or other features related to the patient's teeth may be determined. These apparatuses and/or methods may present the tooth eruption indicators, and may provide or modify a treatment plan, including an orthodontic treatment plan. The apparatuses and/or methods described herein may provide instructions to generate and/or may generate a set or series of aligners, and/or orthodontic treatment plans using orthodontic aligners that incorporate the eruption status and primary/permanent tooth type. The apparatuses and/or methods described herein may provide a visual representation of the patient's teeth including the eruption status and primary/permanent tooth type.

A "patient," as used herein, may be any subject (e.g., human, non-human, adult, child, etc.) and may be alternatively and equivalently referred to herein as a "patient" or a "subject." A "patient," as used herein, may but need not be a medical patient. A "patient," as used herein, may include a person who receives orthodontic treatment, including orthodontic treatment with a series of orthodontic aligners.

Any of the apparatuses and/or methods described herein may be part of a distal tooth scanning apparatus or method, or may be configured to work with a digital scanning apparatus or method.

As will be described in greater detail herein, automatically determining the eruption status and/or primary or permanent tooth type of a target tooth (e.g., for each of a patient's teeth) may include collecting a 3D scan of the patient's teeth. Collecting the 3D scan may include taking the 3D scan, including scanning the patient's dental arch directly (e.g., using an intraoral scanner) or indirectly (e.g., scanning an impression of the patient's teeth), receiving the 3D scan information from a separate device and/or third party, receiving the 3D scan from a memory, or the like.

Additional information may be collected with the 3D scan, including patient information (e.g., age, gender, etc.). The 3D scan information may be standardized and/or normalized. Standardizing the scan may include converting the 3D scan into a standard format (e.g., a tooth surface mesh), and/or expressing the 3D scan as a number of angles (e.g., vector angles) from a center point of each tooth, etc. In some variations, standardizing may include normalizing the 3D scan using another tooth, including stored tooth values.

The standardized 3D scan information may then be processed to extract one or more features that may be used to automatically determine if a tooth is erupted, partially erupted, or un-erupted and/or the type of tooth; specifically, if the tooth is a primary tooth or a permanent tooth. This information may be used to automatically and accurately label the teeth of the 3D model, e.g., by numbering the teeth in a standard tooth numbering.

For example, a method of automatically determining the eruption status and primary or permanent tooth type of a target tooth may include: gathering, in a computing device, a three-dimensional (3D) model of the patient's teeth including the target tooth; standardizing the 3D model of the target tooth; applying, in the computing device, a principal component analysis (PCA) of the dental features of the target tooth to obtain PCA features; determining an eruption status and primary or permanent tooth type of the target tooth based on the PCA features; and outputting the eruption status and primary or permanent tooth type of the target tooth.

Note that although there are examples provided herein using PCA, other eigenvector-based multivariate analyses may be used. PCA is proposed because it may be automatically performed using know techniques including computing PCA using a correlation technique and/or a covariance technique, iterative methods including but not limited to non-linear iterative partial least squares techniques.

Standardizing may include identifying a predetermined number of angles relative to a center point of the target tooth. Any appropriate method may be used to determine the center of the tooth. For example, the center of the tooth may be determined from a mesh point representation of each tooth (e.g., from a segmented version of the 3D scan representing a digital model of the patient's teeth) by determining the geometric center of the mesh points for each tooth, by determining the center of gravity of the segmented tooth, etc. The same method for determining the center of each tooth may be consistently applied between the teeth and any teeth used to form (e.g., train) the systems described herein.

Standardizing may be distinct from normalizing. As used herein, standardizing may involve regularizing numerical and/or other description(s) of a tooth. For example, standardizing may involve regularizing the order and/or number of angles (from the center of the tooth) used to describe the teeth. The sizes of the teeth from the original 3D scan may be maintained.

Any of the methods and systems described herein may be determine for each tooth in a dental arch if that tooth is a primary tooth or a permanent tooth and/or if the tooth is erupted, un-erupted or partially erupted. Thus, any of these methods may determining for one or more (e.g., all) of the patient's teeth in the 3D scan of the patient's arch if the tooth is a primary erupted, permanent partially erupted/un-erupted, and/or permanent erupted tooth. In any of these methods and systems, the system may use this information to label a digital model of the patient's teeth with an indicator for each tooth for which the eruption status and/or primary/permanent description has been determined. For example, the apparatuses and/or methods described herein may output (by display, transmission, etc.) a 3D model of the patient's teeth labeling each tooth as one of: primary erupted (or just "primary"), permanent partially erupted/un-erupted, and/or permanent erupted tooth (or just "permanent").

The 3D scan of the patient's teeth may be collected in any appropriate manner that permits it to be later manipulated by the method or apparatus for standardization, feature extraction and determining eruption status and/or permanent/primary status. For example, gathering may include taking the 3D model of the patient's teeth directly or indirectly form the patient's teeth. For example, gathering may include receiving a 3D model of the patient's teeth from an intraoral scanner. Gathering may include receiving the 3D model from a scan of a mold of the patient's teeth.

Any of the apparatuses and/or methods described herein may include gathering patient information about the patient, wherein the patient information includes one or more of: patient age, eruption sequence, measured space available for eruption, and patient gender; further wherein determining an eruption status and primary or permanent tooth type of the target tooth is also based on the patient information. Patient information may be taken directly or indirectly from the patient, including by asking and/or receiving patient questionnaire information, extracting patient information for a patient's electronic records, etc.

Any appropriate features may be extracted from the prepared (e.g., standardized and/or normalized) teeth. For example, in some variations, features may include a principal component analysis (PCA) for each of the teeth in the dental arch being examined. Additional features (e.g., geometric descriptions of the patient's teeth) may not be necessary (e.g., PCA alone may be used) or it may be used to supplement the PCA of each tooth. PCA may be performed on the standardized teeth automatically using any appropriate technique, as discussed above, including using modules from existing software environments such C++ and C# (e.g., ALGLIB library that implements PCA and truncated PCA, MLPACK), Java (e.g., KNIME, Weka, etc.), Mathematica, MATLAB (e.g., MATLAB Statistics Toolbox, etc.), python (e.g., Matplotlib python library, Scikit-learn, etc.), GNU Octave, etc.

In any of the methods an apparatuses described herein the eruption status and primary or permanent tooth type may be determined automatically (e.g., using one or more processors) based on information extracted from the standardized 3D scan. Before or as part of the standardizing process, the 3D model of the patient's tooth may be segmented into individual teeth and/or normalized. For example, the 3D scan of the patient's arch may be transmitted to and processed by a segmentation engine that divides the 3D scan into individual teeth and/or gingiva.

For example, the method and/or apparatus may determine an eruption status and primary or permanent tooth type of the target tooth based on the PCA features by applying machine learning algorithms selected from the group consisting of Decision Tree, Random Forest, Logistic Regression, Support Vector Machine, AdaBOOST, K-Nearest Neighbor (KNN), Quadratic Discriminant Analysis, and Neural Network. For example, machine learning techniques may be used to form and apply a trained network (neural network). Alternatively or additionally, a logistic regression may be used.

A system (e.g., a system for determining the eruption status and primary or permanent tooth type) may include: one or more processors; memory coupled to the one or more processors, the memory configured to store computer-program instructions, that, when executed by the one or more processors, implement a computer-implemented method, the computer-implemented method comprising: gather a three-dimensional (3D) model of a patient's teeth including a target tooth; standardize the 3D model of the target tooth; apply a principal component analysis (PCA) of the dental features of the target tooth to obtain PCA features; determine an eruption status and primary or permanent tooth type of the target tooth based on the PCA features; and output the eruption status and primary or permanent tooth type of the target tooth. Any of these systems may include a memory for storing the results (e.g., the labeled 3D model of the teeth). Any of these systems may also include an output (e.g., monitor, printer, transmitter, including wireless transmitter), etc.

The apparatuses and/or methods described herein may also be performed using one or more set of reference teeth for normalization. For example, the methods described herein may include a method of automatically determining the eruption status and primary or permanent tooth type of a target tooth. The method may include: receiving, in a computing device, a three-dimensional (3D) model of the patient's teeth including the target tooth, determining, in the computing device, tooth shape features of the target tooth from the 3D model of the patient's teeth, determining, in the computing device, tooth shape features of one or more reference teeth from the 3D model of the patient's teeth, normalizing, in the computing device, at least some of the tooth shape features of the target tooth using the tooth shape features of the one or more reference teeth, applying the normalized tooth shape features to a classifier of the computing device, and outputting from the computing device the eruption status and primary or permanent tooth type of the target tooth.

In any of the apparatuses and/or methods described herein automatically determining eruption status may be performed using an apparatus (e.g., computing device) without human control or direction, particularly in the steps of receiving, determining tooth shape features, normalizing, etc. Alternatively or additionally, any of these steps may be performed partially automatically (e.g., semi-autonomously) or manually.

A computing device may receive a three-dimensional (3D) model of the patient's teeth including the target tooth either directly (e.g., as part of a scanning apparatus or system), or indirectly, including transfer from a previously taken model. The computing device may be a dedicated device or part of a dedicated device (e.g., scanner) or it may be wired or wirelessly connected to a scanning device or a memory storing scanning information. Alternatively or additionally, the computing device may receive the 3D model from a remote (e.g., internet, cloud, etc.) source.

In any of the apparatuses and/or methods described herein a target tooth may be user-selected. Alternatively or additionally, all of the teeth in a 3D model of the teeth may be selected as targets; the apparatus and methods may sequentially or concurrently determine the eruption status and primary or permanent tooth status for each of the plurality of target teeth (including for all of the teeth).

In any of the apparatuses and/or methods described herein, an output may be provided that includes outputting one of: primary erupted, partially erupted permanent (including permanent un-erupted, referred to generically herein as permanent partially erupted/un-erupted), and permanent erupted. Outputting may include fabricating an orthodontic and/or dental appliance based on the determined tooth status (e.g., primary erupted, permanent partially erupted or un-erupted, and permanent erupted). A predicted spacing may be performed based on the primary erupted, permanent partially erupted or un-erupted, and permanent erupted status determined. This spacing may be determined based on the existing and adjacent tooth models (the 3D model) and/or empirical tooth information from the specific patient or a similar patient population. The eruption status information and/or spacing may be used to determine a model (3D model, including digital and non-digital models, such a physical models) that may be fabricated and/or used in the fabrication of a dental and/or orthodontic device.

The methods described herein may also include taking the 3D model of the patient's teeth. The 3D model may be received from a three-dimensional scanner. Alternatively or additionally, the 3D model may be received from a mold of the patient's teeth.

The methods described herein may include getting patient information, wherein the patient information includes one or more of: patient age, eruption sequence, measured space available for eruption, and patient gender; further wherein applying the normalized tooth shape features to the classifier comprises applying the patient information to the classifier with the normalized tooth shape features.

Determining the tooth shape features of the target tooth may comprise determining one or more of: mesial-distal width, buccal-lingual width, crown height, crown center, and number of cusps. Determining the number of cusps can comprise determining the number of cusps in one or more of the arch direction surfaces including: buccal-mesial, buccal-distal, lingual-mesial, and lingual-distal.

Determining the tooth shape features of one or more reference teeth may comprise determining the tooth shape features of one reference tooth. The one or more reference teeth may comprise a molar. Determining the tooth shape features of one or more reference teeth may comprise determining the tooth shape features of two reference teeth. Any appropriate tooth shape feature (morphological feature(s)) may be determined. For example, determining the tooth shape features of one or more reference teeth may comprise determining, for each of the one or more reference teeth, one or more of: mesial-distal width, buccal-lingual width and crown center.

Normalizing at least some of the tooth shape features of the target tooth using the tooth shape features of the one or more reference teeth may comprise normalizing one or more of the mesial-distal width, buccal-lingual width, crown height, and crown center to the one or more reference teeth. Normalizing may further comprise determining a total number of cusps in each of the arch direction surfaces including: buccal-mesial, buccal-distal, lingual-mesial, and lingual-distal.

Any of these methods may also include applying the normalized tooth shape features to the classifier comprises applying either a first level binary classifier or a first level binary classifier and a second level binary classifier to the normalized tooth shape features. Applying the normalized tooth shape features to the classifier may comprise applying a first level binary classifier to a first subset of the normalized tooth shape features and either indicating the eruption status and primary or permanent tooth type of the target tooth based on the first level binary classifier or applying a second level binary classifier to a second subset of the normalized tooth shape features and indicating the eruption status and primary or permanent tooth type of the target tooth based on the second level binary classifier.

Any of these methods can further comprise outputting the eruption status comprises outputting an indication of a percentage of eruption.

Any of the methods of automatically determining the eruption status and primary or permanent tooth type of a target tooth may include: receiving, in a computing device, a three-dimensional (3D) model of the patient's teeth including the target tooth, determining, in the computing device, tooth shape features of the target tooth from the 3D model of the patient's teeth, determining, in the computing device, tooth shape features of one or more reference teeth from the 3D model of the patient's teeth, normalizing, in the computing device, at least some of the tooth shape features of the target tooth using the tooth shape features of the one or more reference teeth, applying the normalized tooth shape features to a classifier of the computing device, wherein applying the normalized tooth shape features to the classifier comprises applying a first level binary classifier and, depending on an output of the first level binary classifier, either outputting the eruption status and primary or permanent tooth type of the target tooth, or applying a second level binary classifier to the normalized tooth shape features and then outputting the eruption status and primary or permanent tooth type of the target tooth.

A method of automatically determining the eruption status and primary or permanent tooth type of a target tooth may include: receiving a three-dimensional model of the patient's teeth including the target tooth, normalizing at least one dimension of the target tooth based on one or more reference teeth, inputting into a first binary classifier tooth shape features including the at least one dimension to determine if the target tooth is a fully erupted permanent tooth, inputting into a second binary classifier the tooth shape features if the first binary classifier determines that the target tooth is not a fully erupted permanent tooth, to determine if the target tooth is a permanent partially erupted/un-erupted tooth or a primary tooth, and outputting that the target tooth is a fully erupted permanent tooth, a permanent partially erupted/un-erupted tooth, or a primary tooth.

Also described herein are apparatuses for performing any of the methods described herein (including software, firmware and/or hardware configured to control the apparatus to perform and/or coordinate the performance of these methods). For example, described herein are non-transitory computing device readable medium having instructions stored thereon for determining the status of a patient's target tooth. The instructions may be executable by a processor to cause a computing device to receive a three-dimensional (3D) model of the patient's teeth including the target tooth, determine tooth shape features of the target tooth from the 3D model of the patient's teeth, determine tooth shape features of one or more reference teeth from the 3D model of the patient's teeth, normalize at least some of the tooth shape features of the target tooth using the tooth shape features of the one or more reference teeth, apply the normalized tooth shape features to a classifier of the computing device; and output the eruption status and primary or permanent tooth type of the target tooth.

The instructions may be further configured so that the output is one of: primary erupted, permanent partially erupted or un-erupted, and permanent erupted.

The instructions may be further configured to receive the 3D model from a three-dimensional scanner. The instructions may be configured to get patient information, wherein the patient information includes one or more of: patient age, eruption sequence, measured space available for eruption, and patient gender; further wherein the instructions are configured to include the patient information with the normalized tooth shape features applied to the classifier.

The instructions may be further configured to determine as part of the tooth shape features one or more of: mesial-distal width, buccal-lingual width, crown height, crown center, and number of cusps.

In any of these apparatuses, the instructions may be further configured to determine the number of cusps by determining the number of cusps in one or more of the arch direction surfaces including: buccal-mesial, buccal-distal, lingual-mesial, and lingual-distal.

The instructions may be configured to determine the tooth shape features of the one or more reference teeth from one reference tooth. The one reference tooth may comprise a molar.

The instructions may be configured to determine the tooth shape features of the one or more reference teeth from two reference teeth.

The instructions may be further configured to determine the tooth shape features of the one or more reference teeth for one or more of: mesial-distal width, buccal-lingual width and crown center.

The instructions may be further configured to normalize the at least some of the tooth shape features of the target tooth using the tooth shape features of the one or more reference teeth by normalizing one or more of the mesial-distal width, buccal-lingual width, crown height, and crown center to the one or more reference teeth.

The instructions may be further configured to normalize the at least some of the tooth shape features of the target tooth by determining a total number of cusps in each of the arch direction surfaces including: buccal-mesial, buccal-distal, lingual-mesial, and lingual-distal.

The instructions may be further configured to apply the normalized tooth shape features to the classifier by applying either a first level binary classifier or a first level binary classifier and a second level binary classifier to the normalized tooth shape features.

The instructions may be further configured to apply a first level binary classifier to a first subset of the normalized tooth shape features and either indicate the eruption status and primary or permanent tooth type of the target tooth based on the first level binary classifier or to apply a second level binary classifier to a second subset of the normalized tooth shape features and indicate the eruption status and primary or permanent tooth type of the target tooth based on the second level binary classifier.

In any of the apparatuses described herein, the instructions may be further configured to output an indication of a percentage of eruption. In general, the output may be visual and/or digital and/or printed.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 1A is a diagram showing an example of a computing environment configured to digitally scan a dental arch and determine a tooth type and/or eruption status of a target tooth.

FIG. 1D is a diagram showing another example of a feature extraction engine(s).

DETAILED DESCRIPTION

Figure 1B:
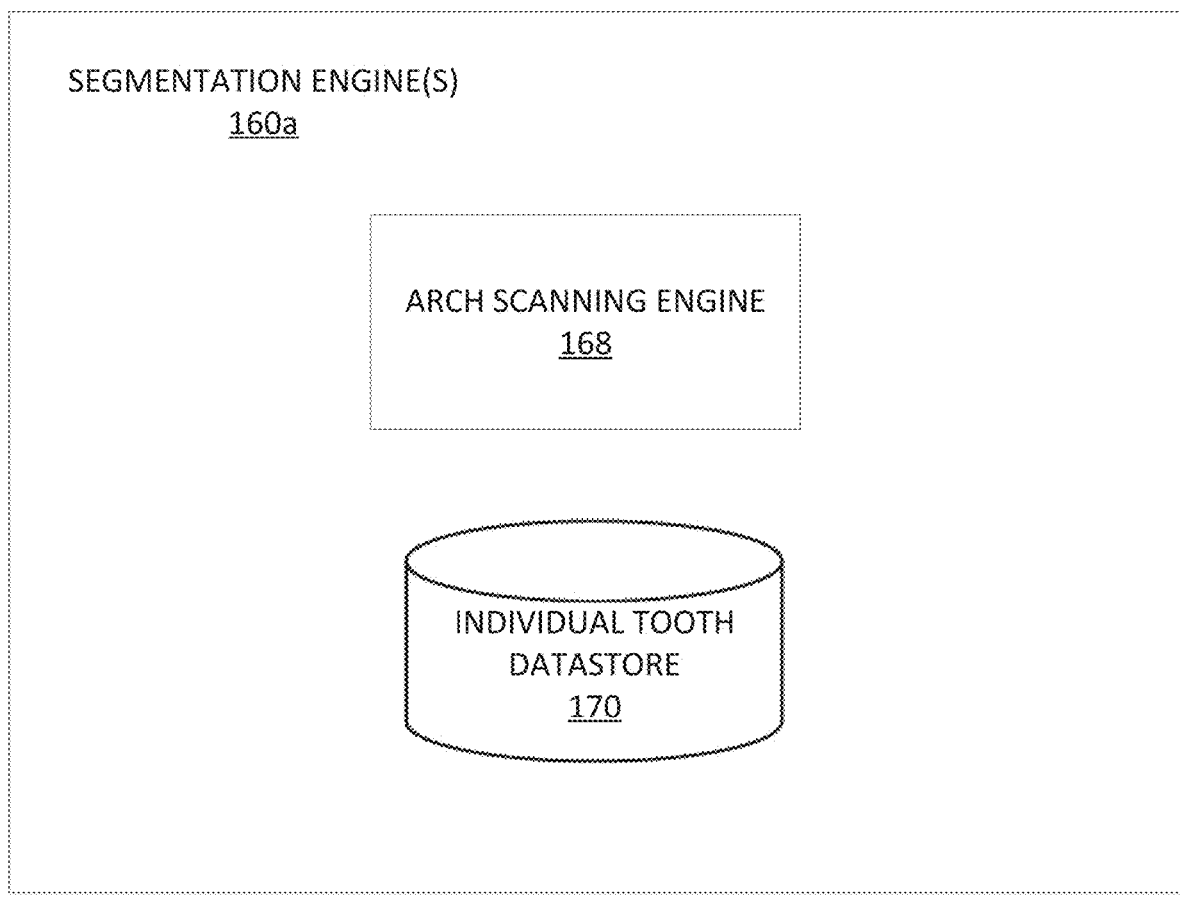
FIG. 1B is a diagram showing an example of segmentation engine(s).

Described herein are apparatuses (e.g., systems, computing device readable media, devices, etc.) and methods for detecting eruption state (e.g., eruption status and tooth type) of a target tooth. Currently, some of the most often heard clinical barriers for teen utilization of orthodontic aligners are the challenges due to un-erupted or erupting teeth. One object of the present disclosure is to use machine learning technology to provide an automatic detector that can distinguish between three tooth type/eruption status for premolars and canines: 1) permanent partially erupted/un-erupted tooth, 2) fully erupted permanent tooth, or 3) fully erupted primary tooth. The detector can make this determination based upon data including patient demographics, tooth measurements, tooth surface mesh, and historical patient data. These methods and apparatus can use this information to provide output to a patient, physician, dental technician, or the like. These apparatuses and/or methods may be further configured to use the determined tooth type and eruption status in forming one or more orthodontic devices (e.g., one or more, including a set, of aligners), treatment plans, or some combination of these.

For example, described herein are apparatuses and/or methods, e.g., systems, including systems to automatically implement processes that incorporate an automatic tooth detector. When the system is triggered by a detection request for a certain tooth, the system can retrieve relevant tooth/patient information from a local or remote database, process the information, and convert the information into representative features. The features can then be passed into an eruption status and tooth type detector, which may use machine learning technology (e.g., Decision Tree, Random Forest, Logistic Regression, Support Vector Machine, AdaBOOST, K-Nearest Neighbor (KNN), Quadratic Discriminant Analysis, Neural Network, etc.) to return a target tooth status classification identifying the eruption status and tooth type of the target tooth. The parameters inputted into the eruption status and tooth type detector can be optimized with historic data. The eruption status and tooth detector may be used to determine the eruption status and permanent/primary tooth type identification on a single tooth (e.g., a single target tooth) or one all of the teeth (or a subset of teeth) in a digital representation of the patient's dental arch. The results may be provided on demand and/or may be stored in a memory (e.g., database) for later use. In some variations the results may be used to modify the labels associated with each tooth reflective of the results (e.g., reflecting the eruption status, such as erupted, partially erupted, un-erupted, and/or primary/permanent status of the teeth).

The apparatuses and/or methods described herein may be useful in planning and fabrication of dental appliances, including elastic polymeric positioning appliances, is described in detail in U.S. Pat. No. 5,975,893, and in published PCT application WO 98/58596, which is herein incorporated by reference for all purposes. Systems of dental appliances employing technology described in U.S. Pat. No. 5,975,893 are commercially available from Align Technology, Inc., Santa Clara, Calif., under the tradename, Invisalign System.

Throughout the body of the Description of Embodiments, the use of the terms "orthodontic aligner", "aligner", or "dental aligner" is synonymous with the use of the terms "appliance" and "dental appliance" in terms of dental applications. For purposes of clarity, embodiments are hereinafter described within the context of the use and application of appliances, and more specifically "dental appliances."

The apparatuses and/or methods (e.g., systems, devices, etc.) described below can be used with and/or integrated into an orthodontic treatment plan. The apparatuses and/or methods described herein may be used to segment a patient's teeth from a two-dimensional image and this segmentation information may be used to simulate, modify and/or choose between various orthodontic treatment plans. Segmenting the patient's teeth can be done automatically (e.g., using a computing device). For example, segmentation can be performed by a computing system automatically by evaluating data (such as three-dimensional scan, or a dental impression) of the patient's teeth or arch.

As described herein, an intraoral scanner may image a patient's dental arch and generate a virtual three-dimensional model of that dental arch. During an intraoral scan procedure (also referred to as a scan session), a user (e.g., a dental practitioner) of an intraoral scanner may generate multiple different images (also referred to as scans or medical images) of a dental site, model of a dental site, or other object. The images may be discrete images (e.g., point-and-shoot images) or frames from a video (e.g., a continuous scan). The three-dimensional scan can generate a 3D mesh of points representing the patient's arch, including the patient's teeth and gums. Further computer processing can segment or separate the 3D mesh of points into individual teeth and gums.

An automated tooth detection system, as used herein, may include a system that uses automated agents to identify and/or number individual teeth and/or dental features of virtual representations of teeth, such as teeth represented in a three-dimensional dental mesh model resulting from a digital scan.

The present disclosure presents one or more novel processes for identifying and segmenting a patient's teeth during an identification process. Some implementations herein may solve technical problems related to optimizing and/or increasing the accuracy of digital dental scanning technologies. The tooth detection processes described herein advantageously may: provide fully automatic tooth detection with no human intervention needed; compensate for errors generated by machine learning detectors; quickly and efficiently identify teeth types and/or eruption status; and/or implement any machine learning detectors.

FIG. 1A is a diagram showing an example of a computing environment 100A configured to facilitate gathering digital scans of a dental arch with teeth therein. The environment 100A includes a computer-readable medium 152, a scanning system 154, a dentition display system 156, and a 3D mesh processing system 158. One or more of the modules in the computing environment 100A may be coupled to one another or to modules not explicitly shown.

The computer-readable medium 152 and other computer readable media discussed herein are intended to represent a variety of potentially applicable technologies. For example, the computer-readable medium 152 can be used to form a network or part of a network. Where two components are co-located on a device, the computer-readable medium 152 can include a bus or other data conduit or plane. Where a first component is co-located on one device and a second component is located on a different device, the computer-readable medium 152 can include a wireless or wired back-end network or LAN. The computer-readable medium 152 can also encompass a relevant portion of a WAN or other network, if applicable.

The scanning system 154 may include a computer system configured to scan a patient's dental arch. A "dental arch," as used herein, may include at least a portion of a patient's dentition formed by the patient's maxillary and/or mandibular teeth, when viewed from an occlusal perspective. A dental arch may include one or more maxillary or mandibular teeth of a patient, such as all teeth on the maxilla or mandible or a patient. The scanning system 154 may include memory, one or more processors, and/or sensors to detect contours on a patient's dental arch. The scanning system 154 may be implemented as a camera, an intraoral scanner, an x-ray device, an infrared device, etc. The scanning system 154 may include a system configured to provide a virtual representation of a physical mold of patient's dental arch. The scanning system 154 may be used as part of an orthodontic treatment plan. In some implementations, the scanning system 154 is configured to capture a patient's dental arch at a beginning stage, an intermediate stage, etc. of an orthodontic treatment plan.

The dentition display system 156 may include a computer system configured to display at least a portion of a dentition of a patient. The dentition display system 154 may include memory, one or more processors, and a display device to display the patient's dentition. The dentition display system 156 may be implemented as part of a computer system, a display of a dedicated intraoral scanner, etc. In some implementations, the dentition display system 156 facilitates display of a patient's dentition using scans that are taken at an earlier date and/or at a remote location. It is noted the dentition display system 156 may facilitate display of scans taken contemporaneously and/or locally to it as well. As noted herein, the dentition display system 156 may be configured to display the intended or actual results of an orthodontic treatment plan applied to a dental arch scanned by the scanning system 154. The results may include 3D virtual representations of the dental arch, 2D images or renditions of the dental arch, etc.

The 3D mesh processing system 158 may include a computer system configured to process 3D scans or meshes of a patient's dentition taken by the scanning system 154. As noted herein, the 3D mesh processing system 158 may be configured to process scans of teeth in a dental arch. The 3D mesh processing system 158 may include segmentation engine(s) 160, feature extraction engine(s) 162, and detector engine(s) 164. One or more of the modules of the image processing system 158 may be coupled to each other or to modules not shown.

As used herein, any "engine" may include one or more processors or a portion thereof. A portion of one or more processors can include some portion of hardware less than all of the hardware comprising any given one or more processors, such as a subset of registers, the portion of the processor dedicated to one or more threads of a multi-threaded processor, a time slice during which the processor is wholly or partially dedicated to carrying out part of the engine's functionality, or the like. As such, a first engine and a second engine can have one or more dedicated processors or a first engine and a second engine can share one or more processors with one another or other engines. Depending upon implementation-specific or other considerations, an engine can be centralized or its functionality distributed. An engine can include hardware, firmware, or software embodied in a computer-readable medium for execution by the processor. The processor transforms data into new data using implemented data structures and methods, such as is described with reference to the figures herein.

The engines described herein, or the engines through which the systems and devices described herein can be implemented, can be cloud-based engines. As used herein, a cloud-based engine is an engine that can run applications and/or functionalities using a cloud-based computing system. All or portions of the applications and/or functionalities can be distributed across multiple computing devices, and need not be restricted to only one computing device. In some embodiments, the cloud-based engines can execute functionalities and/or modules that end users access through a web browser or container application without having the functionalities and/or modules installed locally on the end-users' computing devices.

As used herein, "datastores" may include repositories having any applicable organization of data, including tables, comma-separated values (CSV) files, traditional databases (e.g., SQL), or other applicable known or convenient organizational formats. Datastores can be implemented, for example, as software embodied in a physical computer-readable medium on a specific-purpose machine, in firmware, in hardware, in a combination thereof, or in an applicable known or convenient device or system. Datastore-associated components, such as database interfaces, can be considered "part of" a datastore, part of some other system component, or a combination thereof, though the physical location and other characteristics of datastore-associated components is not critical for an understanding of the techniques described herein.

Datastores can include data structures. As used herein, a data structure is associated with a particular way of storing and organizing data in a computer so that it can be used efficiently within a given context. Data structures are generally based on the ability of a computer to fetch and store data at any place in its memory, specified by an address, a bit string that can be itself stored in memory and manipulated by the program. Thus, some data structures are based on computing the addresses of data items with arithmetic operations; while other data structures are based on storing addresses of data items within the structure itself. Many data structures use both principles, sometimes combined in non-trivial ways. The implementation of a data structure usually entails writing a set of procedures that create and manipulate instances of that structure. The datastores, described herein, can be cloud-based datastores. A cloud-based datastore is a datastore that is compatible with cloud-based computing systems and engines.

The segmentation engine(s) 160 may be configured to implement one or more automated agents configured to process tooth scans from the scanning system 154. The segmentation engine(s) 160 may include graphics engines to process images or scans of a dental arch. In some implementations, the segmentation engine(s) 160 format scan data from an scan of a dental arch into a dental mesh model (e.g., a 3D dental mesh model) of the dental arch. The segmentation engine(s) 160 may also be configured to segment the 3D dental mesh model of the dental arch into individual dental components, including segmenting the 3D dental mesh model into 3D mesh models of individual teeth. The 3D dental mesh models of the dental arch and/or the individual teeth may comprise geometric point clouds or polyhedral objects that depict teeth and/or other elements of the dental arch in a format that can be rendered on the dentition display system 156. The segmentation engine(s)

160 may provide 3D dental mesh models and/or other data to other modules of the 3D mesh processing system 158.

The feature extraction engine(s) 162 may implement one or more automated agents configured to extract dental features. A "dental feature," as used herein, may include data points from the 3D dental mesh model that correlate to edges, contours, vertices, vectors, or surfaces of the patient's teeth. A "dental feature" may be based on patient demographics and/or tooth measurements. A dental feature may be related to "PCA features," e.g., those dental features derived from a principal component analysis of a tooth. In some implementations, the feature extraction engine(s) 162 is configured to analyze 3D dental mesh models from the segmentation engine(s) 160 to extract the dental features. The feature extraction engine(s) 162 may implement principal component analysis (PCA) to obtain the dental features. In one implementation, the 3D dental mesh model of individual teeth comprises a scatter plot of points representing a patient's tooth, and PCA can be applied to the scatter plot to obtain vectors along the biggest distribution of scatter plots. The feature extraction engine(s) can then project from the center of the scatter plot to find vectors that intersect the tooth shape at each angle.

The detector engine(s) 164 may implement one or more automated agents configured to predict tooth state (e.g., tooth type and/or eruption status) of a target tooth using extracted dental features. In some implementations, the detector engine(s) 164 assign physical and/or geometrical properties to a 3D dental mesh model that are related to physical/geometrical properties of dental arches or teeth. The detector engine(s) 164 may receive dental features from the feature extraction engine(s) 162 and apply machine learning algorithms to predict tooth type and/or eruption status of a target tooth using extracted dental features. In some implementations, the detector engine(s) 164 use a trained convolutional neural network and/or trained classifiers to classify a target tooth into one or more identified categories of teeth type, eruption status, tooth number, etc. Examples of machine learning systems implemented by the detector engine(s) 164 may include Decision Tree, Random Forest, Logistic Regression, Support Vector Machine, Ada-BOOST, K-Nearest Neighbor (KNN), Quadratic Discriminant Analysis, Neural Network, etc., to determine a tooth type (e.g., incisor, canine, pre-molar, molar, etc.), eruption status (e.g., permanent, permanent erupting, primary), and/or tooth number of the target tooth. The detector engine(s) 164 can incorporate predicted tooth type and/or eruption status into a final segmentation result. The detector engine(s) 164 may also output a final segmentation result to other modules, for example, the optional treatment modeling engine(s) 166. As an example, the detector engine(s) 164 may implement one or more automated segmentation agents that assign tooth identifiers (e.g., universal tooth numbers, tooth type, or eruption status) to specific portions of a 3D dental mesh model.

The optional treatment modeling engine(s) 166 may be configured to store and/or provide instructions to implement orthodontic treatment plans and/or the results of orthodontic treatment plans. The optional treatment modeling engine(s) 166 may provide the results of orthodontic treatment plans on a 3D dental mesh model. The optional treatment modeling engine(s) 166 may model the results of application of orthodontic aligners to the patient's dental arch over the course of an orthodontic treatment plan.

FIG. 1B is a diagram showing an example of the segmentation engine(s) 160a. The segmentation engine(s) 160a may include an arch scanning engine 168 and an individual tooth segmentation datastore 170. One or more of the modules of the segmentation engine(s) 160a may be coupled to each other or to modules not shown.

The arch scanning engine 168 may implement one or more automated agents configured to scan a 3D dental mesh model for individual tooth segmentation data. "Individual tooth segmentation data," as used herein, may include positions, geometrical properties (contours, etc.), and/or other data that can form the basis of segmenting individual teeth from 3D dental mesh models of a patient's dental arch. The arch scanning engine 168 may implement automated agents to separate dental mesh data for individual teeth from a 3D dental mesh model of the dental arch. The arch scanning engine 168 may further implement automated agents to number the individual teeth.

The individual tooth segmentation datastore 170 may be configured to store data related to model dental arches, including model dental arches that have been segmented into individual teeth. The model dental arch data may comprise data related to segmented individual teeth, including tooth identifiers of the individual teeth such as tooth types, tooth numbers, and eruption status(es).

Figure 1C:
FIG. 1C is a diagram showing an example of a feature extraction engine(s).

FIG. 1C is a diagram showing an example of the feature extraction engine(s) 162a. The feature extraction engine(s) 162a may include principal component analysis engine 172, a center projection engine 174, and a tooth feature datastore 170. One or more of the modules of the feature extraction engine(s) 162a may be coupled to each other or to modules not shown.

The principal component analysis engine 172 may implement one or more automated agents configured to apply PCA to the individual tooth segmentation data. The principal component analysis engine 172 may implement one or more automated agents configured to apply PCA to the individual tooth segmentation data to obtain vectors along the biggest distribution of scatter plots. These vectors may represent a point in 3D space where the vectors intersect the tooth shape. The principal component analysis engine 172 may obtain, for example, a limited or specific number of vectors at known angles in 3D space (e.g., 2500 known angles from the 3D mesh model). The principal component analysis engine 172 can communicate the vector data to the center projection engine 174 and to the tooth feature datastore 176.

The center projection engine 174 may implement one or more automated agents configured to find the appropriate center of the individual tooth segmentation data. The center projection engine 174 may, for example, apply various techniques such as geometric center, weighted center, etc., to find the center of the individual tooth segmentation data. The center projection engine 174 can store the center data in the tooth feature datastore 176.

The tooth feature datastore 176 may be configured to store data related to teeth features, including vectors representing the tooth shape and center data representing the center of the individual tooth segmentation data. In some implementations, only a subset of the total tooth features, such as the vectors representing tooth shape, are stored in the tooth feature datastore.

FIG. 1D is a diagram showing an alternative example of a feature extraction engine(s) 162b. The feature extraction engine(s) 162b may include tooth comparison engine 178, normalization engine 180, and a tooth feature datastore 184. One or more of the modules of the feature extraction engine(s) 162a may be coupled to each other or to modules not shown.

The tooth comparison engine 178 may implement one or more automated agents configured to determine tooth shape features from the individual tooth segmentation data. The tooth shape features may comprise, for example, length and/or width of the target tooth, such as mesial-distal width, buccal-lingual width, and crown height, and may additionally include the crown center of the target tooth or the number of cusps of the target tooth. The tooth comparison engine 178 may implement one or more automated agents configured to compare the tooth shape features to one or more reference teeth. The tooth comparison engine 178 can communicate the tooth shape features and comparison data to the tooth feature datastore 182.

The normalization engine 180 may implement one or more automated agents configured to normalize the tooth shape features of the individual tooth segmentation data by taking into consideration individual heterogeneity in tooth size. The normalization engine 180 can communicate the normalization data to the tooth feature datastore 182.

The tooth feature datastore 182 may be configured to store data related to tooth shape features and normalization data from the modules described above.

Figure 1E:
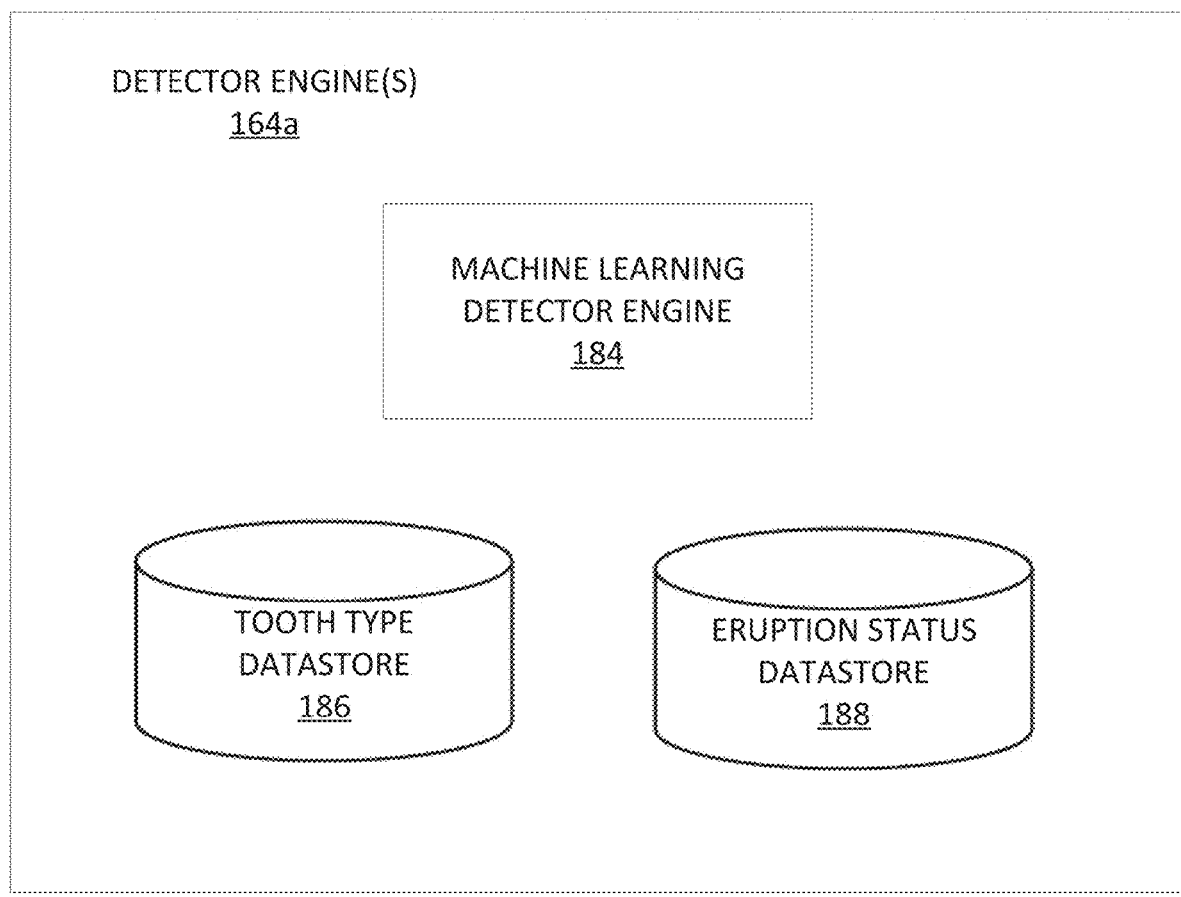
FIG. 1E is a diagram showing an example of detector engine(s).

FIG. 1E is a diagram showing an example of the detector engine(s) 164a. The detector engine(s) 164a may receive teeth features, tooth shape features, or normalization data from either the feature extraction engine(s) 162a or 162b described above. The detector engine(s) 164a may include a machine learning detector engine 184, a tooth type datastore 186, and an eruption status datastore 188.

The machine learning detector engine 184 may implement one or more automated agents configured to use machine learning techniques to classify a tooth eruption state of a target tooth with extracted dental features associated with the target tooth. In some implementations, the machine learning detector engine 184 may receive dental features such as tooth features, tooth shape features, or normalization data from the feature extraction engine(s) 162a or 162b. Using a trained classifier, the machine learning detector engine 184 may provide an identifier (e.g., a statistical or other score) that associates the target tooth with a specified category of tooth. As examples, the machine learning detector engine 184 may use a classifier trained to correlate various dental features with whether a tooth is a partially erupted permanent tooth, a fully erupted permanent tooth, or a fully erupted primary tooth. The machine learning detector engine 184 may use a classifier trained to correlate various dental features with tooth type(s) (e.g., incisor, canine, pre-molar, molar, etc.), eruption status(es) (permanent, permanent erupting, primary), and/or tooth number(s). The machine learning detector engine 184 may incorporate one or more machine learning techniques. Examples of such techniques include Decision Tree, Random Forest, Logistic Regression, Support Vector Machine, AdaBOOST, K-Nearest Neighbor (KNN), Quadratic Discriminant Analysis, Neural Network, etc. . . . .

The tooth type datastore 186 may be configured to store data relating dental features to tooth type(s) (e.g., incisor, canine, pre-molar, molar, etc., and/or a tooth number(s) (e.g., a universal tooth number). In some implementations, the data relating dental features to tooth type(s) and/or tooth number(s) may have been stored by the machine learning detector engine 184 during a training phase. The eruption status datastore 188 may be configured to store data relating dental features eruption status(es) (e.g., permanent, permanent erupting, primary). In some implementations, the data relating dental features to eruption status(es) may have been stored by the machine learning detector engine 184 during a training phase.

Figure 1F:
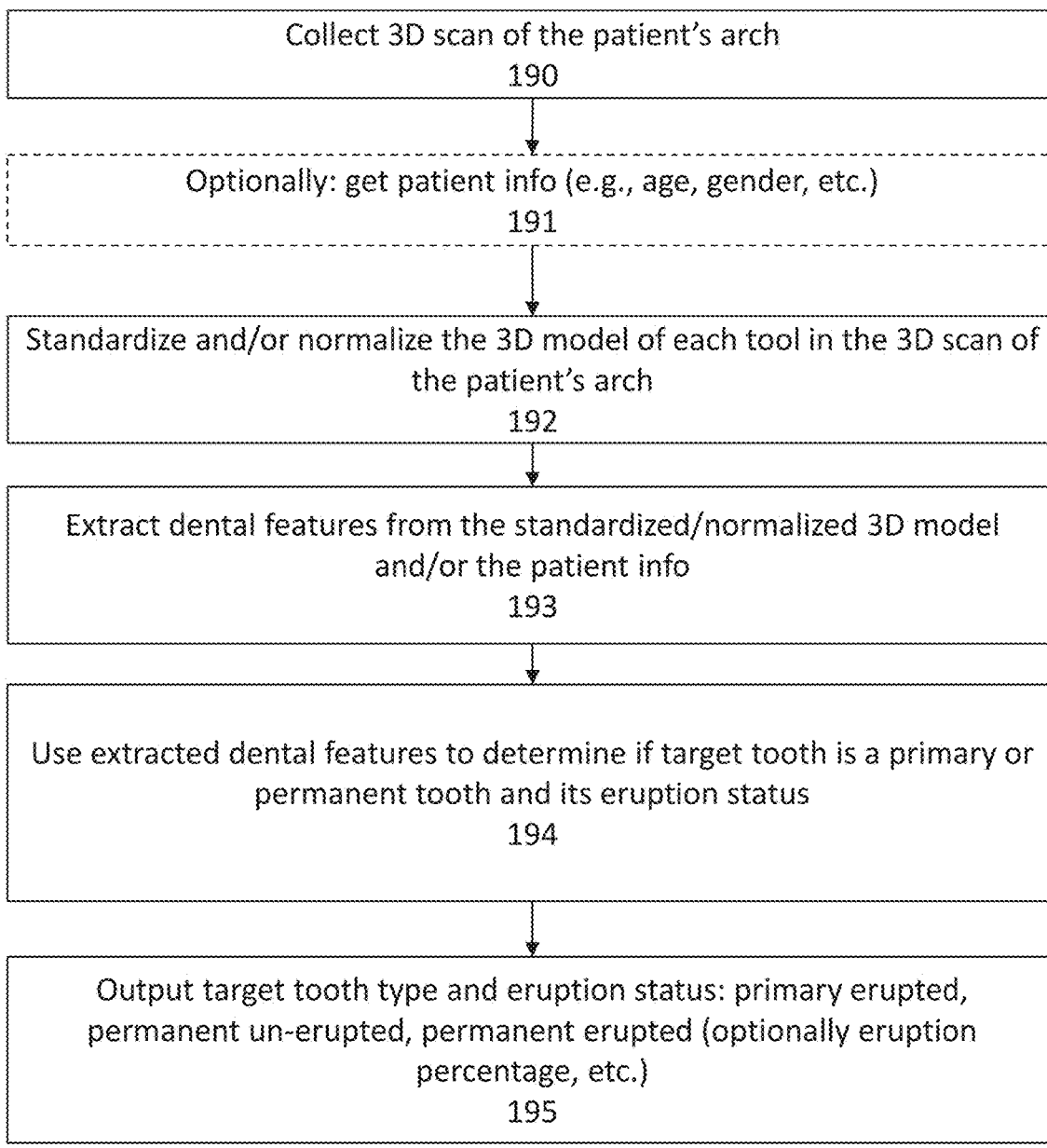
FIG. 1F is an example of a method of automatically determining the eruption status and/or tooth type of a target tooth.

FIG. 1F illustrates one example of a method for automatically determining the eruption state (e.g., eruption status and/or primary/permanent tooth type) for one or more teeth of a patient's dental arch. This method may be automatically implemented by a system, such as one or more of the systems in the computing environment 100A, shown in FIG. 1A. At an operation 190, the system may automatically collect a three-dimensional (3D) scan of the patient's dental arch. The 3D scan may be collected directly from the patient (e.g., using an intraoral scanner) or indirectly (e.g., by scanning a mold of the patient's dentition and/or be receiving a digital model of the patient taken by another, etc.). Optionally, at an operation 191, additional information about the patient may be collected (directly or indirectly), such as the patient's age, gender, etc.

The 3D scan may be prepared for further processing. For example, the 3D scan may be expressed as a digital mesh and/or segmented into individual teeth (and non-teeth elements, such as gingiva, arch, etc.). At an operation 192, the 3D scan may be standardized and/or normalized. For example, in some variations the 3D model may be standardized by expressing each tooth as a set of vectors from a center point of that tooth to a surface point on the tooth. The number and order of the vectors may be preset. For example, over x angles (e.g., over 1000 angles, over 1500 angles, over 2000 angles, over 2500 angles, etc.) may be taken in three dimensional space for each tooth. Alternatively or additionally, as will be described below, the teeth or features extracted from the teeth, may be normalized using database of reference teeth.

At an operation 193, dental features may be extracted from the standardized/normalized 3D model of the patient's teeth (and in some variations from additional data about the patient or the patient's teeth), e.g., using a feature extraction engine. For example, in some variations extraction of features may include automatically performing principle component analysis (PCA) on the teeth (e.g., on each segmented tooth) and the resulting first n terms of the PCA may be used as extracted features (e.g., where n is 10 or more, 15 or more, 20 or more, 30 or more, 40 or more, 50 or more, 60 or more, 70 or more, etc.). Although standardization and normalization are shown together in FIG. 1F (see operation 192) and shown before an operation of feature extraction (see operation 193), in some variations, the operation of normalization (e.g., operation 192) may be performed separately and/or concurrently or after extracting tooth features (e.g., operation 193).

At an operation 194, extracted dental features (e.g., extracted PCA features) may be used exclusively or in combination with any other extracted feature described herein. The extracted dental features may be provided to the detector engine to determine the primary or permanent tooth type and/or eruption status (un-erupted, partially erupted, erupted) for one or more of the patient's teeth 194.

At an operation 195, the eruption state (e.g., primary/permanent tooth type and/or eruption status) for the one or more teeth of the patient's dental arch may then be output. In some variations this information is used to modify a model (e.g., a 3D digital model) of the patient's teeth (e.g., dental arch). For example, each tooth may be labeled and/or referenced by a name or number (or other alphanumeric) that corresponds to the tooth eruption status and/or primary/permanent tooth type. For example, the tooth may be automatically and accurately labeled using these methods and systems in a numbering standard (e.g., a universal number system or a modified universal numbering system) that further indicates primary/permanent teeth. For example, uppercase letters A through T may be used for primary teeth and the numbers 1-32 may be used for permanent teeth, as would be understood by those of skill in the dental/orthodontic art. Alternative standard dental numbering systems may be used (e.g., FDI World Dental Federation notation, Palmer notation, etc.).

Figure 2A:
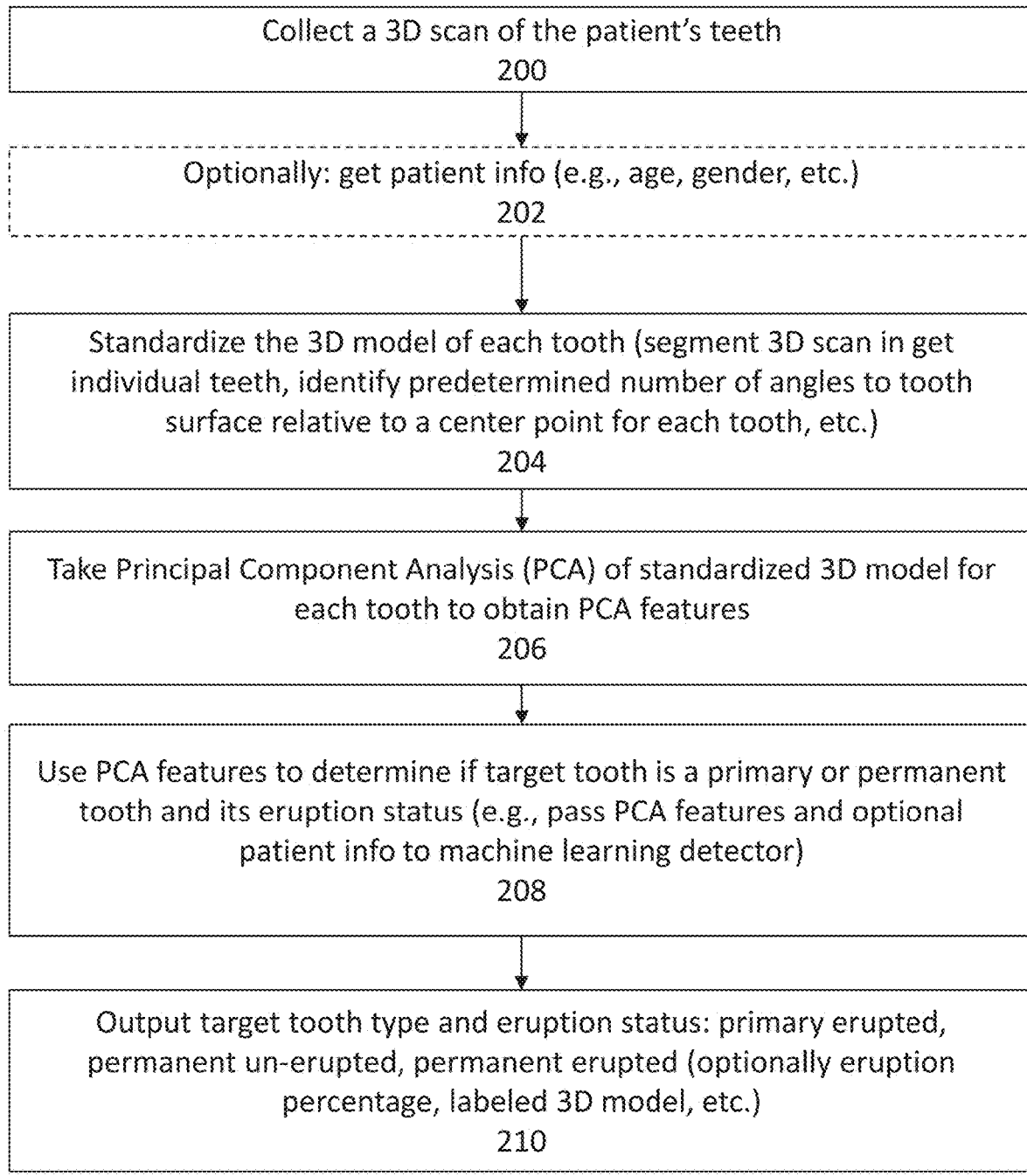
FIG. 2A is an example of a method of automatically determining the eruption status and tooth type of a target tooth.

FIG. 2A shows an example of a flowchart describing a method of automatically determining the eruption status and tooth type of a target tooth of a patient with a detection system. At step 200 of the flowchart in FIG. 2A, a three-dimensional (3D) model of the patient's teeth can be collected. The 3D models may include surface features or surface features and internal features. In some embodiments, the 3D model can be generated with an intraoral scanner that can be hand-held by an operator (e.g., dentist, dental hygienist, technician, etc.) and moved over a patient's tooth or teeth to scan both surface and (optionally) internal structures. In general, any appropriate technique may be used to form the 3D models of the tooth including the surface and internal structures from the intraoral scanner. In another embodiment, the 3D model can be generated from a mold of the patient's teeth.

At step 202 of the flowchart of FIG. 2A, patient info can be (optionally) acquired, such as the patient's age, gender, eruption sequence, measured space available for eruption, etc. Age, eruption sequence, and gender can be useful as supporting factors for prediction. For example, if the patient's $1^{st}$ bicuspid (tooth 4) is erupting earlier than the canine in the upper jaw (tooth 3) or the $2^{nd}$ bicuspid in the upper jaw (tooth 5), then historical eruption sequence data indicates that both teeth 3 and 5 are likely to be primary teeth. Similarly, if tooth 3 is erupting, tooth 4 is likely to be fully erupted, especially for males. This information, if acquired, can be later used by the detection system to aid in determining the eruption status and tooth type of the target tooth. The eruption sequence is not always the same, however it may provide another factor for consideration as described herein. For example, a typical eruption sequence for the upper teeth may be: 6-1-2-4-5-3-7-8, or 6-1-2-4-3-5-7-8. A typical eruption sequence for the lower teeth may be: 6-1-2-3-4-5-7-8.

At step 204 of the flowchart of FIG. 2A, the 3D model of each tooth may be standardized. The detection system can obtain 3D mesh data for each individual tooth from the patient's arch. In some examples, the detection system can implement automated agents to scan and segment the 3D model data of the patient's arch from step 200 into 3D model data of the individual teeth. The 3D model data of the individual teeth can include surface features or surface features and internal features representing the shape of each tooth.

At step 206 of the flowchart of FIG. 2A, a PCA of the standardized 3D model for each tooth may be taken in order to obtain PCA features for the tooth. In some implementations, the detection system can receive or determine tooth or dental features for a target tooth of the patient. These tooth or dental features may include data points from the 3D dental mesh model that correlate to edges, contours, vertices, vectors, or surfaces of the patient's teeth. In one embodiment, the tooth or dental features can be received or determined from the 3D model of the patient's teeth or individual teeth, or alternatively from a clinical evaluation of the patient.

Figure 2B:
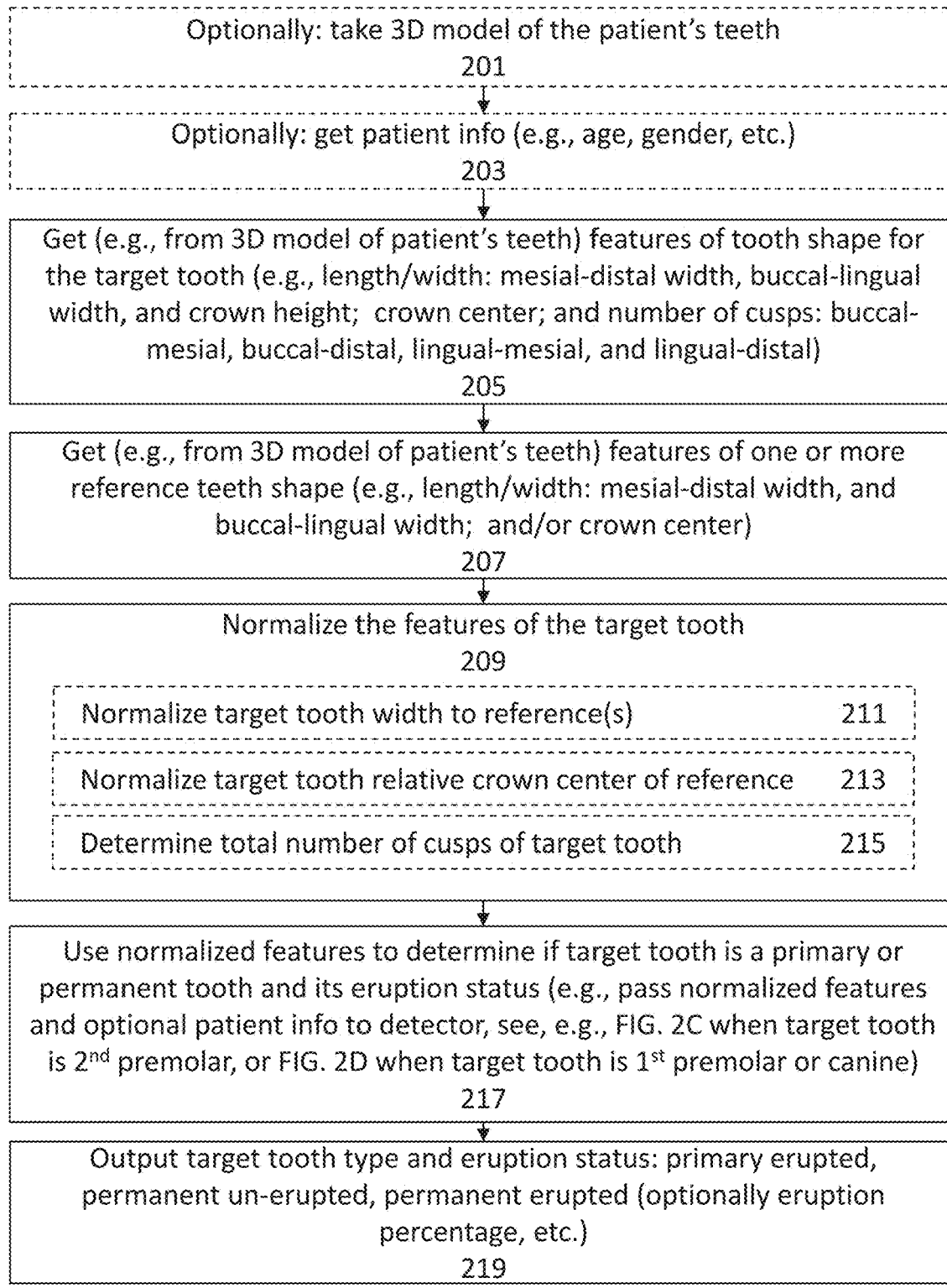
FIG. 2B is an example of a method of automatically determining the eruption status and tooth type of a target tooth.

At step 208 of the flowchart of FIG. 2B, the dental features from step 206 to determine the tooth type (e.g., if the target tooth is a primary tooth or a permanent tooth), the tooth number (e.g., the universal tooth number), and/or the eruption status (e.g., if the target tooth is fully erupted or partially erupted). This can be achieved by passing the tooth or dental features and optional patient info (e.g., patient age/gender, eruption sequence, measured space available for eruption) to a machine learning detector. The machine learning detector can apply machine learning algorithms, including Decision Tree, Random Forest, Logistic Regression, Support Vector Machine, AdaBOOST, K-Nearest Neighbor (KNN), Quadratic Discriminant Analysis, Neural Network, etc., to determine a tooth type (e.g., incisor, canine, pre-molar, molar, etc.), eruption status (permanent, permanent erupting, primary), and/or tooth number of the target tooth by comparing the dental or tooth features and optional patient data to reference dental or tooth features (while accounting for optional patient data).

At step 210 of the flowchart of FIG. 2A, the detection system can receive the tooth type and eruption status, and can output the target tooth type and eruption status. The output can comprise 1) primary tooth type and fully erupted, 2) permanent tooth type and un-erupted/erupting, or 3) permanent tooth type and fully erupted. The output can optionally include the eruption percentage, etc.

FIG. 2B is a flowchart describing a method of automatically determining the eruption status and tooth type of a target tooth of a patient with a detection system. At step 201 of FIG. 1A, a three-dimensional (3D) model of the patient's teeth can be (optionally) taken. The 3D models may include surface features or surface features and internal features. In some embodiments, the 3D model can be generated with an intraoral scanner that can be hand-held by an operator (e.g., dentist, dental hygienist, technician, etc.) and moved over a patient's tooth or teeth to scan both surface and (optionally) internal structures. In general, any appropriate technique may be used to form the 3D models of the tooth including the surface and internal structures from the intraoral scanner. In another embodiment, the 3D model can be generated from a mold of the patient's teeth.

At step 203 of FIG. 2B, patient info can be (optionally) acquired, such as the patient's age, gender, eruption sequence, measured space available for eruption, etc. Age, eruption sequence, and gender can be useful as supporting factors for prediction. For example, if the patient's $1^{st}$ bicuspid (tooth 4) is erupting earlier than the canine in the upper jaw (tooth 3) or the $2^{nd}$ bicuspid in the upper jaw (tooth 5), then historical eruption sequence data indicates that both teeth 3 and 5 are likely to be primary teeth. Similarly, if tooth 3 is erupting, tooth 4 is likely to be fully erupted, especially for males. This information, if acquired, can be later used by the detection system to aid in determining the eruption status and tooth type of the target tooth. The eruption sequence is not always the same, however it may provide another factor for consideration as described herein. For example, a typical eruption sequence for the upper teeth may be: 6-1-2-4-5-3-7-8, or 6-1-2-4-3-5-7-8. A typical eruption sequence for the lower teeth may be: 6-1-2-3-4-5-7-8.

At step 205 of FIG. 2B, the detection system can receive or determine features of tooth shape for a target tooth of the patient. These tooth shape features can include, for example, length and/or width of the target tooth, such as mesial-distal width, buccal-lingual width, and crown height; crown center of the target tooth; and number of cusps of the target tooth, such as buccal-mesial, buccal-distal, lingual-mesial, and lingual-distal. In one embodiment, the features of tooth shape can be received or determined from the 3D model of the patient's teeth, or alternatively from a clinical evaluation of the patient.

At step 207 of FIG. 2B, the detection system can receive or determine features of one or more reference tooth/teeth shape from the patient. The reference tooth/teeth shape features can include, for example, length and/or width of the target tooth/teeth, including mesial-distal width and buccal-lingual width, and can also include crown center of the reference tooth or teeth. In one embodiment, the features of the reference tooth/teeth shape can be received or determined from the 3D model of the patient's teeth, or alternatively from a clinical evaluation of the patient.

Table 1

TABLE 1

| | | | Data Source | |
|---|---|---|---|---|
| | Symbol | Variable Definition | Clinical Eval | 3D Model |
| Tooth i | $W_{BL,i}$ | Buccal-lingual width (Real Geometry) | X | |
| | $W_{MD,i}$ | Mesial-distal width (RG) | X | |
| | $h_i$ | Crown height (RG) | X (fully erupted) | X (partially erupted) |
| | $Z_i$ | Crown center Z | | X |
| | $n_{BM,i}, n_{BD,i}, n_{LM,i}, n_{LD,i}$ | Number of cusps at different surface and arch direction | | X |
| Patient | a | Age | X | |
| $1^{st}$ molars in same jaw | $W_{BL,SSM}, W_{BL,OSM}$ | Buccal-lingual width | X | |
| | $W_{MD,SSM}, W_{MD,OSM}$ | Mesial-distal width | X | |
| | $z_{SSM}, z_{OSM}$ | Crown center Z | X | |
| Central incisors in same jaw | $z_{SSI}$ | Crown center Z | X | |

Subscript notations:
B = buccal,
L = lingual,
M = mesial,
D = distal
SSM = same-side $1^{st}$ molar,
OSM = opposite-side $1^{st}$ molar
SSI = same-side central incisor,
OSI = opposite-side central incisor Table 1 above lists the variables that can be evaluated by the detection system to determine the eruption status and tooth type of a target tooth i. Table 1 also provides the data source for each variable, e.g., whether the data came from a clinical evaluation or from the 3D model.

At step 209 of FIG. 2B, the features of the target tooth can be normalized to take into consideration individual heterogeneity in tooth size. The normalization of features can include any of the steps 211, 213, or 215 of FIG. 2B. In one embodiment, at step 211, the target tooth can be normalized with respect to the width (e.g., buccal-lingual width or mesial-distal width) of a reference tooth or teeth comprising $1^{st}$ molars in the same jaw as the target tooth. In another embodiment, at step 213, the target tooth can be normalized with respect to the crown center of a reference tooth or teeth comprising $1^{st}$ molars in the same jaw as the target tooth, or comprising central incisors in the same jaw as the target tooth. The reference tooth or teeth should be either $1^{st}$ molars or central incisors, which generally erupt at an early age (6-8 years) and therefore widely available in a typical patient. In another embodiment, at step 215, the total number of cusps of the target tooth can be determined.

Referring back to step 211, for the buccal-lingual width, the normalized value is:

$$\hat{w}_{BL,i} = w_{BL,i} / \left( \frac{w_{BL,SSM} + w_{BL,OSM}}{2} \right)$$

If either of the two $1^{st}$ molars is missing, the detection system can use the existing $1^{st}$ molar to do normalization. If both $1^{st}$ molars are missing, the value of $\hat{w}_{BL,i}$ can be set as "not a number" (NaN). A similar approach applies to normalizing a value for the mesial-distal width.

Referring back to step 213, the position of the crown center for the target tooth in the Z direction can be computed relative to a reference tooth or teeth with the following formula:

$$\hat{z}_i = z_i - z_{ref}$$

For premolars, the reference tooth can be the $1^{st}$ molar on the same side of the same jaw, i.e.:

$$z_{ref} = z_{SSM}$$

While for canines, the reference tooth can be the central incisor on the same side of the same jaw, i.e.:

$$z_{ref} = z_{SSI}$$

If $z_{ref}$ is missing, the value of $\hat{z}_i$ should be set as NaN.

Referring back to step 215, the total number of cusps of the target tooth can also be used for eruption status/tooth type detection. The total number of cusps can be computed with:

$$n_i = n_{BM,i} + n_{BD,i} + n_{LM,i} + n_{LD,i}$$

If any of $n_{BM,i}, n_{BD,i}, n_{LM,i}, n_{LD,i}$ is missing, its value can be imputed as 0, with one exception: if all of them are missing, the value of $n_i$ should be set as NaN.

At step 217 of FIG. 2B, the detection system can use the normalized features from step 209 to determine the tooth type (e.g., if the target tooth is a primary tooth or a permanent tooth) and the eruption status (e.g., if the target tooth is fully erupted or partially erupted). This can be achieved by passing the normalized features and optional patient info (e.g., patient age/gender, eruption sequence, measured space available for eruption) to a detector as further described in FIGS. 2C and 2D.

Figure 2C:
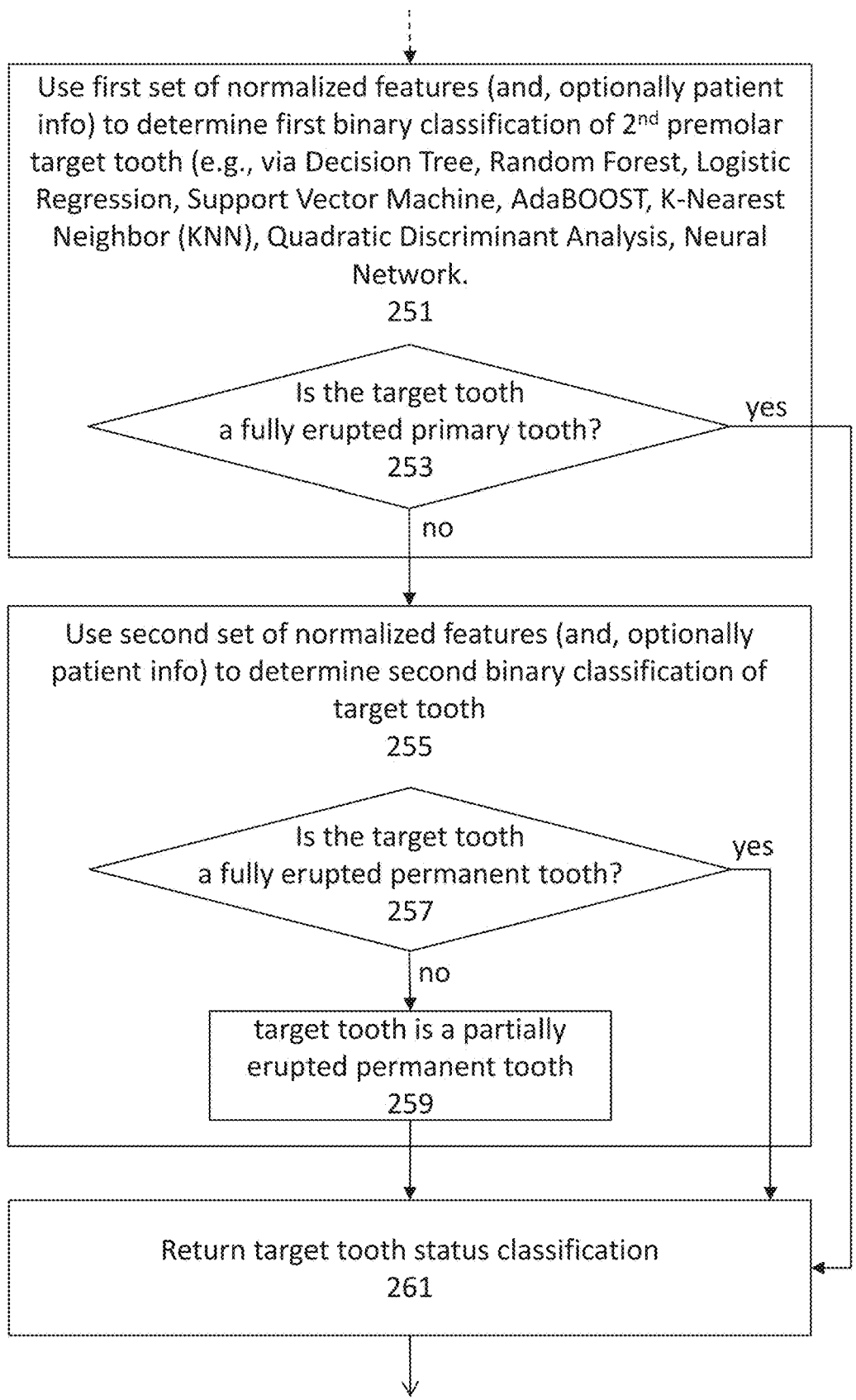
FIGS. 2C-2D are flowcharts describing a detector that uses first and second binary classifiers to determine an eruption status and tooth type of a target tooth. The detector receives normalized features of a target tooth to determine the eruption status and tooth type.
Figure 2D:
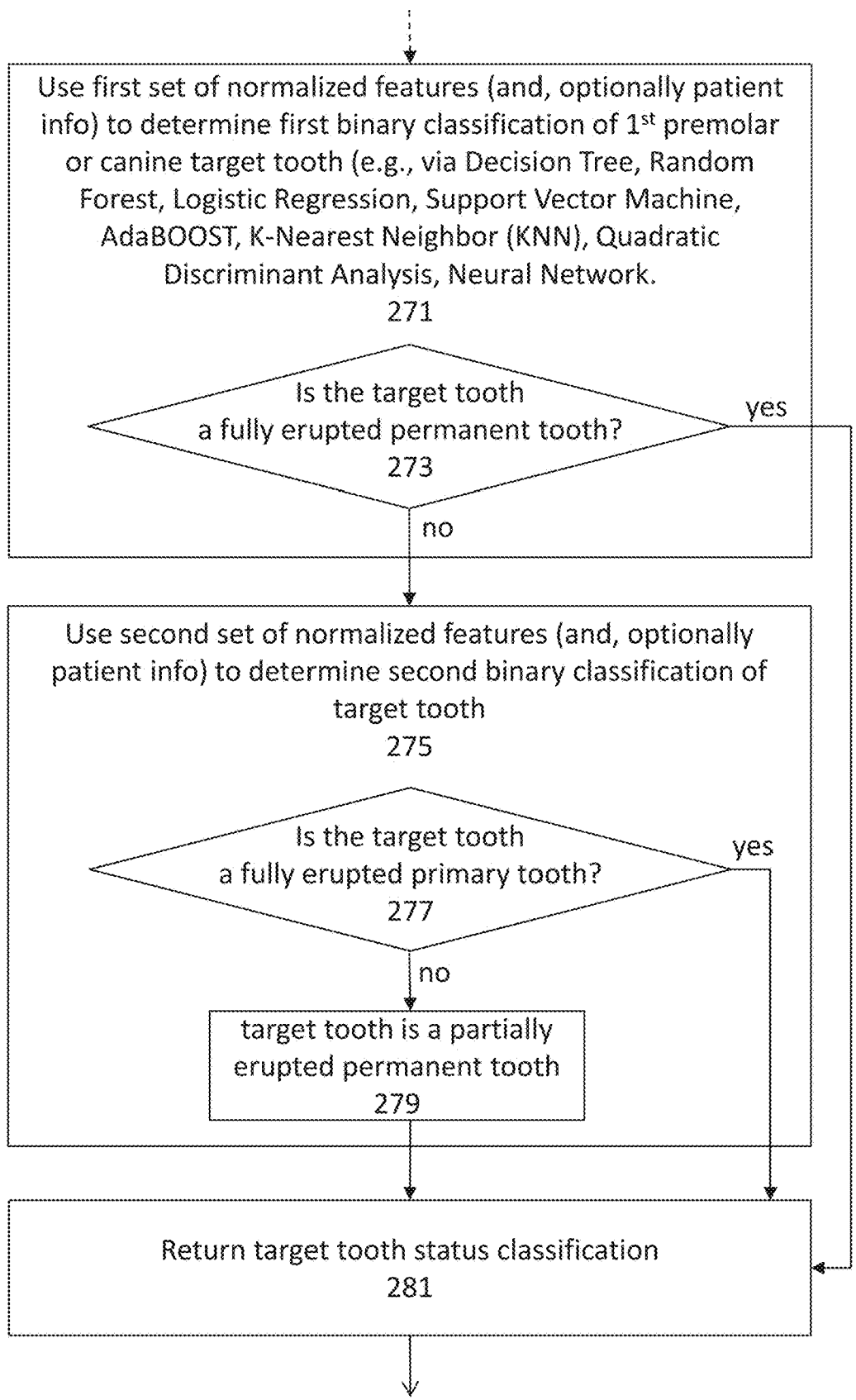

Table 2 provides a list of the normalized features and optional patient info that can be used by the detectors of FIGS. 2C and 2D to return the target tooth status classification. As mentioned above, the level-1 classifier can use a first set of normalized features and the level-2 classifier can use a second set of normalized features.

TABLE 2 list of normalized features and patient info used by detector

| Symbol | Definition |
|---|---|
| $\hat{w}_{BL,i}$ | Normalized buccal-lingual width |
| $\hat{w}_{MD,i}$ | Normalized mesial-distal width |
| $h_i$ | Crown height |
| $\hat{z}_i$ | Relative crown center Z |
| $n_i$ | Total number of cusps |
| a | Patient age |

The detectors of FIGS. 2C and 2D can determine a target tooth status classification from three groups, shown below in Table 3. The classification includes information both on the tooth type (permanent vs. primary) as well as the eruption status (partially erupted vs. fully erupted).

TABLE 3

| | classification groups | |
|---|---|---|
| Category Label | Eruption Status | Tooth Type |
| y = 0 | Partially erupted | Permanent |
| y = 1 | Fully erupted | Permanent |
| y = 2 | Fully erupted | Primary |

Figure 4:
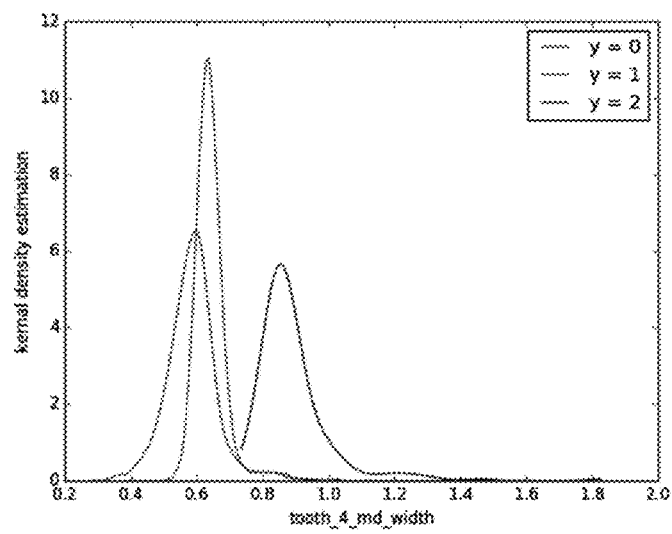
FIG. 4 shows a distribution of mesial-distal width for Tooth 4.
Figure 5A:
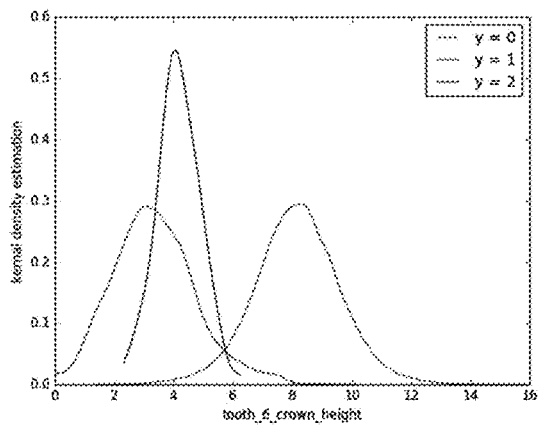
FIG. 5A shows a distribution of crown height for Tooth 6.
Figure 5B:
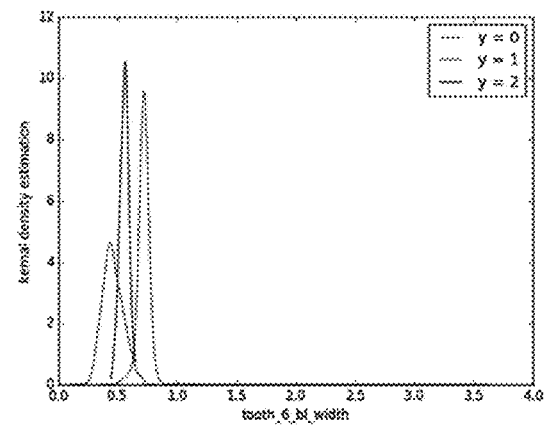
FIG. 5B shows a distribution of buccal-lingual width for Tooth 6.

The detector (either FIG. 2C or FIG. 2D) used at step 217 depends on the tooth type of the target tooth. Thus, one classification structure is used when the target tooth is a $2^{nd}$ premolar, and another classification structure is used when the target tooth is a $1^{st}$ premolar or canine. For $2^{nd}$ premolars, primary teeth differ from permanent teeth significantly in mesial-distal width (see FIG. 4, for example). However, for canines, fully erupted permanent teeth differ from the other two types of teeth significantly in crown height and buccal-lingual width (see FIGS. 5A-4B, for example). A similar pattern can be observed for crown height for 1st premolars (see FIG. 6, for example). Therefore, if the target tooth comprises a $2^{nd}$ premolar, then the normalized features and patient info are passed to the detector of FIG. 2C. If the target tooth comprises a $1^{st}$ premolar or canine, then the normalized features and patient info are passed to the detector of FIG. 2D.

Finally, at step 219 of FIG. 2B, the detection system can receive the tooth type and eruption status from the detector, and can output the target tooth type and eruption status. The output can comprise 1) primary tooth type and fully erupted, 2) permanent tooth type and un-erupted/erupting, or 3) permanent tooth type and fully erupted. The output can optionally include the eruption percentage, etc.

FIG. 2C is a flowchart describing a detector that uses first and second binary classifiers to determine an eruption status and tooth type of a target tooth. As described above, the detector of FIG. 2C is used when the target tooth comprises a $2^{nd}$ premolar. The flowchart of FIG. 2C describes the detector from step 217 of FIG. 2B that is used to determine the target tooth type and eruption status.

The detector of FIG. 2C uses a hierarchical structure to convert multi-class classification problems into a cascading binary classification problem. The detector uses a level-1 classifier (at step 151 of FIG. 2C) to address a first (and relatively easier) classification task followed by, if necessary, a level-2 classifier (at step 155 of FIG. 2C) to complete the classification of the target tooth. The level-1 classifier can use a first set of normalized features, and optionally patient info, to address the first classification task, and the level 2 classifier can use a second set of normalized features, and optionally patient info, to address the second classification task.

Referring to step 251 of FIG. 2C, the detector uses a first set of normalized features (and, optionally patient info) in a level-1 classifier to determine a first binary classification of the target tooth comprising a $2^{nd}$ premolar. The level-1 classifier of the detector can implement various machine learning algorithms, including Decision Tree, Random Forest, Logistic Regression, Support Vector Machine, AdaBOOST, K-Nearest Neighbor (KNN), Quadratic Discriminant Analysis, Neural Network, etc. At step 253, the level-1 classifier can determine if the target tooth is a fully erupted primary tooth based on the first set of normalized features and optionally the patient info. If the level-1 classifier at step 253 determines that the target tooth is a fully erupted primary tooth, then the detector can return the target tooth status classification of "fully erupted primary tooth" at step 261.

However, if the level-1 classifier determines that the target tooth is not a fully erupted primary tooth, then at step 255 of FIG. 2C, the detector uses a second set of normalized features (and, optionally patient info) in a level-2 classifier to determine a second binary classification of the target tooth. The level-2 classifier of the detector can also implement the same various machine learning algorithms as the level-1 classifier. At step 257, the level-2 classifier can determine if the target tooth is a fully erupted permanent tooth based on the second set of normalized features and optionally the patient info. If the level-2 classifier at step 257 determines that the target tooth is a fully erupted permanent tooth, then the detector can return the target tooth status classification of "fully erupted permanent tooth" at step 261. If the level-2 classifier determines that the target tooth is not a fully erupted permanent tooth at step 257, then the level-2 classifier determines at step 259 that the target tooth is a permanent partially erupted/un-erupted tooth, and the detector can then return the target tooth status classification of "permanent partially erupted/un-erupted tooth" at step 261.

Table 4 describes the classifier design when the target tooth comprises a $2^{nd}$ premolar, including the input (normalized) features, and the output options at each stage of the detector. This classifier design is used for the detector of FIG. 2C.

TABLE 4

| classifier design when target tooth comprises $2^{nd}$ premolar | | | |
|---|---|---|---|
| | | Output | |
| classifier | Input features | positive | negative |
| Level-1 | $\hat{w}_{BL,i}, \hat{w}_{MD,i}, h_i, n_i$ | y = 2 | y = 1 or y = 0 |
| Level-2 | $\hat{w}_{BL,i}, \hat{w}_{MD,i}, h_i, \hat{z}_i$ | y = 1 | y = 0 |

Thus, according to Table 4, when the target tooth is a $2^{nd}$ premolar, the normalized features used by the level-1 classifier include normalized buccal-lingual width, normalized mesial-distal width, crown height, and total number of cusps. The normalized features used by the level-2 classifier include normalized buccal-lingual width, normalized mesial-distal width, crown height, and relative crown center Z. The level-1 classifier can return a positive output of a fully erupted primary tooth, and the level-2 classifier can return a positive output of a fully erupted permanent tooth.

FIG. 2D is a flowchart describing a detector that uses first and second binary classifiers to determine an eruption status and tooth type of a target tooth. As described above, the detector of FIG. 2D is used when the target tooth comprises a $1^{st}$ premolar or canine. The detector of FIG. 2D is similar to the detector of FIG. 2C, except the classification determinations are in a slightly different order.

The flowchart of FIG. 2D describes the detector from step 217 of FIG. 2B that is used to determine the target tooth type and eruption status. Similar to above, the detector of FIG. 2D uses a hierarchical structure to convert multi-class classification problems into a cascading binary classification problem. The detector uses a level-1 classifier (at step 271 of FIG. 2D) to address a first (and relatively easier) classification task followed by, if necessary, a level-2 classifier (at step 275 of FIG. 2D) to complete the classification of the target tooth. The level-1 classifier can use a first set of normalized features, and optionally patient info, to address the first classification task, and the level 2 classifier can use a second set of normalized features, and optionally patient info, to address the second classification task.

Referring to step 271 of FIG. 2D, the detector uses a first set of normalized features (and, optionally patient info) in a level-1 classifier to determine a first binary classification of the target tooth comprising a $1^{st}$ premolar or canine. The level-1 classifier of the detector can implement various machine learning algorithms, including Decision Tree, Random Forest, Logistic Regression, Support Vector Machine, AdaBOOST, K-Nearest Neighbor (KNN), Quadratic Discriminant Analysis, Neural Network, etc. At step 273, the level-1 classifier can determine if the target tooth is a fully erupted permanent tooth based on the first set of normalized features and optionally the patient info. If the level-1 classifier at step 273 determines that the target tooth is a fully erupted permanent tooth, then the detector can return the target tooth status classification of "fully erupted permanent tooth" at step 281.

However, if the level-1 classifier determines that the target tooth is not a fully erupted permanent tooth, then at step 275 of FIG. 2D, the detector uses a second set of normalized features (and, optionally patient info) in a level-2 classifier to determine a second binary classification of the target tooth. The level-2 classifier of the detector can also implement the same various machine learning algorithms as the level-1 classifier. At step 277, the level-2 classifier can determine if the target tooth is a fully erupted primary tooth based on the second set of normalized features and optionally the patient info. If the level-2 classifier at step 277 determines that the target tooth is a fully erupted primary tooth, then the detector can return the target tooth status classification of "fully erupted primary tooth" at step 281. If the level-2 classifier determines that the target tooth is not a fully erupted primary tooth at step 277, then the level-2 classifier determines at step 279 that the target tooth is a permanent partially erupted/un-erupted tooth, and the detector can then return the target tooth status classification of "permanent partially erupted/un-erupted tooth" at step 281.

Table 5 describes the classifier design when the target tooth comprises a $1^{st}$ premolar or canine, including the input (normalized) features, and the output options at each stage of the detector. This classifier design is used for the detector of FIG. 2D.

TABLE 5 classifier design when target tooth comprises $1^{st}$ premolar or canine

| classifier | Input features | Output positive | negative |
|---|---|---|---|
| Level-1 | $\hat{w}_{BL,i}$, $\hat{w}_{MD,i}$, $h_i$ | y = 1 | y = 2 or y = 0 |
| Level-2 | $\hat{w}_{BL,i}$, $\hat{w}_{MD,i}$, $h_i$, $\hat{z}_i$, $n_i$, a | y = 2 | y = 0 |

Thus, according to Table 5, when the target tooth is a $1^{st}$ premolar or canine, the normalized features used by the level-1 classifier include normalized buccal-lingual width, normalized mesial-distal width, and crown height. The normalized features used by the level-2 classifier include normalized buccal-lingual width, normalized mesial-distal width, crown height, relative crown center Z, total number of cusps, and optionally patient age. The level-1 classifier can return a positive output of a fully erupted permanent tooth, and the level-2 classifier can return a positive output of a fully erupted primary tooth.

Figure 3A:
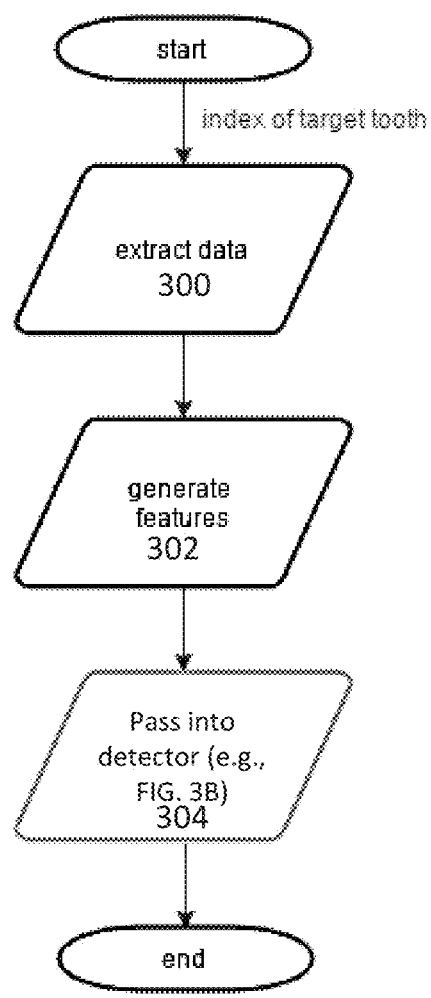
FIG. 3A is a flowchart describing a method of extracting and generating data to be passed into a tooth status classification detector.
Figure 3B:
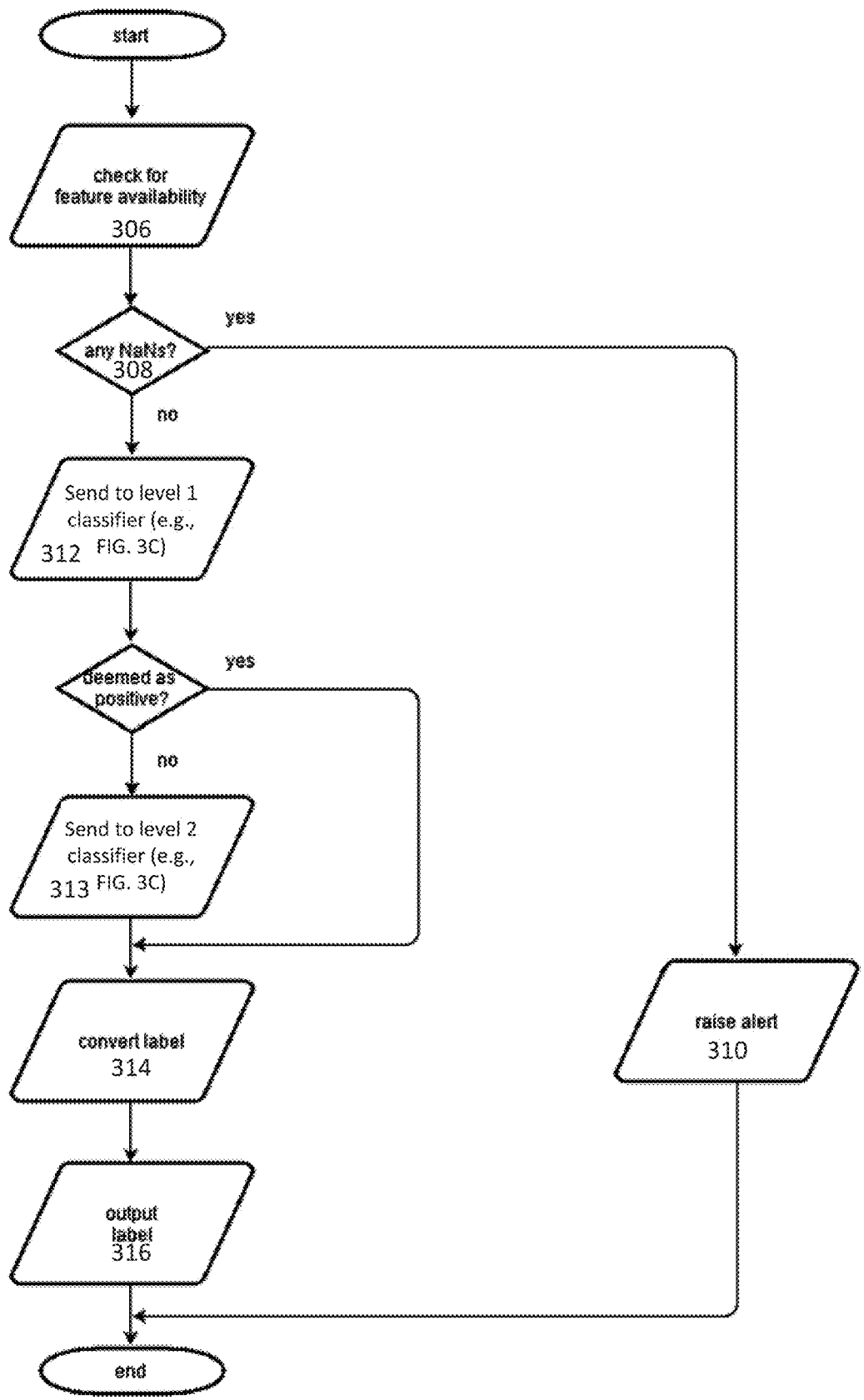
FIG. 3B is a flowchart describing a tooth status classification detector used to determine the eruption status and tooth type of a target tooth with the data from the flowchart of FIG. 3A.
Figure 3C:
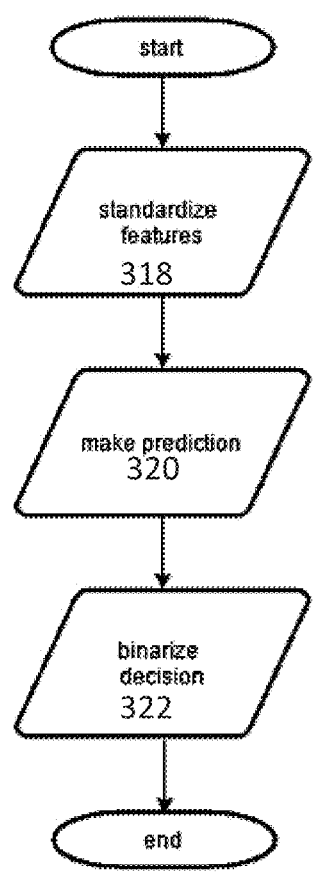
FIG. 3C is a flowchart describing a classifier of the tooth status classification detector that determines an eruption status and tooth type of a target tooth.

FIGS. 3A-3C are another set of flowcharts that show the overall detection system described above. FIG. 3A is a flowchart describing a method of extracting and generating data to be passed into a tooth status classification detector. These steps generally correspond to method steps 201-217 of FIG. 2B above.

At step 300 of FIG. 3A, data can be extracted for use by the detection system. The data can include patient teeth data (e.g., 3D model/scanning of teeth) as well as clinical data about the patient (e.g., patient age, gender, eruption sequence, measured space available for eruption etc.). Next, at step 302 of FIG. 3A, the detection system can generate features from the extracted data. This takes into account variance in the patient's teeth to normalize the data set, as described above. Finally, at step 304 of FIG. 3A, the normalized features can be passed into the detector of FIG. 3B.

FIG. 3B is a flowchart describing a tooth status classification detector used to determine the eruption status and tooth type of a target tooth with the data from the flowchart of FIG. 3A. At step 306 of FIG. 3B, the detector can confirm that the requisite normalized features were passed to the detector. At step 308, if any of the normalized features include a NaN ("not a number") or error message, an alert can be raised at step 310 and the detection process can be ended. If all the normalized features are present, then the normalized features can be passed on to the level-1 classifier at step 312. The level-1 classifier is further illustrated in FIG. 3C.

If the level-1 classifier at step 312 returns a positive result, then the positive result can be converted to a label at step 314 and output back to the system at step 316. The same labels can be used as described above for the FIGS. 2C and 2D detectors. Thus, a positive result at step 312 for a $2^{nd}$ premolar target tooth can be converted at step 314 to a "fully erupted, primary" label, and a positive result at step 312 for a $1^{st}$ premolar or canine target tooth can be converted at step 314 to a "fully erupted, permanent" label.

If the level-1 classifier at step 312 returns a negative result, then the normalized features are further passed on to the level-2 classifier at step 313. This level-2 classifier is also illustrated in FIG. 3C. The level-2 classifier similarly returns either a positive or negative result. Thus, a positive result at step 313 from the level-2 classifier for a $2^{nd}$ premolar target tooth can be converted at step 314 to a "fully erupted, permanent" label, and a positive result at step 313 for a $1^{st}$ premolar or canine target tooth can be converted at step 314 to a "fully erupted, primary" label. A negative result at step 313 from the level-2 classifier for a $2^{nd}$ premolar target tooth can be converted at step 314 to a "partially erupted, permanent" label, and a negative result at step 313 for a $1^{st}$ premolar or canine target tooth can be converted at step 214 to a "partially erupted, permanent" label.

FIG. 3C is a flowchart describing a detector of the detection system that determines an eruption status and tooth type of a target tooth. At step 318, the features are standardized. Feature standardization is a common pre-processing procedure in machine learning and statistics. Next, at step 320, the detector of FIG. 3C makes a prediction, as described above. The prediction can be based on the set of normalized features passed to the detector. The prediction is binarized at step 322, and the passed back to the detection system for output.

Figure 6:
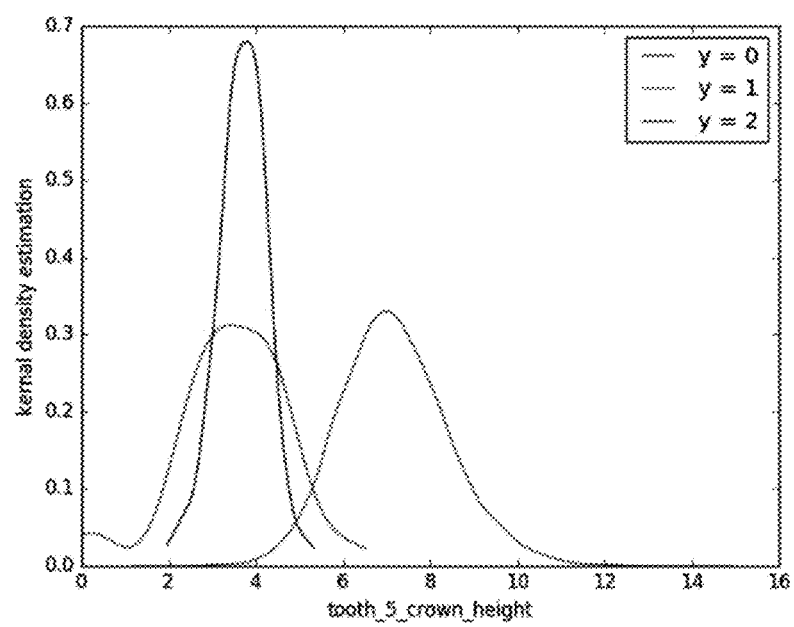
FIG. 6 shows a distribution of crown height for Tooth 5.
Figure 7:
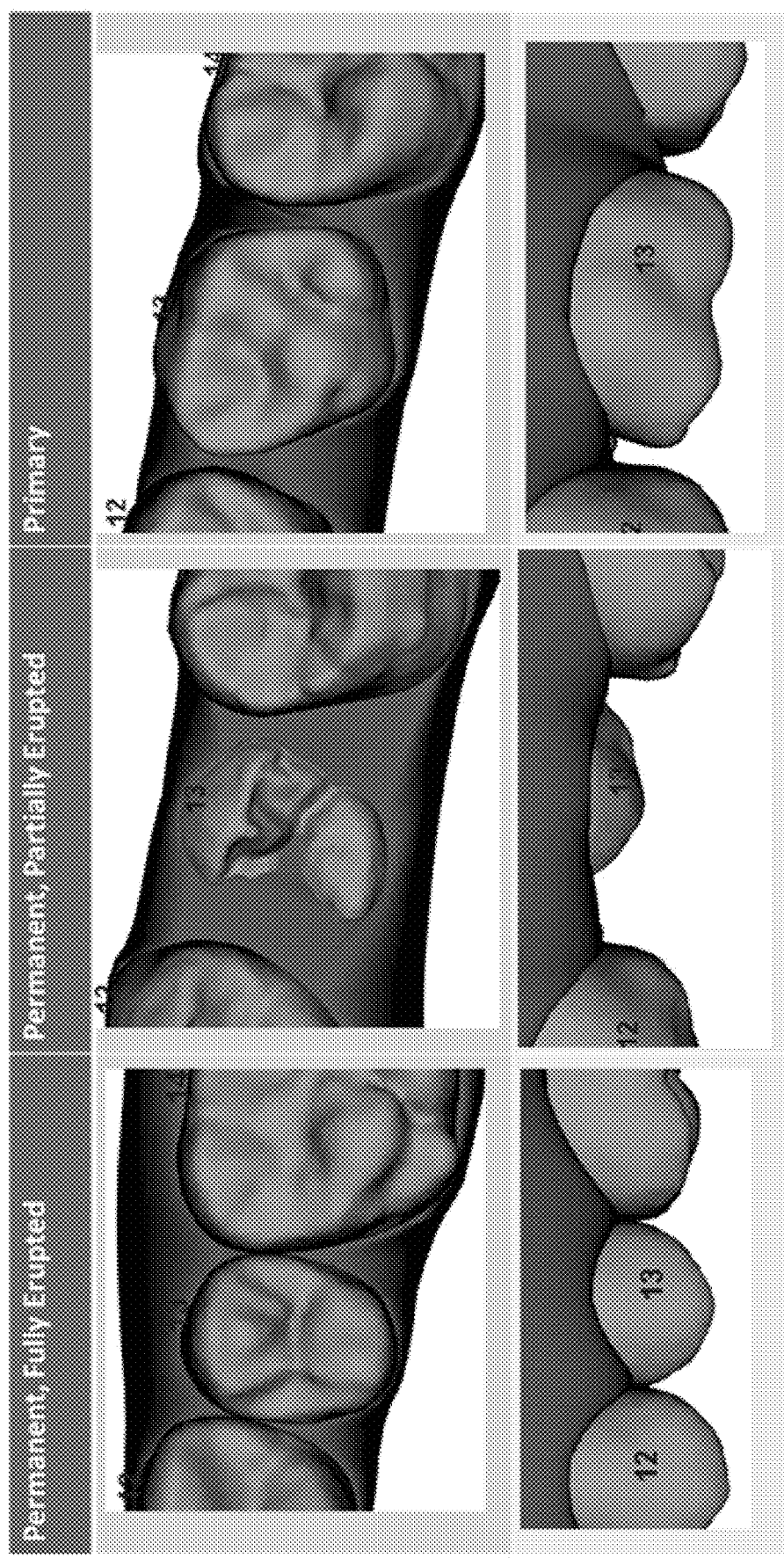
FIG. 7 shows examples of tooth shape by detention type and eruption status, including 1) Permanent, Fully Erupted, 2) Permanent, Partially Erupted, and 3) Primary.

FIG. 7 shows examples of tooth shape by detention type and eruption status. FIG. 6 shows the different tooth types and eruption status for the upper left $2^{nd}$ bicuspid, including 1) Permanent, Fully Erupted, 2) Permanent, Partially Erupted, and 3) Primary.

Figure 8:
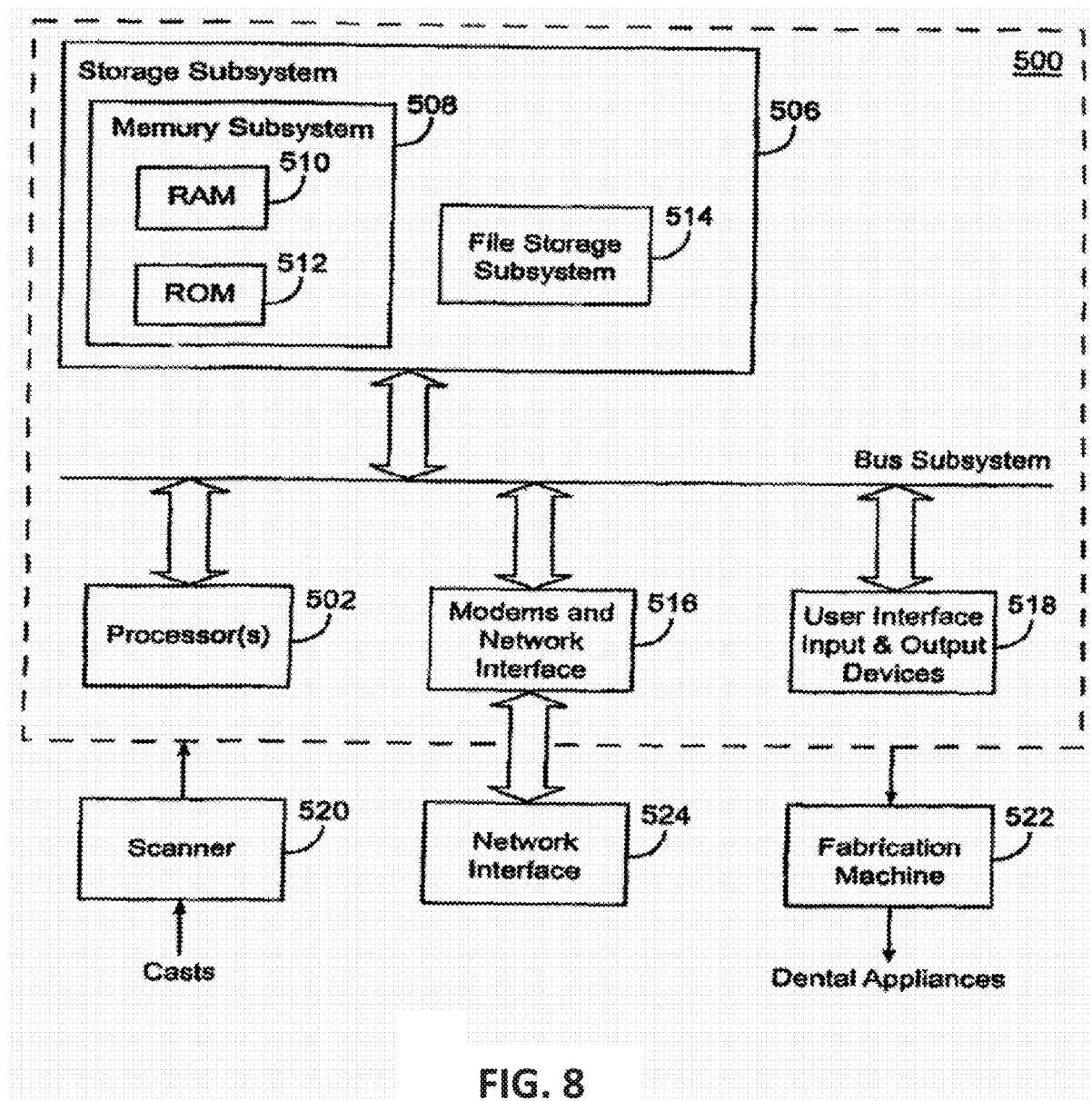
FIG. 8 is a simplified block diagram of a data processing system that may perform the methods described herein.

The methods described herein may be performed by an apparatus, such as a data processing system, which may include hardware, software, and/or firmware for performing many of these steps described above. For example, FIG. 8 is a simplified block diagram of a data processing system 500. Data processing system 500 typically includes at least one processor 502 which communicates with a number of peripheral devices over bus subsystem 504. These peripheral devices typically include a storage subsystem 506 (memory subsystem 508 and file storage subsystem 514), a set of user interface input and output devices 518, and an interface to outside networks 516, including the public switched telephone network. This interface is shown schematically as "Modems and Network Interface" block 516, and is coupled to corresponding interface devices in other data processing systems over communication network interface 524. Data processing system 500 may include a terminal or a low-end personal computer or a high-end personal computer, workstation or mainframe.

The user interface input devices typically include a keyboard and may further include a pointing device and a scanner. The pointing device may be an indirect pointing device such as a mouse, trackball, touchpad, or graphics tablet, or a direct pointing device such as a touchscreen incorporated into the display. Other types of user interface input devices, such as voice recognition systems, may be used.

User interface output devices may include a printer and a display subsystem, which includes a display controller and a display device coupled to the controller. The display device may be a cathode ray tube (CRT), a flat-panel device such as a liquid crystal display (LCD), or a projection device. The display subsystem may also provide nonvisual display such as audio output.

Storage subsystem 506 maintains the basic programming and data constructs that provide the functionality of the present invention. The software modules discussed above are typically stored in storage subsystem 506. Storage subsystem 506 typically comprises memory subsystem 508 and file storage subsystem 514.

Memory subsystem 508 typically includes a number of memories including a main random access memory (RAM) 510 for storage of instructions and data during program execution and a read only memory (ROM) 512 in which fixed instructions are stored. In the case of Macintosh-compatible personal computers the ROM would include portions of the operating system; in the case of IBM-compatible personal computers, this would include the BIOS (basic input/output system).

File storage subsystem 514 provides persistent (nonvolatile) storage for program and data files, and typically includes at least one hard disk drive and at least one floppy disk drive (with associated removable media). There may also be other devices such as a CD-ROM drive and optical drives (all with their associated removable media). Additionally, the system may include drives of the type with removable media cartridges. The removable media cartridges may, for example be hard disk cartridges, such as those marketed by Syquest and others, and flexible disk cartridges, such as those marketed by Iomega. One or more of the drives may be located at a remote location, such as in a server on a local area network or at a site on the Internet's World Wide Web.

In this context, the term "bus subsystem" is used generically so as to include any mechanism for letting the various components and subsystems communicate with each other as intended. With the exception of the input devices and the display, the other components need not be at the same physical location. Thus, for example, portions of the file storage system could be connected over various local-area or wide-area network media, including telephone lines. Similarly, the input devices and display need not be at the same location as the processor, although it is anticipated that the present invention will most often be implemented in the context of PCS and workstations.

Bus subsystem 504 is shown schematically as a single bus, but a typical system has a number of buses such as a local bus and one or more expansion buses (e.g., ADB, SCSI, ISA, EISA, MCA, NuBus, or PCI), as well as serial and parallel ports. Network connections are usually established through a device such as a network adapter on one of these expansion buses or a modem on a serial port. The client computer may be a desktop system or a portable system.

Scanner 520 is responsible for scanning casts of the patient's teeth obtained either from the patient or from an orthodontist and providing the scanned digital data set information to data processing system 500 for further processing. In a distributed environment, scanner 520 may be located at a remote location and communicate scanned digital data set information to data processing system 500 over network interface 524.

Fabrication machine 522 fabricates dental appliances based on intermediate and final data set information received from data processing system 500. In a distributed environment, fabrication machine 522 may be located at a remote location and receive data set information from data processing system 500 over network interface 524.

Various alternatives, modifications, and equivalents may be used in lieu of the above components. Although the final position of the teeth may be determined using computer-aided techniques, a user may move the teeth into their final positions by independently manipulating one or more teeth while satisfying the constraints of the prescription.

Additionally, the techniques described here may be implemented in hardware or software, or a combination of the two. The techniques may be implemented in computer programs executing on programmable computers that each includes a processor, a storage medium readable by the processor (including volatile and nonvolatile memory and/or storage elements), and suitable input and output devices. Program code is applied to data entered using an input device to perform the functions described and to generate output information. The output information is applied to one or more output devices.

Each program can be implemented in a high level procedural or object-oriented programming language to operate in conjunction with a computer system. However, the programs can be implemented in assembly or machine language, if desired. In any case, the language may be a compiled or interpreted language.

Each such computer program can be stored on a storage medium or device (e.g., CD-ROM, hard disk or magnetic diskette) that is readable by a general or special purpose programmable computer for configuring and operating the computer when the storage medium or device is read by the computer to perform the procedures described. The system also may be implemented as a computer-readable storage medium, configured with a computer program, where the storage medium so configured causes a computer to operate in a specific and predefined manner.

Thus, any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like.

While preferred embodiments of the present disclosure have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. Numerous different combinations of embodiments described herein are possible, and such combinations are considered part of the present disclosure. In addition, all features discussed in connection with any one embodiment herein can be readily adapted for use in other embodiments herein. It is intended that the following claims define the scope of the invention and that methods and structures within the scope of these claims and their equivalents be covered thereby.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and/or methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the patient matter may be practiced. As mentioned, other embodiments may be utilized and derived there from, such that structural and logical substitutions and changes may be made without departing from the scope of this disclosure. Such embodiments of the inventive patient matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method comprising:
   scanning a patient's dentition with an intraoral scanner to gather an initial three-dimensional (3D) model of the patient's dentition;
   identifying a portion of the initial 3D model of the patient's dentition corresponding to a target tooth, the portion of the initial 3D model of the patient's dentition being associated with one or more visual attributes of the target tooth;
   standardizing the initial 3D model of the patient's dentition by expressing at least the portion of the initial 3D model corresponding to the target tooth as vectors from a center point of the target tooth;
   identifying one or more principal component analysis (PCA) features of the portion of the standardized initial 3D model corresponding to the target tooth, the one or more PCA features being correlated with the one or more visual attributes of the target tooth, wherein identifying the one or more PCA features comprises determining whether the vectors intersect a tooth shape of the target tooth and obtaining a limited number of the vectors at known angles in 3D space;
   determining one or more tooth eruption indicators of the target tooth using the one or more PCA features, the one or more tooth eruption indicators providing a basis to identify an eruption state of the target tooth, wherein determining the one or more tooth eruption indicators of the target tooth comprises using a machine-trained classifier to recognize one or more of an eruption status and a tooth type of the target tooth based on one or more PCA features of a 3D model of one or more representative teeth;
   predicting a spacing in the patient's dentition for accommodating eruption of the target tooth based on the one or more tooth eruption indicators;
   using the predicted space to generate an orthodontic treatment plan for the patient's dentition; and
   using the orthodontic treatment plan to fabricate a series of orthodontic aligners for treating the patient's dentition.

2. The method of claim 1, wherein the one or more tooth eruption indicators comprises one of: a primary erupted tooth, a permanent partially erupted or un-erupted tooth, and a permanent erupted tooth.

3. The method of claim 1, wherein the eruption state comprises one or more of the eruption status and a permanentness status of the target tooth.

4. The method of claim 3, wherein the permanentness status designates whether the target tooth is a permanent tooth or a primary tooth.

5. The method of claim 1, wherein determining the one or more tooth eruption indicators of the target tooth is based, at least in part on one or more of patient age, eruption sequence and patient gender.

6. The method of claim 1, wherein determining the one or more tooth eruption indicators comprises comparing the one or more PCA features with the one or more PCA features of the 3D model of the one or more representative teeth.

7. The method of claim 1, wherein determining the one or more tooth eruption indicators of the target tooth based on the PCA features comprises applying machine learning algorithms selected from the group consisting of Decision Tree, Random Forest, Logistic Regression, Support Vector Machine, AdaBOOST, K-Nearest Neighbor (KNN), Quadratic Discriminant Analysis, and Neural Network.

8. The method of claim 1, wherein the machine-trained classifier implements a convolutional neural network.

9. The method of claim 1, further comprising outputting a modified version of the initial 3D model of the patient's dentition to include tooth numbering based at least in part on the eruption state of the target tooth.

10. The method of claim 1, further comprising receiving a request to identify the one or more tooth eruption indicators of the target tooth; and wherein identifying one or more principal components is performed in response to the request.

11. The method of claim 1, wherein the orthodontic treatment plan comprises a pediatric orthodontic treatment plan for a pediatric patient.

12. The method of claim 1, further comprising outputting the one or more tooth eruption indicators, wherein outputting the one or more tooth eruption indicators comprises providing one or more tooth eruption indicator labels corresponding to the one or more tooth eruption indicators.

13. The method of claim 1, wherein identifying the portion of the standardized initial 3D model is part of an operation of segmenting the standardized initial 3D model of the patient's dentition.

14. The method of claim 1, wherein the series of orthodontic aligners apply forces to the patient's teeth according to a series of treatment stages, wherein one or more of the series of treatment stages is configured to accommodate the eruption of the target tooth based on the predicted spacing.

15. The method of claim 1, further comprising providing a visual representation of the patient's teeth including the one or more tooth eruption indicators.

16. A computer-implemented method of determining an orthodontic treatment plan for a patient's dentition, the method comprising:
converting, in a computing device, scan data from an intraoral scan of the patient's teeth into an initial three-dimensional (3D) model of the patient's teeth including a target tooth, wherein the initial 3D model is a digital mesh model;
segmenting the initial 3D model to obtain segmented tooth data representing a tooth shape of the target tooth;
determining, in the computing device, tooth shape features of the target tooth from the initial 3D model of the patient's teeth;
determining, in the computing device, tooth shape features of one or more reference teeth from the initial 3D model of the patient's teeth;
normalizing, in the computing device, at least some of the tooth shape features of the target tooth using the tooth shape features of the one or more reference teeth, wherein normalizing includes normalizing one or more of a mesial-distal width, a buccal-lingual width, a crown height, and a crown center of a 3D model of the target tooth to the one or more reference teeth;
applying a principal component analysis (PCA) on the normalized target tooth shape features to obtain one or more PCA features, wherein obtaining the PCA features comprises applying the PCA to the segmented tooth data to obtain a limited number of vectors that intersect the tooth shape of the target tooth at known angles in 3D space;
applying the PCA features to a machine-trained classifier of the computing device to determine an eruption status and an eruption permanentness status of the target tooth, wherein determining the eruption status includes determining whether the target tooth is fully erupted, partially erupted or un-erupted, wherein determining the eruption status and the eruption permanentness status includes determining whether the target tooth is a primary tooth or a permanent tooth;
predicting a spacing in the patient's dentition for accommodating eruption of the target tooth based on the eruption status and the eruption permanentness status;
using the predicted space to generate the orthodontic treatment plan for the patient's dentition; and
using the orthodontic treatment plan to fabricate a series of orthodontic aligners for treating the patient's dentition.

17. The computer-implemented method of claim 16, wherein normalizing includes determining a total number of cusps in buccal-mesial, buccal-distal, lingual-mesial, and lingual-distal arch direction surfaces.

18. The computer-implemented method of claim 16, further comprising collecting patient information including one or more of the patient's age, the patient's gender and tooth eruption sequence, wherein the patient information is used as supporting factors for predicting the eruption status and the eruption permanentness status of the target tooth.

19. The computer-implemented method of claim 16, wherein the one or more reference teeth includes one or more of a same-side first molar, opposite-side first molar, same-side central incisor, and opposite-side central incisor of the patient.

20. The computer-implemented method of claim 16, further comprising:
detecting whether a first molar or a central incisor of the patient is missing; and
normalizing based on an existing first molar or an existing central incisor of the patient.

21. The computer-implemented method of claim 16, further comprising using one or more tooth eruption indicators of the target tooth to segment the 3D model of the patient's dentition.

22. The computer-implemented method of claim 16, further comprising standardizing the initial 3D model of the patient's dentition by expressing at least a portion of the initial 3D model corresponding to the target tooth as vectors from a center point of the target tooth.

23. The computer-implemented method of claim 16, wherein converting the scan data into the 3D model comprises representing the patient's teeth as geometric point clouds or polyhedral objects in a format that can be rendered on a display.

* * * * *